(12) United States Patent
Duan et al.

(10) Patent No.: US 11,771,311 B2
(45) Date of Patent: Oct. 3, 2023

(54) SYSTEMS AND METHODS FOR COLLECTING AND SCREENING OF PANCREATIC SECRETIONS

(71) Applicant: AnX Robotica Corp, Pleasanton, CA (US)

(72) Inventors: Xiaodong Duan, Pleasanton, CA (US); Guohua Xiao, Plano, TX (US); Kevin Rubey, Ventura, CA (US)

(73) Assignee: AnX Robotica Corp, Pleasanton, CA (US)

( * ) Notice: Subject to any disclaimer, the term of this patent is extended or adjusted under 35 U.S.C. 154(b) by 0 days.

(21) Appl. No.: 17/384,101

(22) Filed: Jul. 23, 2021

(65) Prior Publication Data

US 2022/0022736 A1 Jan. 27, 2022

(30) Foreign Application Priority Data

Jul. 24, 2020 (CN) .......................... 202010725938.5

(51) Int. Cl.
| | |
|---|---|
| *A61B 1/04* | (2006.01) |
| *A61B 1/015* | (2006.01) |
| *A61B 1/05* | (2006.01) |
| *A61B 1/273* | (2006.01) |

(52) U.S. Cl.
CPC .............. *A61B 1/041* (2013.01); *A61B 1/015* (2013.01); *A61B 1/05* (2013.01); *A61B 1/273* (2013.01)

(58) Field of Classification Search
CPC ........... A61B 1/041; A61B 1/015; A61B 1/05; A61B 1/273
See application file for complete search history.

(56) References Cited

U.S. PATENT DOCUMENTS

| | | | |
|---|---|---|---|
| 4,195,624 | A | 4/1980 | Douglas |
| 4,198,960 | A | 4/1980 | Utsugi |
| 5,653,677 | A | 8/1997 | Okada et al. |
| 5,840,251 | A | 11/1998 | Iwaki |
| 8,235,888 | B2 | 8/2012 | Kawano |
| 8,269,823 | B2 | 9/2012 | Hirakawa et al. |
| 9,339,174 | B2 | 5/2016 | Gilad et al. |
| 9,392,929 | B2 | 7/2016 | Bendele et al. |
| 10,070,854 | B2 | 9/2018 | Duan et al. |
| 10,076,234 | B2 | 9/2018 | Duan et al. |
| 2002/0103417 | A1 | 8/2002 | Gazdzinski |

(Continued)

FOREIGN PATENT DOCUMENTS

| | | |
|---|---|---|
| CN | 103113606 A | 5/2013 |
| CN | 103304832 A | 9/2013 |

(Continued)

OTHER PUBLICATIONS

Zhao et al., Highly Sensitive Fluroescence Detection of Trypsin Based on Gold Nanoparticle Probes, Anal. Methods, 2016, 8, 393-400.*

(Continued)

*Primary Examiner* — Anh Tuan T Nguyen
*Assistant Examiner* — Rynae E Boler
(74) *Attorney, Agent, or Firm* — Cooley LLP

(57) ABSTRACT

Disclosed here are systems and methods for collecting and/or screening of a pancreatic secretion, using a capsule endoscope comprising an imaging system and a trypsin sensor, and a tether coupled to the capsule endoscope.

20 Claims, 37 Drawing Sheets

(56) References Cited

U.S. PATENT DOCUMENTS

| | | | |
|---|---|---|---|
| 2003/0013938 | A1 | 1/2003 | Iddan et al. |
| 2003/0139647 | A1 | 7/2003 | Raz et al. |
| 2004/0267095 | A1 | 12/2004 | Miyake et al. |
| 2005/0085697 | A1 | 4/2005 | Yokoi et al. |
| 2005/0267361 | A1 | 12/2005 | Younker et al. |
| 2006/0193893 | A1* | 8/2006 | Brown ............... A61L 31/16 514/56 |
| 2006/0235275 | A1 | 10/2006 | Rabinovitz et al. |
| 2007/0015961 | A1 | 1/2007 | Yamamoto et al. |
| 2007/0049796 | A1 | 3/2007 | Fujikura |
| 2007/0118018 | A1 | 5/2007 | Gilad et al. |
| 2007/0260175 | A1 | 11/2007 | Segawa et al. |
| 2007/0299309 | A1 | 12/2007 | Seibel et al. |
| 2008/0015413 | A1 | 1/2008 | Barlow et al. |
| 2008/0115606 | A1 | 5/2008 | Suzuki |
| 2008/0117291 | A1 | 5/2008 | Hirakawa et al. |
| 2008/0154093 | A1 | 6/2008 | Cho et al. |
| 2008/0160477 | A1 | 7/2008 | Stookey et al. |
| 2008/0167523 | A1 | 7/2008 | Uchiyama et al. |
| 2008/0167525 | A1 | 7/2008 | Wakefield |
| 2008/0177141 | A1 | 7/2008 | Wu et al. |
| 2009/0018396 | A1 | 1/2009 | Takizawa et al. |
| 2009/0062614 | A1 | 3/2009 | Adzich et al. |
| 2010/0322866 | A1* | 12/2010 | Rabinovitz ........ A61B 5/0084 424/9.1 |
| 2011/0065987 | A1* | 3/2011 | Mullick ............. A61B 1/126 600/109 |
| 2011/0184293 | A1* | 7/2011 | Rabinovitz ........ A61B 5/0084 424/9.1 |
| 2011/0254938 | A1 | 10/2011 | Asada et al. |
| 2011/0319639 | A1* | 12/2011 | Wessig ............. A61K 49/0021 549/338 |
| 2012/0095391 | A1 | 4/2012 | Bendele et al. |
| 2012/0101331 | A1* | 4/2012 | Gilad ................ A61B 1/041 600/114 |
| 2012/0165796 | A1 | 6/2012 | Ortiz et al. |
| 2014/0206016 | A1* | 7/2014 | Lozano ............. C12Q 1/045 435/7.1 |
| 2014/0243598 | A1 | 8/2014 | Genier et al. |
| 2015/0011829 | A1 | 1/2015 | Wang et al. |
| 2016/0235282 | A1 | 8/2016 | Nakamura |
| 2019/0099067 | A1 | 4/2019 | Tseng |
| 2020/0037862 | A1 | 2/2020 | Duan et al. |
| 2020/0196873 | A1 | 6/2020 | Ntziachristos et al. |
| 2020/0323422 | A1 | 10/2020 | Duan |

FOREIGN PATENT DOCUMENTS

| | | | |
|---|---|---|---|
| CN | 107064131 | A | 8/2017 |
| CN | 109813666 | A * | 5/2019 |
| CN | 109924937 | A | 6/2019 |
| CN | 111202528 | A | 5/2020 |
| CN | 111808916 | A | 10/2020 |
| WO | WO-2019/171409 | A1 | 9/2019 |

OTHER PUBLICATIONS

Chen, R. et al. (2006). "Quantitative Proteomic Profiling of Pancreatic Cancer Juice," Proteomics 6:3871-3879.

Eshleman, J.R. et al. (2015). "KRAS and Guanine Nucleotide-Binding Protein Mutations in Pancreatic Juice Collected from the Duodenum of Patients at High Risk for Neoplasia Undergoing Endoscopic Ultrasound." Clinical Gastroenterology and Hepatology 13:963-969.e4.

Farrell, J.J. et al. (2005). "Early Detection Markers in Pancreas Cancer," Cancer Biomarkers 1:157-175.

Fujiyama, Y. et al. (2020). "Promoter DNA Hypermethylation of the Cysteine Dioxygenase 1 (CDO1) Gene in Intraductal Papillary Mucinous Neoplasm (IPMN)," Annals of Surgical Oncology 27:4007-4016.

Hayakawa, H. et al. (2019). "Carcinoembryonic Antigen Level in the Pancreatic Juice Is Effective in Malignancy Diagnosis and Prediction of Future Malignant Transformation of Intraductal Papillary Mucinous Neoplasm of the Pancreas," Journal of Gastroenterology 54:1029-1037.

International Search Report dated Aug. 19. 2020, for PCT Application No. PCT/US2020/027422, filed on Apr. 9, 2020, 4 pages.

Majumder, S. et al. (2020). "Methylated DNA in Pancreatic Juice Distinguishes Patients with Pancreatic Cancer from Controls," Clinical Gastroenterology and Hepatology 18:676-683.e3.

Majumder, S. et al. (2019). "Novel Methylated DNA Markers Discriminate Advanced Neoplasia in Pancreatic Cysts: Marker Discovery, Tissue Validation, and Cyst Fluid Testing," The American Journal of Gastroenterology 114:1539-1549.

Mori, Y. et al. (2013). "A Minimally Invasive and Simple Screening Test for Detection of Pancreatic Ductal Adenocarcinoma Using Biomarkers in Duodenal Juice," Pancreas 42:187-192.

Nakamura, S. et al., (2019). "Pancreatic Juice Exosomal MicroRNAs as Biomarkers for Detection of Pancreatic Ductal Adenocarcinoma," Annals of Surgical Oncology 26:2104-2111.

Nakashima, A. et al. (2009). "Usefulness of Human Telomerase Reverse Transcriptase in Pancreatic Juice as a Biomarker of Pancreatic Malignancy," Pancreas 38:527-533.

Singhi, A.D. et al. (2018). "Preoperative Next-Generation Sequencing of Pancreatic Cyst Fluid Is Highly Accurate in Cyst Classification and Detection of Advanced Neoplasia," Gut 67:2131-2141.

Springer, S. et al. (2015). "A Combination of Molecular Markers and Clinical Features Improve the Classification of Pancreatic Cysts," Gastroenterology 149:1501-1510.

Tanaka, M. et al. (2019). "Cytologic Analysis of Pancreatic Juice Increases Specificity of Detection of Malignant IPMN—A Systematic Review," Clinical Gastroenterology and Hepatology 17:2199-2211.e21.

Tian, T. et al. (2017). "Pathomechanisms of Oxidative Stress in inflammatory Bowel Disease and Potential Antioxidant Therapies," Oxidative Medicine and Cellular Longevity 2017:4535194.

Tobi, M. et al. (2013). "Prospective Markers for Early Diagnosis and Prognosis of Sporadic Pancreatic Ductal Adenocarcinoma," Digestive Diseases and Sciences 58:744-750.

Wang, J. et al. (2014). "Circulating MicroRNAs in Pancreatic Juice as Candidate Biomarkers of Pancreatic Cancer," Journal of Cancer 5:696-705.

Written Opinion of the International Searching Authority dated Aug. 19, 2020, for PCT Application No. PCT/US2020/027422, filed on Apr. 9, 2020, 9 pages.

Yu, J. et al. (2017). "Digital Next-Generation Sequencing Identifies Low-Abundance Mutations in Pancreatic Juice Samples Collected from the Duodenum of Patients with Pancreatic Cancer and Intraductal Papillary Mucinous Neoplasms," Gut 66:1677-1687.

Chinese Office Action dated Jun. 10, 2022, for Application No. 202010725938.5, filed on Jul. 23, 2021, 14 total pages (with English Translation).

Final Office Action dated Jul. 28, 2022, for U.S. Appl. No. 16/844,248, filed on Apr. 9, 2020, 12 pages.

International Search Report dated Oct. 20, 2021, for PCT Application No. PCT/US2021/108258, filed on Jul. 23, 2021, 7 pages (with English Translation).

Non-Final Office Action dated Jan. 31, 2022, for U.S. Appl. No. 16/844,248, filed on Apr. 9, 2020, 11 pages.

Extended European Search Report dated Dec. 5, 2022, for EP Application No. 20 787 566.7, filed on Apr. 9, 2020, 8 pages.

Non-Final Office Action dated Jan. 23, 2023, for U.S. Appl. No. 16/844,248, filed Apr. 9, 2020, 12 pages.

* cited by examiner

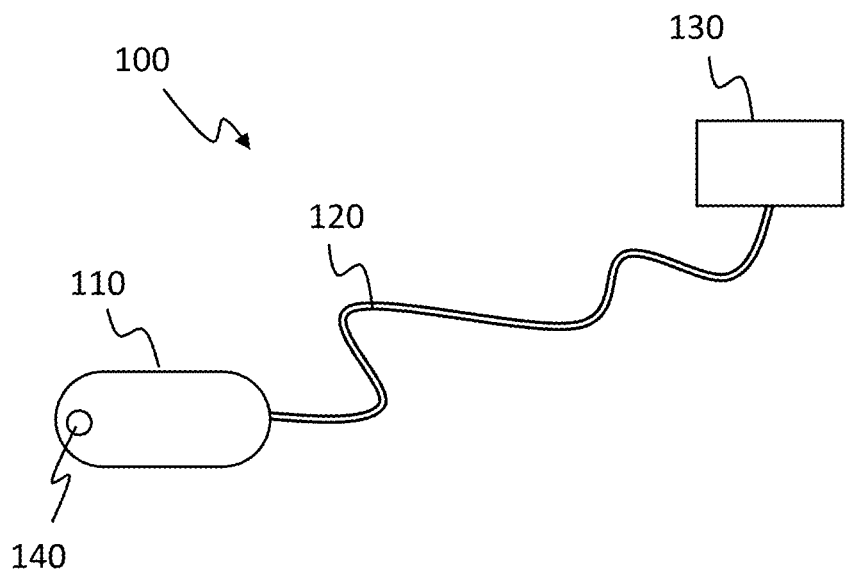
FIG. 1A
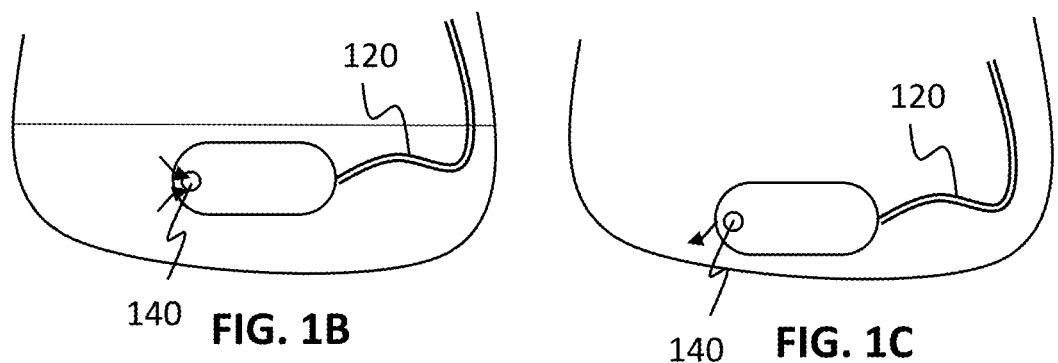
FIG. 1B  FIG. 1C

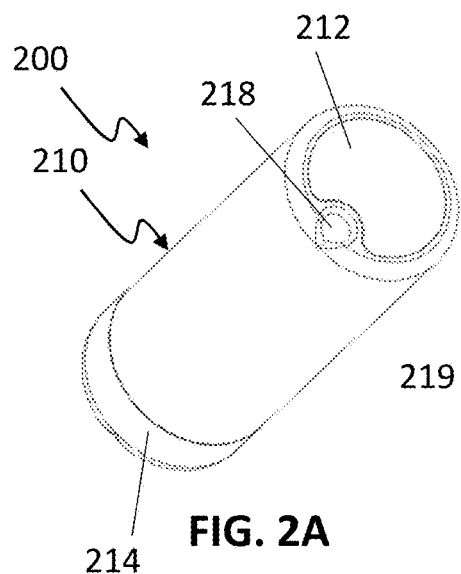
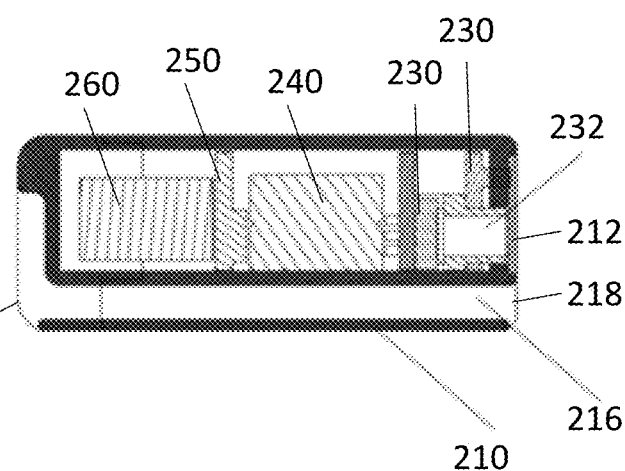
FIG. 2A
FIG. 2B
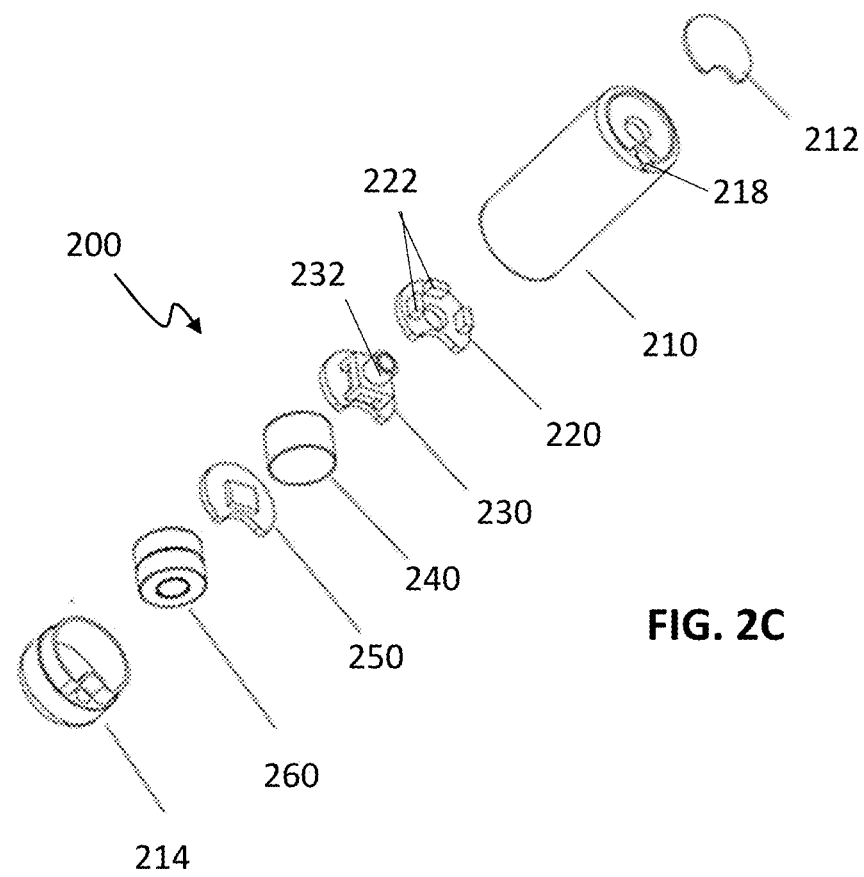
FIG. 2C

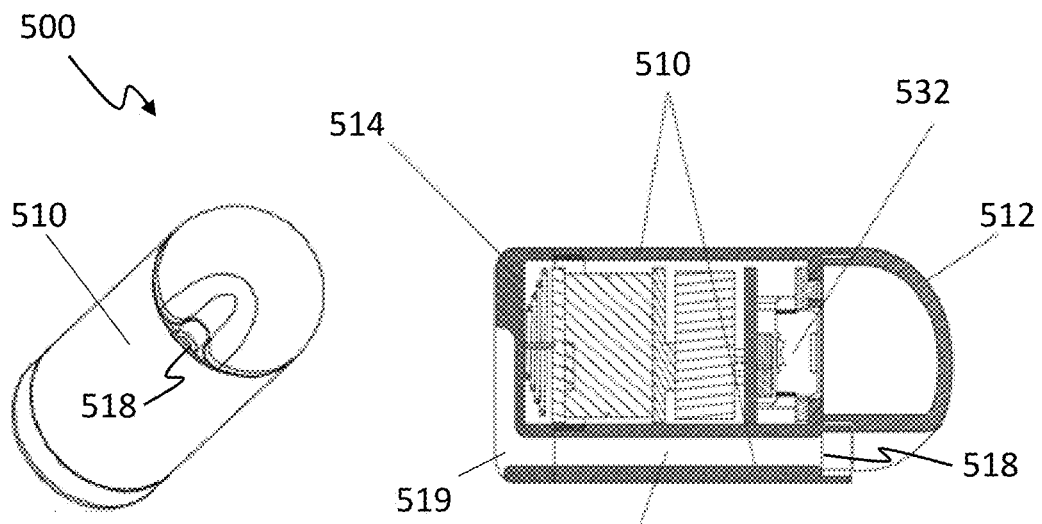
FIG. 5A
FIG. 5B
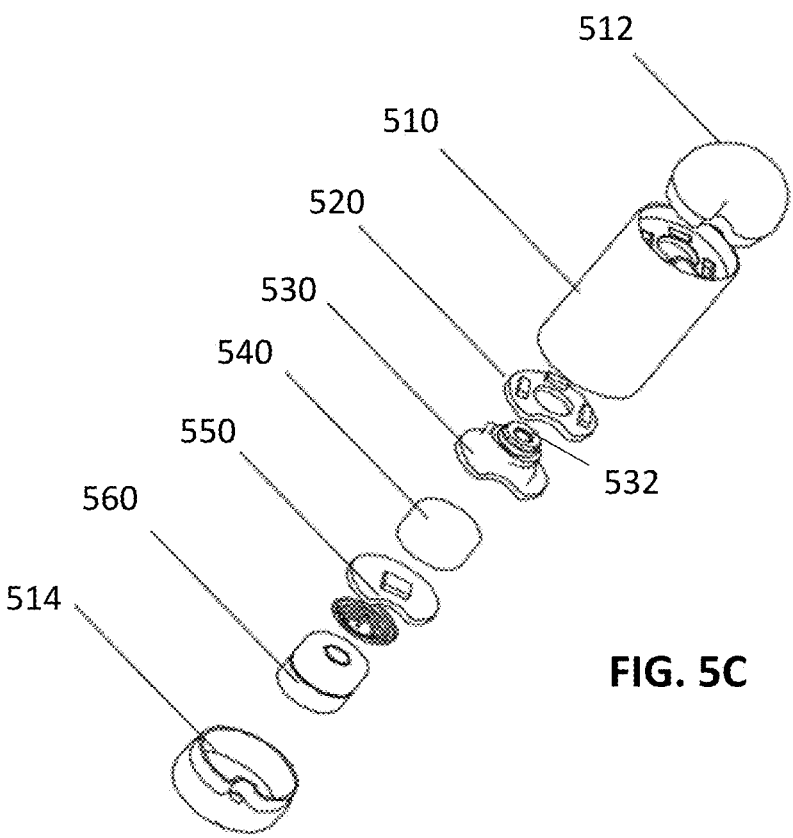
FIG. 5C

1000

FIG. 10A tube : SPEC material : silicone elastomer
shore hardness : 35~65 unit:mm  ⌀1 +0.3/-0.1
⌀0.5±0.1

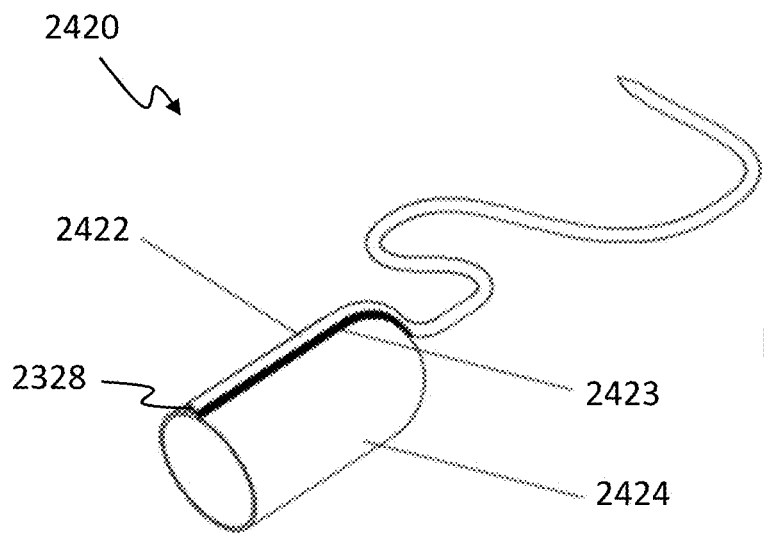
FIG. 24A
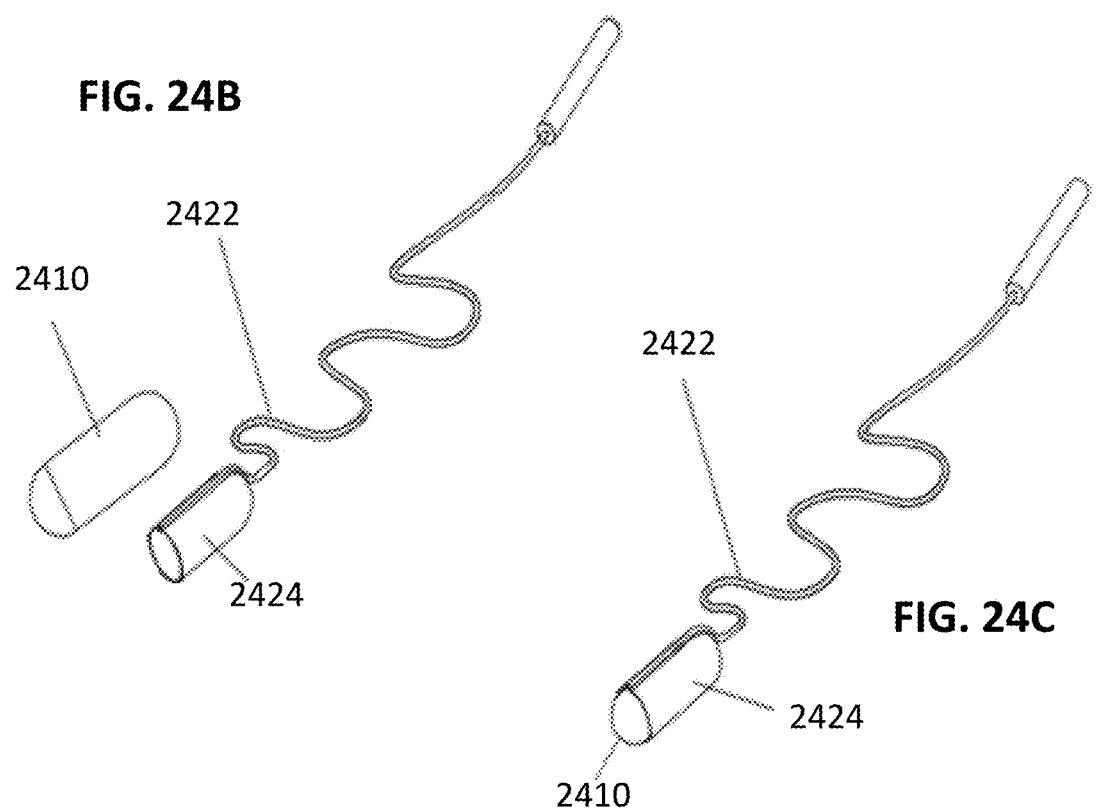
FIG. 24B
FIG. 24C

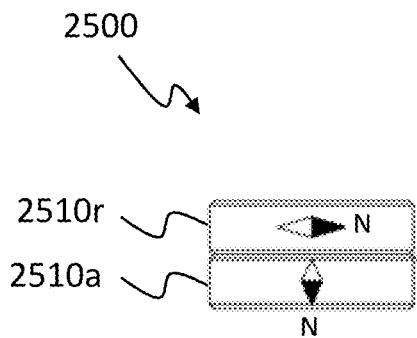
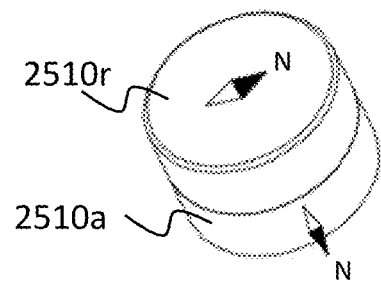
FIG. 25A  FIG. 25B
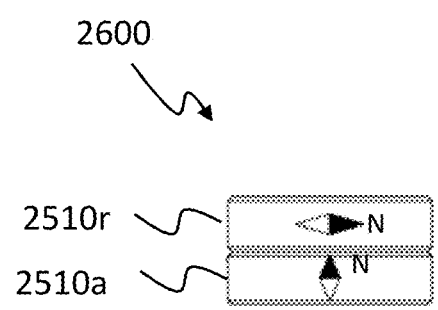
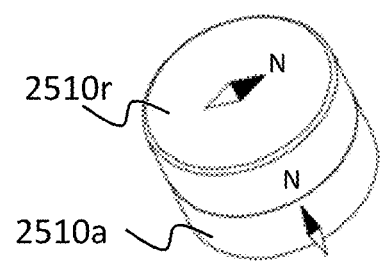
FIG. 26A  FIG. 26B

SYSTEMS AND METHODS FOR COLLECTING AND SCREENING OF PANCREATIC SECRETIONS

CROSS-REFERENCE TO RELATED APPLICATIONS

This application claims priority to Chinese Patent Application Serial No. 202010725938.5 filed on Jul. 24, 2020, which is hereby incorporated by reference in its entirety.

TECHNICAL FIELD

This invention relates generally to the field of medical treatment and more specifically to biopsy and drug delivery for patients.

BACKGROUND

Pancreatic cancer accounts for about 3% of all cancers in the United States but is the fourth leading cause of cancer death and has a 5-year survival rate of about 10%. Pancreatic cancer is seldom detected at its early stages when it's most curable because the pancreas is located deep in the abdomen and often does not show symptoms until after the cancer has spread to other organs. Currently, there are no validated, specific screening tests that can easily and reliably find early-stage pancreatic cancer in people who have no symptoms. This means it is often not found until later stages when the cancer can no longer be removed with surgery and/or has spread from the pancreas to other parts of the body. Early detection of pancreatic cancer can be the key to improve clinical outcome in patients. For example, if the cancer is detected at an early stage when surgical removal of the tumor is possible, the 5-year survival rate is 39%. In contrast, the 5-year survival rate for people who are diagnosed after the cancer has spread to a distant part of the body is only 3%.

One potential screening strategy is to examine circulating tumor cells (CTCs), shed cancer cells, or circulating exosomes in a blood sample. However, blood samples have a high concentration of non-tumor species, which may negatively affect the sensitivity and/or accuracy of such tests based on blood sample. Pancreatic juice, a liquid secreted by the pancreas, has a high concentration of tumor-derived species, including circulating tumor DNA (ctDNA) and tumor-derived exosomes. Conventional methods for obtaining a biopsy of pancreatic juice include endoscopic retrograde cholangiopancreatography (ERCP) and endoscopic ultrasound-guided fine-needle aspiration (EUS-FNA). However, these methods are typically more invasive and may lead to complications such as pancreatitis, infections, hemorrhage, and bowel perforation. Therefore, there is a need for new and improved non-invasive systems and methods for accessing pancreas and/or obtaining pancreatic juice in a patient.

SUMMARY

In one aspect, disclosed herein is a system, comprising: a capsule endoscope comprising an imaging system and a trypsin sensor, wherein the trypsin sensor is configured to detect trypsin in a fluid that is in contact with the trypsin sensor; and a tether comprising a flexible member comprising a lumen, wherein the flexible member is in fluidic communication with the capsule endoscope. In some variations, the trypsin sensor comprises a trypsin detection film. In some variations, the trypsin detection film comprises a substrate and a dye attached to the substrate. In some variations, the dye is in contact with the fluid and changes color, wherein trypsin is present in the fluid. In some variations, the dye changes color when in contact with fluid having a trypsin concentration of at least about 300 μg/mL. In some variations, the trypsin sensor is configured to detect fluid comprising a pancreatic secretion, thereby identifying the location of duodenal papilla. In some variations, the system is configured to withdraw a sample comprising the pancreatic secretion. In some variations, the dye is selected from the group consisting of bromocresol purple dye, 3',5,5'-tetramethyl benzidine dye, triarylmethane dye, xylenol orange dye, and metal complex dye. In some variations, the concentration of the dye is about 0.25 to 2.5 mg/mL. In some variations, the substrate is a polymeric film substrate. In some variations, the polymeric film substrate comprises bromobutane, vinylimidazole, acrylonitrile, or any combination thereof. In some variations, the polymeric film substrate comprises bromobutane and vinylimidazole, wherein the molar ratio of bromobutane to vinylimidazole is from 2:1 to 1:1. In some variations, the polymeric film substrate comprises bromobutane and vinylimidazole, and acrylonitrile, wherein the mass of acrylonitrile is greater than or equal to the sum of the masses of bromobutane and vinylimidazole. In some variations, the system further comprises a vacuum source arranged in fluidic communication with the lumen. In some variations, the vacuum source comprises a syringe or pump. In some variations, the tether comprises a clamp configured to engage the capsule endoscope. In some variations, the clamp is configured to releasably engage the capsule endoscope. In some variations, the clamp comprises a port in fluidic communication with the lumen.

In another aspect, disclosed herein is a method, comprising: advancing a capsule endoscope into a gastrointestinal tract of a patient, wherein the capsule endoscope comprises an imaging system and a trypsin sensor, and wherein the capsule endoscope is in fluidic communication with a tether comprising a flexible member with a lumen; positioning the capsule endoscope at a region of interest; detecting trypsin in a fluid that is in contact with the trypsin sensor; and withdrawing a sample from the region of interest through the lumen. In some variations, withdrawing the sample from the region of interest comprises applying negative pressure to the lumen. In some variations, applying negative pressure comprises using a vacuum source arranged in fluidic communication with the lumen. In some variations, the vacuum source comprises a syringe or pump. In some variations, withdrawing the sample from the region of interest comprises withdrawing the sample through a port in fluidic communication with the lumen. In some variations, the port is on the capsule endoscope or tether. In some variations, detecting trypsin in the fluid comprises contacting the trypsin detection film with the fluid and detecting a color change of the trypsin detection film, wherein trypsin is present in the fluid. In some variations, the trypsin detection film is configured to change color when in contact with fluid having a trypsin concentration of at least about 300 μg/mL. In some variations, the method further comprises identifying the location of duodenal papilla by detecting trypsin in the fluid. In some variations, the method further comprises stimulating a pancreatic secretion from the patient. In some variations, stimulating the pancreatic secretion comprises providing a visual stimulator to the patient. In some variations, stimulating the pancreatic secretion comprises administering a hormone comprising secretin or cholecystokinin to the patient. In some variations, the trypsin sensor comprises a trypsin detection film. In some variations, the trypsin detection film comprises a substrate and a dye attached to the substrate. In some variations, the dye is selected from the group consisting of bromocresol purple dye, 3',5,5'-tetramethyl benzidine dye, triarylmethane dye, xylenol orange dye, and metal complex dye. In some variations, the concentration of the dye is about 0.25 to 2.5 mg/mL. In some variations, the substrate is a polymeric film substrate. In some variations, the polymeric film substrate comprises bromobutane, vinylimidazole, acrylonitrile, or any combination thereof. In some variations, the polymeric film substrate comprises bromobutane and vinylimidazole, wherein the molar ratio of bromobutane to vinylimidazole is from 2:1 to 1:1. In some variations, the polymeric film substrate comprises bromobutane and vinylimidazole, and acrylonitrile, wherein the mass of acrylonitrile is greater than or equal to the sum of the masses of bromobutane and vinylimidazole. In some variations, the method further comprises screening one or more biomarkers in the sample. In some variations, the one or more biomarkers comprise KRAS, GNAS, TP53, PIK3CA, PTEN, SMAD4, CDO1, C13orf18, FER1L4, BMP3, FOXE1, SLIT2, EYA4, SFRP1, TBX15, BMP3, PKRCB, ppENK, CD1D, KCNK12, CLEC11A, NDRG4, IKZF1, PKRCB, KRAS, miR-221, miR-21, miR-205, miR-210c, ex-miR-21, ex-miR-155, adnab-9, K-ras, her-2/neu, or any combination thereof. In some variations, the one or more biomarkers comprise CA19-9 (cancer antigen 19-9), miRNA-25, CA-125 (cancer antigen 125), CEA (carcinoembryonic antigen), or any combination thereof.

Generally, in some variations, a system for accessing a patient includes a capsule endoscope comprising an imaging system and a port configured to permit passage of fluid. The system may further include a tether coupled to the capsule endoscope and include a flexible member, where the flexible member includes a lumen in fluidic communication with the port. Furthermore, in some variations the tether may include a clamp configured to engage the capsule endoscope, and the clamp may be configured to releasably engage the capsule endoscope. The system may further include a pressure source and/or vacuum source (e.g., syringe, pump, etc.) arranged in fluidic communication with the lumen.

In some variations, the capsule endoscope may be magnetically controllable, such as with an external magnetic control system. The capsule endoscope may include one or more suitable compartments or other structures for conveying fluid between the lumen and port. In some variations, the compartment may include an elongated channel having a proximal end in fluidic communication with the lumen and a distal end in fluidic communication with the port. The elongated channel may, for example, extend from a proximal portion of the capsule endoscope to a distal portion of the capsule endoscope. In some variations, the compartment may include a chamber. The chamber may, for example, be in a proximal portion of the capsule endoscope.

Additionally, generally in some variations, a system for accessing a patient includes a capsule endoscope including an imaging system, and a tether including a clamp configured to engage the capsule endoscope, and a flexible member including a lumen, where the clamp includes a port in fluidic communication with the lumen. In some variations, the imaging system may include a first lens on a proximal portion of the capsule endoscope, and/or a second lens on a distal portion of the capsule endoscope. The endoscope may be magnetically controllable. Furthermore, in some variations the tether may include a clamp configured to engage the capsule endoscope, and the clamp may be configured to releasably engage the capsule endoscope. The system may further include a pressure source and/or vacuum source (e.g., syringe, pump, etc.) arranged in fluidic communication with the lumen.

In some variations, the clamp of the tether may include a sheath configured to surround at least a portion of the capsule endoscope. The clamp may, in some variations, include an anchor member coupling the sheath and the flexible member of the tether. In some variations, the port may be on the anchor member and axially offset from a proximal portion of the capsule endoscope. For example, the anchor may include one or more arcuate structures coupled to the sheath to provide an offset or a window region between the port and the capsule endoscope. Furthermore, in some variations, the clamp may include a housing defining a chamber between the sheath and the flexible member, and the port may be in the housing. In some of these variations, the housing may further include a valve (e.g., one-way valve).

Additionally, generally in some variations, a system for accessing a patient includes a capsule endoscope including an imaging system having a field of view, and a tether including a flexible member having a port. The port may be within the field of view of the imaging system, and the port may be configured to permit passage of fluid. In some variations, the imaging system may include a lens on a proximal portion of the capsule endoscope and/or a distal portion of the capsule endoscope. In some variations, the capsule endoscope may be magnetically controllable. The system may further include a pressure source and/or vacuum source (e.g., syringe, pump, etc.) arranged in fluidic communication with the lumen.

The flexible member may be coupled to the capsule endoscope in some variations. For example, the capsule endoscope may include a housing and at least a longitudinal portion of the flexible member may be coupled to the housing.

Additionally or alternatively, in some variations the flexible member may be coupled to a portion of the tether, such as a clamp that is configured to engage the capsule endoscope. In these variations, at least a longitudinal portion of the flexible member may be coupled to the clamp. The clamp may, for example, be configured to releasably engage the capsule endoscope.

Generally, in some variations, a method of accessing a patient includes advancing a capsule endoscope into a gastrointestinal tract of a patient, where the capsule endoscope is coupled to a tether including a flexible member with a lumen, positioning the capsule endoscope at a region of interest, and administering a therapeutic substance to the region of interest through the lumen. Administering the therapeutic substance may, for example, including administering the therapeutic substance through a port in fluidic communication with the lumen. For example, the port may be on the capsule endoscope or the tether. The therapeutic substance may be administered at least in part by applying positive pressure to the lumen. In some variations, the method may further include separating the capsule endoscope from the tether, then administering the therapeutic substance after separating the capsule endoscope from the tether.

Additionally, in some variations, a method of accessing a patient includes advancing a capsule endoscope into a gastrointestinal tract of a patient, where the capsule endoscope is coupled to a tether including a flexible member with a lumen, positioning the capsule endoscope at a region of interest, and withdrawing a patient sample from the region of interest through the lumen. Withdrawing a patient sample may, for example, including withdrawing a patient sample through a port in fluidic communication with the lumen. For example, the port may be on the capsule endoscope or the tether. The patient sample may be withdrawn at least in part by applying negative pressure to the lumen. In some variations, the method may further include separating the capsule endoscope from the tether, then withdrawing a patient sample after separating the capsule endoscope from the tether.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 1A is an illustrative schematic depicting an exemplary variation of a capsule endoscope system for accessing a patient. FIG. 1B is an illustrative schematic depicting a method for performing liquid biopsy using an exemplary variation of a capsule endoscope system for accessing a patient. FIG. 1C is an illustrative schematic depicting a method for performing drug delivery using an exemplary variation of a capsule endoscope system for accessing a patient.

FIGS. 2A-2C are perspective, longitudinal cross-sectional, and exploded views, respectively, of an exemplary variation of a capsule endoscope with a port at its distal portion.

FIGS. 5A-5C are perspective, longitudinal cross-sectional, and exploded views, respectively, of an exemplary variation of a capsule endoscope with a port at its distal portion.

FIG. 10A is an illustrative schematic depicting a flexible member in an exemplary variation of a tether. FIG. 10B is an illustrative schematic depicting exemplary dimension ranges of a flexible member of a tether.

FIG. 24A is an illustrative schematic of another exemplary variation of a tether including a clamp configured to engage or receive a capsule endoscope. FIGS. 24B and 24C are illustrative schematics of a tethered system including the tether variation depicted in FIG. 24A.

FIGS. 25A and 25B are side and perspective schematic views, respectively, of one exemplary variation of an internal magnet assembly in a capsule endoscope.

FIGS. 26A and 26B are side and perspective schematic views, respectively, of another exemplary variation of an internal magnet assembly in a capsule endoscope.

DETAILED DESCRIPTION

Figure 2D:
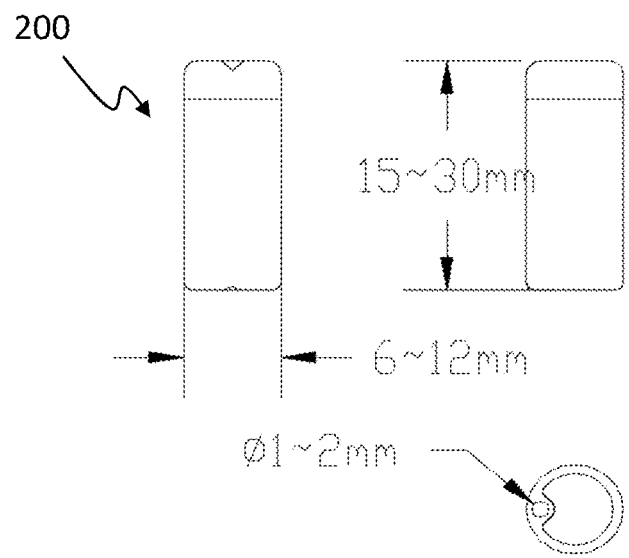
FIG. 2D is an illustrative schematic depicting exemplary dimension ranges of the capsule endoscope depicted in FIGS. 2A-2C.

Non-limiting examples of various aspects and variations of the invention are described herein and illustrated in the accompanying drawings.

Overview

Generally, a system for accessing a patient (e.g., for liquid biopsy, drug delivery, etc.) may include a capsule endoscope and a tether coupled to the capsule endoscope. The capsule endoscope may, for example, include an imaging system that enables visualization (e.g., through still images, videos, etc.) of its surroundings. In some variations, the capsule endoscope may include one or more magnets such that the capsule endoscope may be controlled at least in part through a magnetic control system. The tether coupled to the capsule endoscope may include a flexible member with a lumen in fluidic communication with a port configured to permit passage of fluid, and the port may be, for example, on the capsule endoscope or the tether. In some variations, the flexible member may be coupled to the capsule endoscope directly, while in some variations, the flexible member may be coupled to the capsule endoscope via a clamp or other suitable intervening attachment.

For example, as shown in the exemplary schematic of FIG. 1A, a system 100 for accessing a patient may include a capsule endoscope 110 and a tether 120 including a flexible member coupled to the capsule endoscope. A pressure modulator 130, such as a pressure source or a vacuum source (e.g., syringe or pump), may be coupled to the tether so as to be in fluidic communication with a lumen of the flexible member and a port 140 that permits passage of fluid. Although the port 140 is shown in FIGS. 1A-1C as located on a distal portion of the capsule endoscope 110, it should be understood that in other variations, a port 140 may additionally or alternatively be located on other suitable portions of the capsule endoscope (e.g., a proximal portion of the capsule endoscope 110, a central portion of the capsule endoscope 110). Furthermore, in other variations at least one port may be located on the tether (e.g., on distal portion of the flexible member, on a clamp member of the tether, etc.). Other exemplary variations of the system, including examples of suitable arrangements for the port, are described in further detail below.

During use, the capsule endoscope may be advanced into a body cavity such as a gastrointestinal tract of a patient, with the tether trailing the capsule endoscope and extending external to the patient. The capsule endoscope may be advanced to a region of interest. The imaging system of the capsule endoscope may aid such navigation by, for example, providing visibility to an operator of the location of the capsule endoscope relative to the region of interest, the surrounding conditions near the capsule endoscope (e.g., for determining whether sufficient patient fluid in the body cavity for biopsy is present, for determining whether lesions or other diseased conditions are present, etc.). At the region of interest, a liquid biopsy or patient sample may be withdrawn from the patient through the port. For example, a vacuum source (e.g., syringe with withdrawn plunger, vacuum pump, etc.) may be coupled to the tether so as to introduce a negative pressure in the tether, which draws a liquid biopsy through the port as shown in FIG. 1B, through the tether, and to a collection point external to the patient. Additionally or alternatively, a pressure source (e.g., syringe with depressed plunger, pressure pump, etc.) may be coupled to the tether so as to introduce a positive pressure in the tether, which may urge a therapeutic substance (e.g., drug) through the tether and through the port to a region of interest (e.g., lesion) as shown in FIG. 1C. Other exemplary aspects of methods for using the system are described below.

Generally, the systems and methods described herein are comfortable and non-invasive to a patient, thereby reducing risk of dangerous complications such as infection, hemorrhage, and perforations. The systems and methods may be used in various applications for liquid biopsy and/or drug delivery. For example, the system may be used to draw pancreatic juice from a patient, or to sample intestinal flora in a patient. As another example, the system may be used to deliver drugs to lesions (e.g., in the esophagus) or to one or more regions of interest in the small intestine, such as to treat irritable bowel disorder (IBD) or other conditions. As yet another example, drug delivery may be concurrent with controlled movement of the capsule endoscope, such as for spraying or otherwise releasing a drug across a surface (e.g., internal surface region of the stomach).

One specific application of the systems and methods described herein can be detecting a pancreatic secretion (e.g., pancreatic juice) by using a trypsin detection film, and/or collecting the pancreatic secretion. Trypsin is a digestive enzyme in pancreatic exocrine fluid. Trypsin catalyzes the hydrolysis of peptide bonds, breaking down proteins into smaller peptides. Trypsin is produced as an inactive form (zymogen trypsinogen) in the pancreas. When the pancreas is stimulated by cholecystokinin, trypsin is then secreted into the first part of the small intestine (i.e., the duodenum) via the pancreatic duct. Once in the small intestine, the enzyme enteropeptidase activates trypsinogen into trypsin by proteolytic cleavage. Trypsin is available in high quantity in pancreases and can be used as a marker for detecting pancreatic-origin digestive juice (i.e., pancreatic juice).

Capsule Endoscope

Generally, the capsule endoscope may include a housing enclosing various endoscope components. For example, the capsule endoscope may include an imaging system, an illumination system, a communication module, and/or a power source. In some variations, the capsule endoscope may include one or more magnets for facilitating movement control (e.g., navigation, rotation, etc.) of the capsule endoscope by a magnetic control system external to the patient, as described in further detail below. Other electronics, such as a posture sensor (e.g., gyroscope), controller(s), etc. may further be included in the housing. Furthermore, in some variations, the capsule endoscope may include a port configured to permit passage of fluid in and/or out of the capsule endoscope. As described in further detail below, the port may be located, for example, on a distal end of the capsule endoscope or a proximal end of the capsule endoscope (or other suitable location). In some of these variations, the capsule endoscope may include a center of gravity that is biased toward the port, such that the gravity tends to help the port be submerged in fluid for obtaining liquid biopsy. Additionally or alternatively, the capsule endoscope may include a buoyant element that is on an opposite side or end of capsule endoscope relative to the port, such that the buoyant element tends to help the port be submerged in fluid for obtaining liquid biopsy.

Generally, the housing may provide an overall casing and shape for the capsule endoscope. The housing may have rounded or beveled edges so as to reduce risk of tissue damage when the capsule endoscope is advanced through a body cavity (e.g., gastrointestinal tract) of a patient. The housing may include one or more interior volumes within which the endoscope components may reside. These volumes may be fluid-tight sealed, such as through mechanical interfit (e.g., press fit) components and/or epoxy, etc. The housing may, for example, include a biocompatible plastic that is injection-molded or formed in any suitable manner.

The imaging system of the capsule endoscope may, for example, assist navigation of the capsule endoscope within the patient and/or enable visual assessment of surrounding patient tissue (e.g., confirmation of presence of fluid for available for biopsy, identification of lesions, etc.). The imaging system may include one or more suitable image sensors, such as CMOS image sensors, for obtaining images of the environment around the capsule endoscope. For example, one or more image sensors may have a field of view including the environment around the capsule endoscope. The illumination system may include one or more suitable light sources, such as light-emitting diodes (LEDs) arranged to illuminate a field of view of the imaging system.

Control signals and/or image data may be communicated to and from the capsule endoscope through a communication module in the capsule endoscope. The communication module may, for example, be a wireless communication module including a suitable RF antenna arrangement on a processing circuit board. In other variations, the capsule endoscope may alternatively include a communication module configured to communicate via a wired connection which may, for example, travel external to the patient via the tether.

One or more power sources function to supply power to the various capsule components. The power source may, for example, include a suitable battery. In some variations, a controller may operate the power source to provide different power states for the capsule endoscope, such as an inactive state in which the capsule endoscope draws a low amount of power (e.g., for storage, transport, etc.) and an active state in which the capsule endoscope utilizes a higher amount of power (e.g., for imaging).

In some variations, the capsule endoscope may include an opto-electronic switching starter installed near the illumination system. The opto-electronic switching starter may be arranged adjacent the light sources and include, for example, a field effect transistor (FET) and an electronic switch connected with the FET. When light is generated by the illumination unit, the light may shine on the opto-electronic switching starter, causing the electronic switch to be turned on or activated. This activation of the electronic switch may effectively activate the capsule endoscope from a low power state (e.g., during advancement of the capsule endoscope) to an operational power state (e.g., for imaging of a region of interest). For example, the activation of the electronic switch may generate an opening pulse that causes the power source to electronically connect to other components of the capsule endoscope such as the imaging system, the wireless communication module 250, etc. This and other exemplary aspects of the capsule endoscope are described in further detail in U.S. Patent Publication No. 2015/0011829, which is hereby incorporated in its entirety by this reference.

Various exemplary variations of capsule endoscopes having different arrangements of endoscope components are described in further detail below.

FIGS. 2A-2C depict an exemplary variation of a capsule endoscope 200 including a port 218 at a distal end of the capsule endoscope 200. As shown in FIGS. 2B and 2C, the capsule endoscope 200 may include a housing 210 that encloses various endoscope components, such as an imaging system 230, an illumination system 220, one or more magnets 240, a wireless communication module 250, and/or one or more power sources 260. Except as described below, the imaging system 230, the illumination system 220, the wireless communication module 250, and one or more power sources 260 may be similar to those described above. In some variations, other electronics such as a posture sensor (e.g., gyroscope), controller(s), etc. may further be included in the housing 210.

As shown in FIG. 2D, the housing 210 may be generally cylindrical, with rounded or beveled edges. The housing 210 may include a generally cylindrical central section including one or more internal volumes for containing endoscopic components. The central section may be capped at its proximal (rear) and distal (front) ends with a proximal cover 214 and a distal cover 212. As shown in FIGS. 2A-2D the proximal and distal covers may be substantially flat or planar. The proximal cover 214 and/or distal cover 212 may include an optically transparent material (e.g., acrylic) that enables visibility and/or illumination of the environment external to the capsule endoscope by the imaging system and illumination system within the capsule endoscope. Exemplary dimensions of the housing are a length of between about 15 mm to about 30 mm, and a diameter of between about 6 mm to about 12 mm. Such dimensions may, for example, be small enough to allow passage of the capsule endoscope into the gastrointestinal tract without substantial discomfort or pain, but large enough to house the endoscope components.

As described above, the capsule endoscope 200 may include one or more magnets 240. The one or more magnets 240 may be controllable by an external magnetic control system, as further described below. The one or more magnets 240 may, for example, be configured to allow manipulation of the capsule endoscope with 6 degrees of freedom (DOF), including translational motion along three perpendicular axes, as well as rotational motion along three perpendicular axes (yaw, pitch, roll). In some variations, however, the capsule endoscope 200 may omit magnets 240. For example, instead of being controlled by an external magnetic control system, the capsule endoscope may be advanced through peristalsis in the gastrointestinal tract of a patient.

The imaging system 230 and/or illumination system 220 may be similar to the imaging and illumination systems described above. For example, as shown in FIG. 2C, an illumination system 220 may include three LEDs 222 arranged on a circuit board to emit light (e.g., white light) through a transparent window in the distal cover 212 of the housing 210. Although three LEDs are shown in FIG. 2C, it should be understood that any suitable number (e.g., one, two, four, five or more) may be included in the illumination system 220. The LEDs 222 may be distributed around a lens 232 of the imaging system 230, such as to provide visibility in the field of view of the imaging system 230. Furthermore, the LEDs 222 and the imaging system 230 may be arranged proximate the port 218 (e.g., on a distal portion of the capsule endoscope), such that the illuminated field of view may provide visibility into the environment immediately around the port 218. Accordingly, the imaging system 230 may be configured to provide images that confirm, for example, that the port 218 is submerged in a sufficient amount of patient fluid for obtaining a sample through the port 218, and/or that the port 218 is sufficiently near a region of interest (e.g. lesion) for delivering a drug to through the port 218 to the region of interest.

Figure 3:
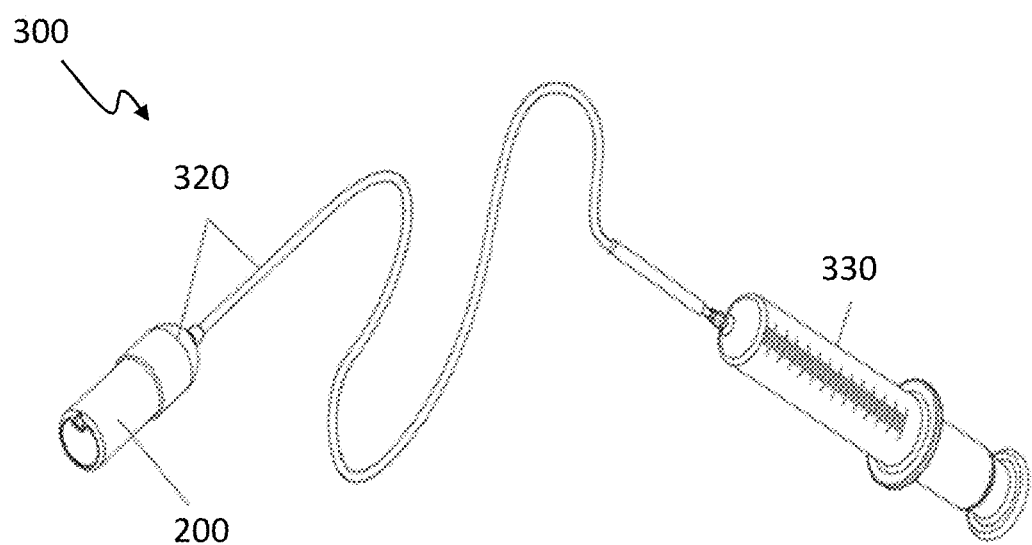
FIG. 3 is an illustrative schematic depicting an exemplary variation of a tethered system including the capsule endoscope variation depicted in FIGS. 2A-2C.

As shown in FIG. 3, in a system 300, the capsule endoscope 200 may be coupled to a tether 320 including a flexible member having a lumen, and the tether 320 may be coupled to a pressure modulator 330 (e.g., pressure source or vacuum source, such as a syringe or pump). The tether 320 may include a lumen, such as in a flexible member, and may be coupled to the capsule endoscope 200 in any suitable manner such as directly (e.g., with epoxy, with a barb fitting or other fitting) or via a clamp, as described in further detail below.

In some variations, the capsule endoscope 200 may include a compartment 216 that is defined separately from the one or more electronics compartments containing the electronics components described above. The compartment 216 may be in fluidic communication between a lumen of the tether 320 and the port 218, so as to enable passage of fluid between the port and a portion of the tether 320 external to the patient (and vice versa). In other words, the compartment 216 may, in combination with the lumen of the tether 320 and the port 218, form a conduit. For example, as shown in FIGS. 2A-2C, the compartment may include an elongated channel that has a proximal end in fluidic communication with the lumen of the tether 320, and a distal end in fluidic communication with the port 218. The elongated channel may extend from a proximal portion of the capsule endoscope to a distal portion of the capsule endoscope. The elongated channel may, for example, terminate at an opening 219 in the rear cover 214 that adjoins with the tether 320. The channel may have a generally circular cross-section, but may alternatively include any suitable cross-sectional shape (e.g., oval or elliptical, etc.). In some variations, at least some components in the one or more electronics compartments may be sized and/or shaped to accommodate cross-sectional area of the channel extending along the capsule endoscope. For example, as shown in FIG. 2C, the circuit boards of the wireless communication module 240, the imaging system 230 and/or the illumination system 220 may be generally crescent-shaped, with crescent-shaped cutouts that accommodate the cross-sectional area of the channel.

In some variations, the capsule endoscope 200 may have a center of gravity that is biased toward the distal end of the capsule endoscope, such that the gravity may tend to help the submersion of the port 218 (located at the distal portion of the capsule endoscope) in pooled fluid for obtaining liquid biopsy. The center of gravity may be adjusted appropriately by, for example, distributing more weight (e.g., magnet, which may be relatively dense) toward the distal end of the capsule endoscope 200. However, the center of gravity may additionally or alternatively be adjusted in other suitable ways, such as a non-uniform distribution of housing material (e.g., thickness of the housing may be greater, or the housing may have a heavier material at a distal end). Additionally or alternatively, a relatively buoyant element or feature (e.g., an air-containing compartment) may be located on an opposing end of the capsule endoscope relative to the port 218.

Figure 4A:
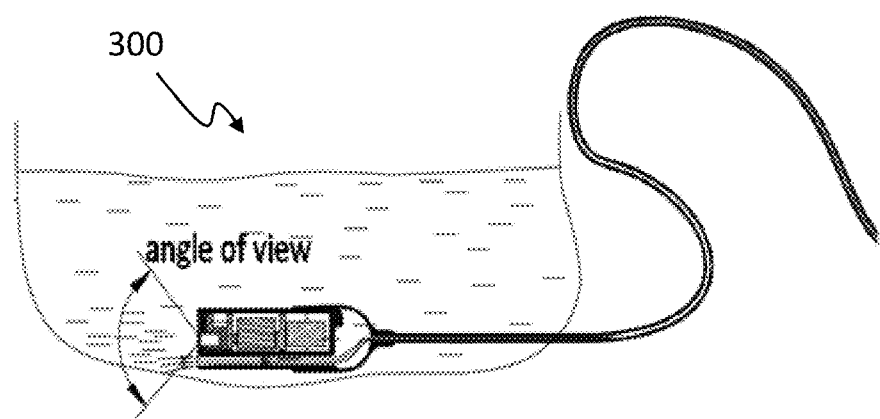
FIG. 4A is an illustrative schematic depicting a method for performing liquid biopsy using the capsule endoscope variation depicted in FIGS. 2A-2C.
Figure 4B:
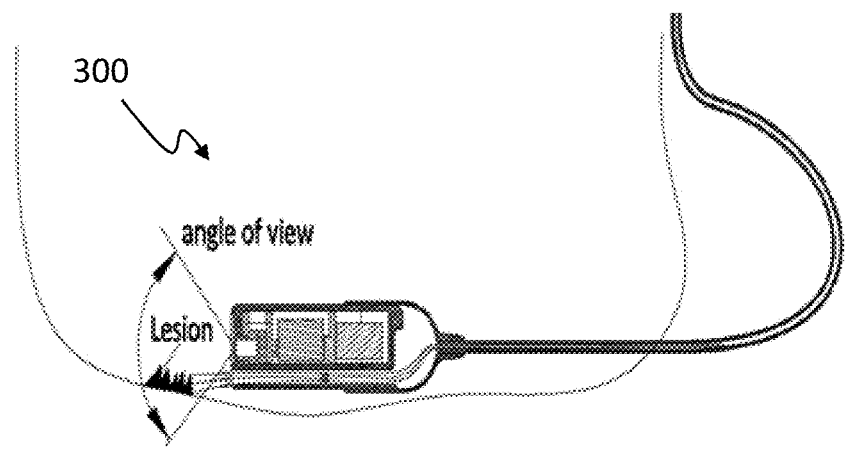
FIG. 4B is an illustrative schematic depicting a method for performing drug delivery using the capsule endoscope depicted in FIGS. 2A-2C.

Exemplary uses of the system 300 are shown in FIGS. 4A and 4B. As shown in FIG. 4A, the system 300 may be advanced to an illustrative fluid environment (in pancreatic juice). The imaging system in the capsule endoscope may be used to observe patient fluid in the field of view of the imaging system, thereby confirming the presence of patient fluid adjacent the port 218. When presence of sufficient patient fluid is determined (e.g., submersion of the port 218 in the patient fluid is determined), a negative pressure provided by the pressure modulator 330 may be formed in the tether 320, the channel, and the port 218. This negative pressure causes the patient fluid to be drawn into the port 218, the channel in the capsule endoscope, the tether 320, and out of the patient into a collection (e.g., syringe).

Additionally, as shown in FIG. 4B, the system 300 may be advanced to a region of interest including a lesion. The imaging system in the capsule endoscope may be used to observe the lesion in the field of view of the imaging system, thereby confirming that the port 218 is sufficiently near the lesion (e.g., the capsule endoscope is in a suitable treatment location and/or orientation). When the treatment location and/or orientation of the capsule endoscope is determined, a drug (e.g., therapeutic agent) may be delivered into the tether 320, and a positive pressure provided by the pressure modulator 330 may be formed in the tether 320, the channel, and the port 218. This positive pressure causes the drug to be urged down the tether, the channel, and the port 218 towards the lesion.

FIGS. 5A-5C depict another exemplary variation of a capsule endoscope 500 including a port 518 at a distal end of the capsule endoscope 500. Except as described below, the capsule endoscope 500 may be similar to the capsule endoscope 200 described above with reference to FIGS. 2A-2D, 3, and 4A-4B, where the endoscope components of the capsule endoscope 500 may be similar to like-numbered endoscope components of the capsule endoscope 200. However, in contrast to the flat distal cover 212 in the capsule endoscope 200, the capsule endoscope 500 may include a transparent domed or bulbous distal cover 512. The domed or bulbous distal cover 512 may, for example, enforce a minimum viewing distance between the lens of the imaging system and the region of interest. By providing a minimum distance along the optical axis of the imaging system between the lens and one or more objects to be viewed, the capsule endoscope may help ensure that the field of view is consistently sufficiently large.

Figure 6A:
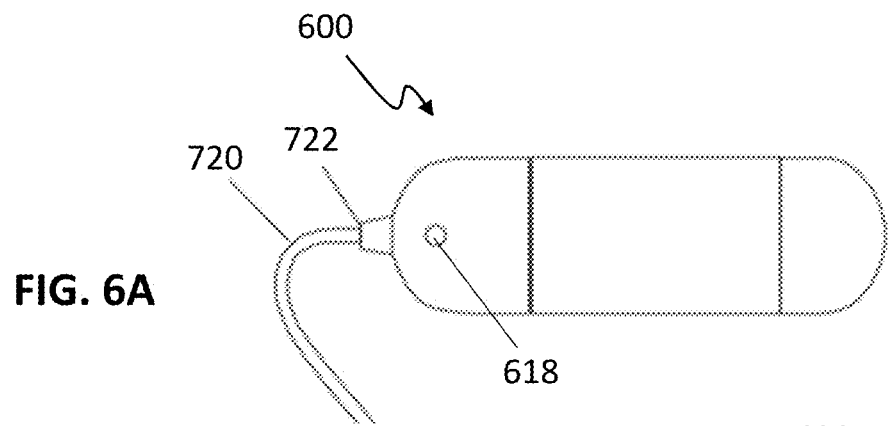
FIGS. 6A-6C are side, partial longitudinal cross-sectional, and longitudinal cross-sectional schematic views, respectively, of an exemplary variation of a capsule endoscope with a port at its proximal portion.
Figure 6B:
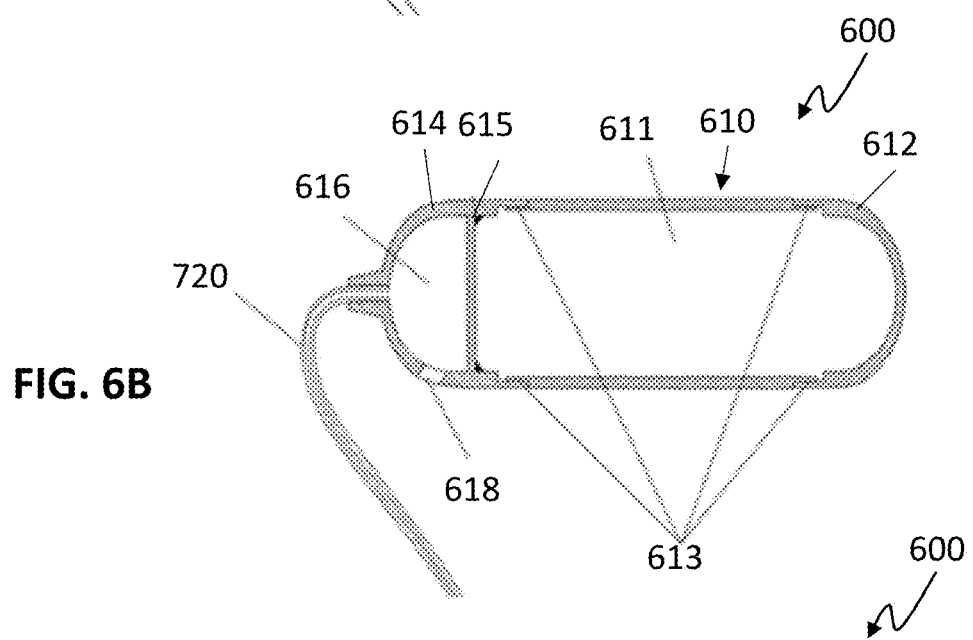
Figure 6C:
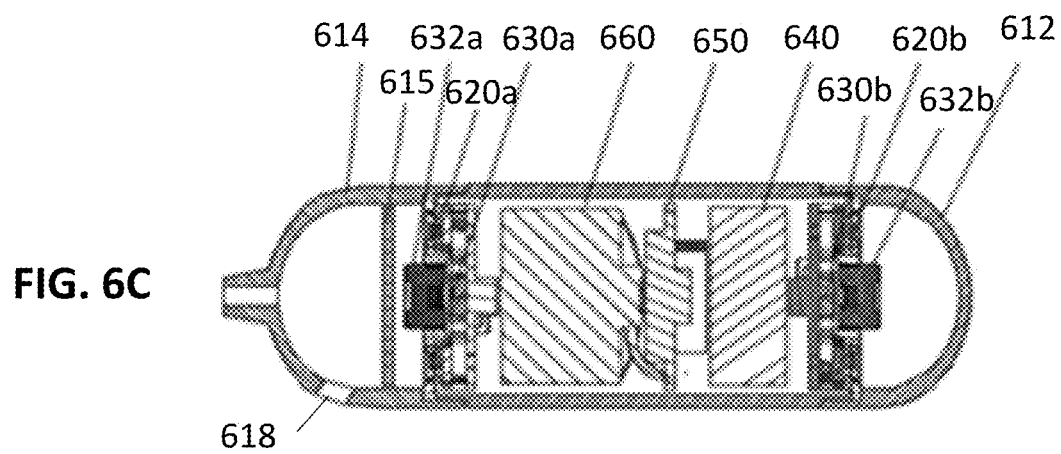

FIGS. 6A-6C depict another exemplary variation of a capsule endoscope 600 including a port 618 at a proximal end of the capsule endoscope 600. Except as described below, the capsule endoscope 600 may be similar to the capsule endoscope 200 described above with reference to FIGS. 2A-2D, 3, and 4A-4B, where the endoscope components of the capsule endoscope 600 may be similar to like-numbered endoscope components of the capsule endoscope 200.

The housing 610 of the capsule endoscope 600 may include a proximal cover 614 and a distal cover 612 coupled to a generally cylindrical structure as shown in FIG. 6B with a fluid-tight seal. The fluid-tight seal may, for example, be formed through the application of epoxy 613 or other adhesive around the adjoining surfaces of the covers and the cylindrical structure. Furthermore, the housing 610 may define an electronics compartment 611 that contains the endoscope components shown in FIG. 6C. The electronics compartment 611 may, for example, be bounded by the generally cylindrical structure and the distal cover 612, as well as an optically transparent proximal wall 615.

Unlike the capsule endoscope 200, the capsule endoscope 600 may include multiple imaging systems and multiple illumination systems. For example, as shown in FIG. 6C, the capsule endoscope 600 may include a proximal imaging system 630a and a proximal illumination system 620a that are arranged at a proximal end of the capsule endoscope 600 to view and illuminate a field of view adjacent to the proximal end of the capsule endoscope 600. The capsule endoscope 600 may additionally include a distal imaging system 630b and a distal illumination system 620b that are arranged at a distal end of the capsule endoscope 600 to view and illuminate a field of view adjacent to the distal end of the capsule endoscope 600. Although two imaging systems are depicted in the variation shown in FIG. 6C, it should be understood that in some variations only one imaging system may be included in the capsule endoscope 600 (e.g., at the proximal end of the capsule endoscope 600, near the port 618).

Furthermore, unlike the capsule endoscope 200, the capsule endoscope 600 may include a compartment 616 including a chamber as shown in FIGS. 6B and 6C. The chamber may be located in a proximal portion of the capsule endoscope. Like the compartment 216 described above, the compartment 616 may be in fluidic communication between a lumen in the tether 720 and the port 618, so as to provide a conduit for liquid biopsy and/or drug delivery. The compartment 616 may include a chamber, where a sidewall or other surface of the chamber may define the port 618. As shown in FIG. 6B, in some variations the chamber may be bound at least in part by the transparent proximal wall 615 and the proximal cover 614.

Figure 7:
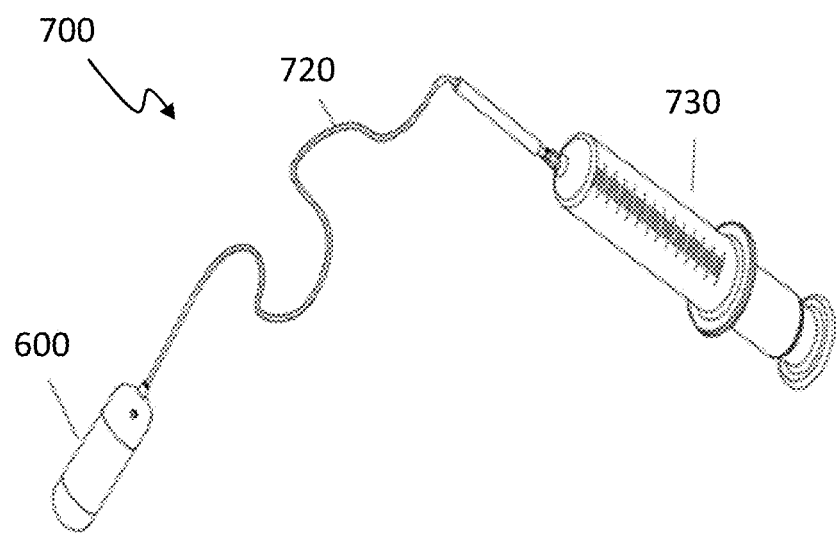
FIG. 7 is an illustrative schematic depicting an exemplary tethered system including the capsule endoscope variation depicted in FIGS. 6A-6C.

As shown in FIG. 7, in a system 700, the capsule endoscope 600 may be coupled to a tether 720 including a flexible member having a lumen, and the tether 720 may be coupled to a pressure modulator 730 (e.g., pressure source or vacuum source, such as a syringe or pump). The tether 720 may include a lumen, such as in a flexible member, and may be coupled to the capsule endoscope 600 in any suitable manner such as directly (e.g., with epoxy 722 as shown in FIG. 6A, with a barb fitting or other fitting) or via a clamp, as described in further detail below.

Figure 8A:
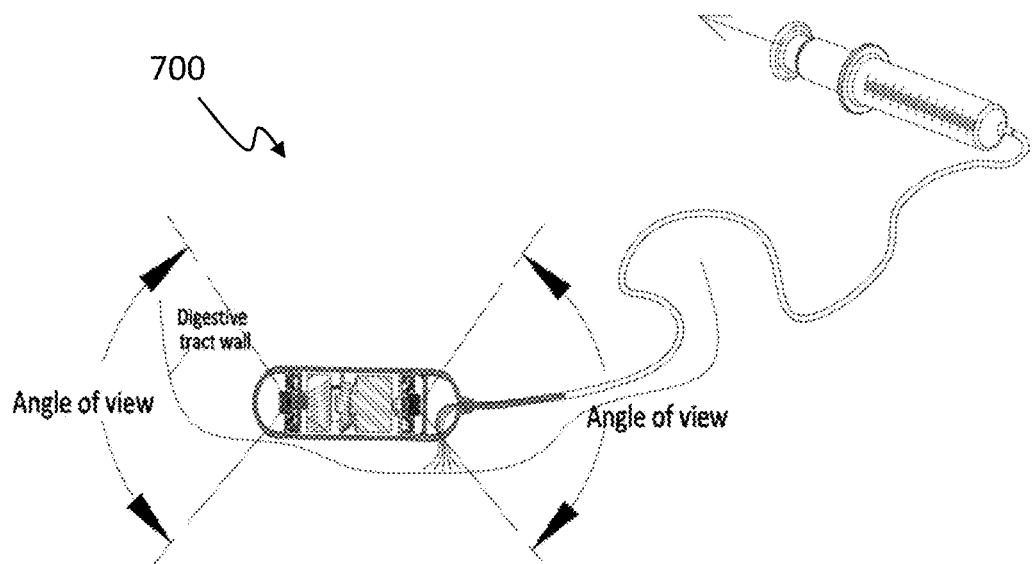
FIG. 8A is an illustrative schematic depicting a method for performing liquid biopsy using the capsule endoscope variation depicted in FIGS. 6A-6C.
Figure 8B:
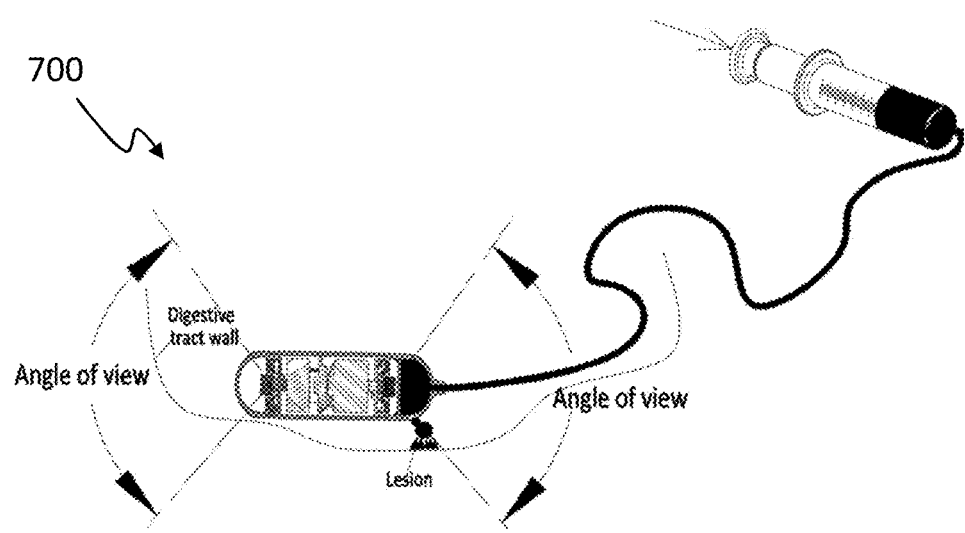
FIG. 8B is an illustrative schematic depicting a method for performing drug delivery using the capsule endoscope variation depicted in FIGS. 6A-6C.

Exemplary uses of the system 700 are shown in FIGS. 8A and 8B. As shown in FIG. 8A, the system 700 may be advanced to an illustrative fluid environment (e.g., in pancreatic juice). One or more imaging systems in the capsule endoscope may be used to help navigate the capsule endoscope to the region of interest and/or may be used to observe patient fluid. For example, a distal (front) imaging system may be primarily used to help position and/or orient the capsule endoscope to and near the region of interest, while a proximal (rear) imaging system near the port 618 may be used to assess the position of the port 618 relative to any patient fluid (and assess the presence of sufficient patient fluid). As another example, in variations in which the capsule endoscope has only a proximal imaging system near a proximal port 618, the proximal imaging system may be used to help general positioning and/or orientating of the capsule endoscope to the region of interest, as well as assess the position of the port relative to any patient fluid and assess the presence of sufficient patient fluid. When presence of sufficient patient fluid is determined (e.g., submersion of the port in the patient fluid is determined), a negative pressure provided by the pressure modulator 730 may be formed in the tether 720, the compartment 616, and the port 618. This negative pressure causes the patient fluid to be drawn into the port 618, the compartment 616 in the capsule endoscope, the tether 720, and out of the patient into a collection (e.g., syringe).

Additionally, as shown in FIG. 8B, the system 700 may be advanced to a region of interest including a lesion. Similarly to that described above with reference to FIG. 8A, one or more imaging systems in the capsule endoscope may be used to help navigate the capsule endoscope to the region of interest and/or may be used to observe a region of interest (e.g., lesion). In other words, the one or more imaging systems may be used to help confirm when the port 618 is proximate a region of interest for treatment (e.g., the capsule endoscope is in a suitable treatment location and/or orientation). When the treatment location and/or orientation of the capsule endoscope is determined, a drug (e.g., therapeutic agent) may be delivered into the tether 720, and a positive pressure provided by the pressure modulator 730 may be formed in the tether 720, the compartment 616, and the port 618. This positive pressure causes the drug to be urged down the tether, the compartment 616, and the port 618 towards the lesion.

Figure 9:
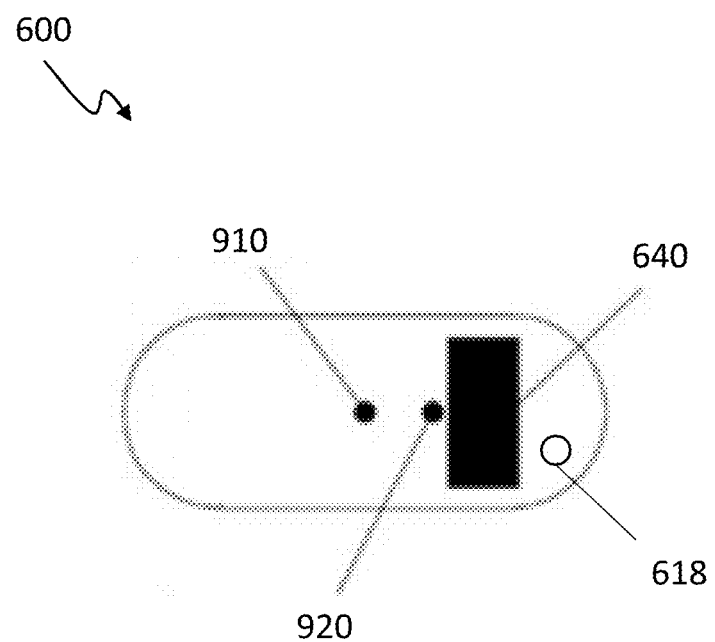
FIG. 9 is an illustrative schematic depicting an exemplary variation of a capsule endoscope having a biased center of gravity.

In some variations, as shown in FIG. 9, the capsule endoscope 600 may have a center of gravity 920 that is biased toward the proximal end of the capsule endoscope, such that the gravity may tend to help the submersion of the port 618 (located at the proximal portion of the capsule endoscope) in pooled fluid for obtaining liquid biopsy. As shown in FIG. 9, the center of gravity 920 may be axially offset from the centroid 910 (toward the proximal end of the capsule endoscope 600). The center of gravity may be adjusted appropriately by, for example, distributing more weight (e.g., magnet 640, which may be relatively dense) toward the proximal end of the capsule endoscope 600. However, the center of gravity may additionally or alternatively be adjusted in other suitable ways, such as a non-uniform distribution of housing material (e.g., thickness of the housing may be greater, or the housing may have a heavier material at a proximal end). Additionally or alternatively, a relatively buoyant element or feature (e.g., an air-containing compartment) may be located on an opposing end of the capsule endoscope relative to the port 618.

Tether

Generally, the tether functions to help retain the capsule endoscope in a desired region of interest (e.g., avoid reduced dwell times in the esophagus due to peristalsis, etc.) and provide a conduit for carrying a fluid from and/or to the capsule endoscope, such as a liquid biopsy from the capsule endoscope or a drug to the capsule endoscope. As described above, a proximal portion of the tether may extend to outside the patient and may be coupled to a pressure modulator (e.g. pressure source or vacuum source) to control fluid flow through tether through positive pressure or negative pressure. The proximal portion of the tether may further be coupled to a collection unit (e.g., syringe, other container) for collecting fluid withdrawn from the patient through the tether, and/or to a drug source (e.g., syringe, other container) for delivering into the patient through the tether. In some variations, the proximal portion may be branched and include one end coupled to a vacuum source (and/or a drug source) and another end coupled to a pressure source (and/or a collection unit). In some of these variations, one or more valves or other fluidic control system to switch between introducing a negative pressure and a positive pressure in the tether.

The tether may be removably coupled to the capsule endoscope. For example, the tether may be coupled to the capsule endoscope so as to follow the capsule endoscope (e.g., down a patient's gastrointestinal tract) as the capsule endoscope is advanced in the patient. Furthermore, the tether may be uncoupled from the capsule endoscope to allow the capsule endoscope to pass through the patient (e.g., naturally, such as through peristalsis) and then withdrawn from the patient. In some variations, a port for taking a liquid biopsy and/or delivering a drug may be located on a portion of the tether. Alternatively, the tether may be withdrawn from the patient, with the capsule endoscope remaining coupled to the tether, in order to remove the capsule endoscope from the patient.

As shown in FIGS. 10A and 10B, in some variations a tether 1000 may include a flexible member having a lumen 1010. Generally, the flexible member may be an elongated tubular member configured to be advanced safely and comfortably into a patient's body cavity. In some variations, the flexible member may be between about 2 mm to about 10 mm in length, or 9 mm in length. The flexible member may include a soft, flexible material such as silicone elastomer (e.g., having a Shore A hardness of between about 35 and about 65, or about 50). Furthermore, in an exemplary variation the flexible member may have an inner diameter of about 0.5 mm (between about 0.4 mm and about 0.6 mm, for example), and an outer diameter of about 1 mm (between about 0.9 mm and about 1.3 mm, for example), with a wall thickness of about 0.25 mm. However, in other variations the flexible member may include other combinations of length, material types and/or dimensions.

Various exemplary variations of the tether having different arrangements of tether components are described in further detail below.

FIGS. 11A-11D depict an exemplary variation of a tether 1120 including a flexible member 1122 and a clamp 1124 for coupling the flexible member 1122 to a capsule endoscope, where the clamp 1124 includes a port 1128 in fluidic communication with a lumen of the flexible member 1122. Furthermore, the clamp 1124 may be suitable for a "double lens" capsule endoscope having both a proximal imaging system on a proximal end of the capsule endoscope, and a distal imaging system on a distal end of the capsule endoscope.

Figure 11A:
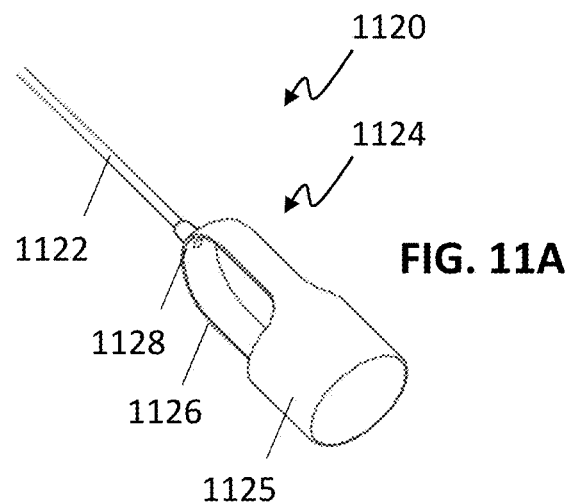
FIG. 11A is an illustrative schematic depicting an exemplary variation of a tether with a clamp having a port.
Figure 11B:
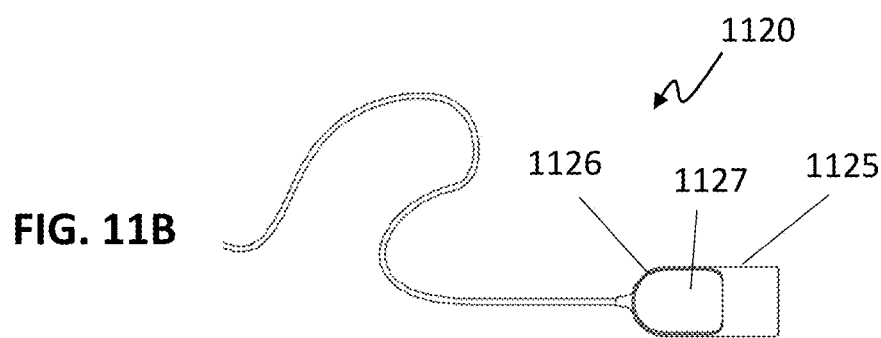
FIG. 11B is an illustrative schematic depicting a side view of the exemplary tether variation depicted in FIG. 11A.
Figure 11C:
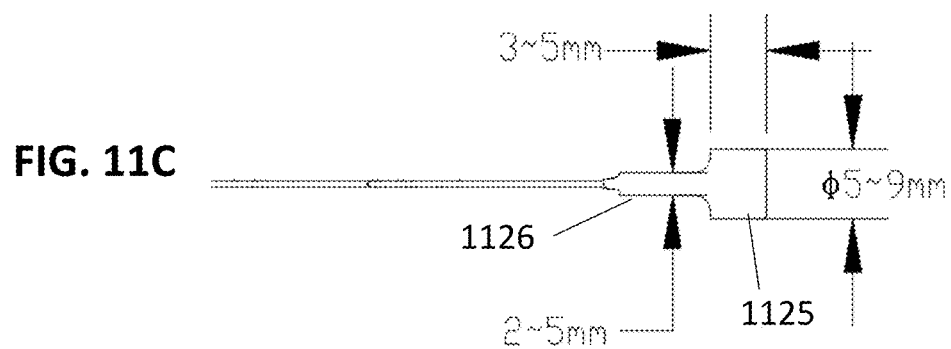
FIG. 11C is an illustrative schematic depicting exemplary dimension ranges of the exemplary tether variation depicted in FIG. 11A.
Figure 11D:
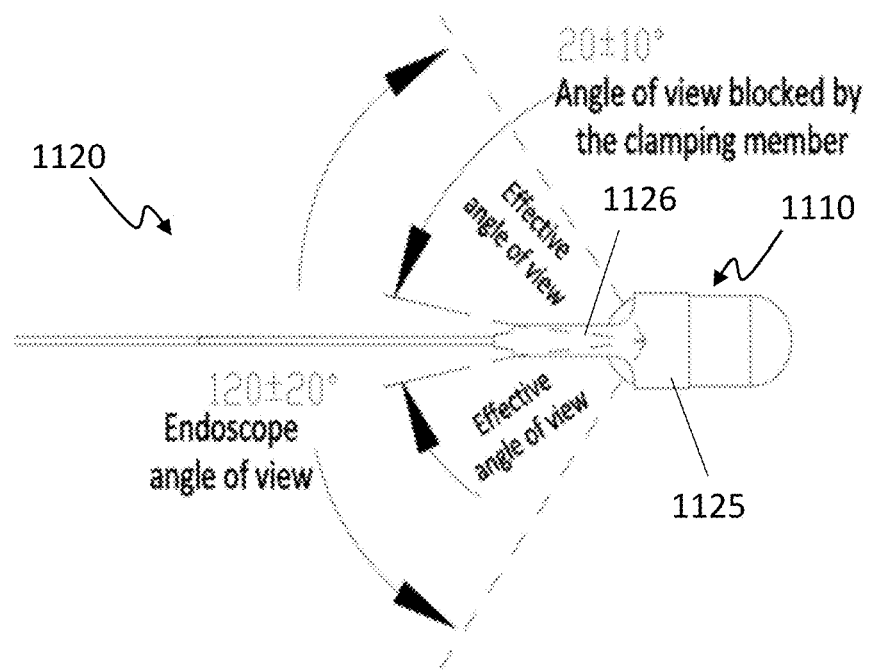
FIG. 11D is an illustrative schematic depicting ranges of field of view in a system incorporating the exemplary tether variation depicted in FIG. 11A.

As shown in FIG. 11D, the clamp 1124 may include a sheath 1125 that is configured to at least partially surround and attach to at least a portion of the capsule endoscope 1110, thereby coupling the tether 1120 to the capsule endoscope 1110. The sheath 1125 may include open proximal and distal ends, where the open proximal end forms a window providing visual clearance (i.e., does not significantly obstruct) a proximal imaging system on the proximal end of the capsule endoscope. As shown in FIG. 11A, the sheath 1125 may surround an entire circumference of a proximal portion of the capsule endoscope 1110. However, in other variations the sheath may not surround an entire circumference; for example, the sheath may have a "C"-shaped cross-sectional shape.

The clamp may further include an anchor member 1126 configured to couple the clamp to the flexible member. The anchor member 1126 may be integrally formed with the sheath 1125 or formed separately and coupled to the sheath 1125 with one or more suitable fasteners and/or mechanical fittings, etc. Furthermore, the anchor member 1126 may be coupled to a distal end of the flexible member 1122, such as by a mechanical fitting and/or epoxy. Alternatively, the anchor member 1126 may be integrally formed with a distal end of the flexible member 1112, such as through an injection molding process or the like.

As shown in FIG. 11B, the anchor member 1126 may be generally arcuately shaped (e.g., "C"-shaped or "U"-shaped) to enable coupling of the clamp and the flexible member at a location that is offset from the capsule endoscope, so as to not significantly block the field of view of the proximal imaging system of the capsule endoscope. For example, as shown in FIG. 11B, the anchor member 1126 may provide a window region 1127 that, together with the open proximal end of the sheath 1125, may allow for a substantial portion of the field of view of the proximal imaging system to remain unobscured. Furthermore, as shown in FIG. 11C, the side profile of the anchor member 1126 may be smaller than the diameter of the sheath 1125. Overall, as shown in FIG. 11D, the clamp 1124 may provide for an effective (unobscured) field of view of the proximal imaging system that is not significantly smaller or narrower than the field of view without the clamp 1124 attached. For example, FIG. 11C illustrates exemplary dimensions for the clamp 1124, including a sheath diameter of between about 5 mm and about 9 mm, a sheath length between about 3 mm and about 5 mm, and an anchor member width of between about 2 mm and 5 mm. As shown in FIG. 11D, when combined with a clamp 1124 of these dimension ranges, an endoscope field of view having an angle of view of about 120 degrees (e.g., between about 100 degrees and about 140 degrees) may only be reduced by about 20 degrees (e.g., between about 10 degrees and about 30 degrees). Thus, the resulting effective field of view remains substantially unobscured by the clamp 1124.

In some variations, the anchor member 1126 may include a single component forming an arcuate structure that extends across an opening of the sheath (i.e., arcuate segments that are integrally formed). However, alternatively, the anchor member may include multiple components each forming a separate segment of such an arcuate structure. For example, in some variations, the anchor member 1126 may include two or more separate arcuate segments that connect end-to-end (or longitudinally overlap) to form a single arcuate structure similar to the anchor member 1126 shown in FIG. 11A. For example, an anchor member 1126 may include two opposing arcuate segments that extend from opposite sides of a proximal end of the sheath 1125 towards the apex of the anchor member 1126. These two opposing arcuate segments may be of approximately equal length and meet at the apex of the anchor member 1126 (e.g., near the port 1128), or may be of unequal length and meet on either side of the anchor member 1126.

Figure 11E:
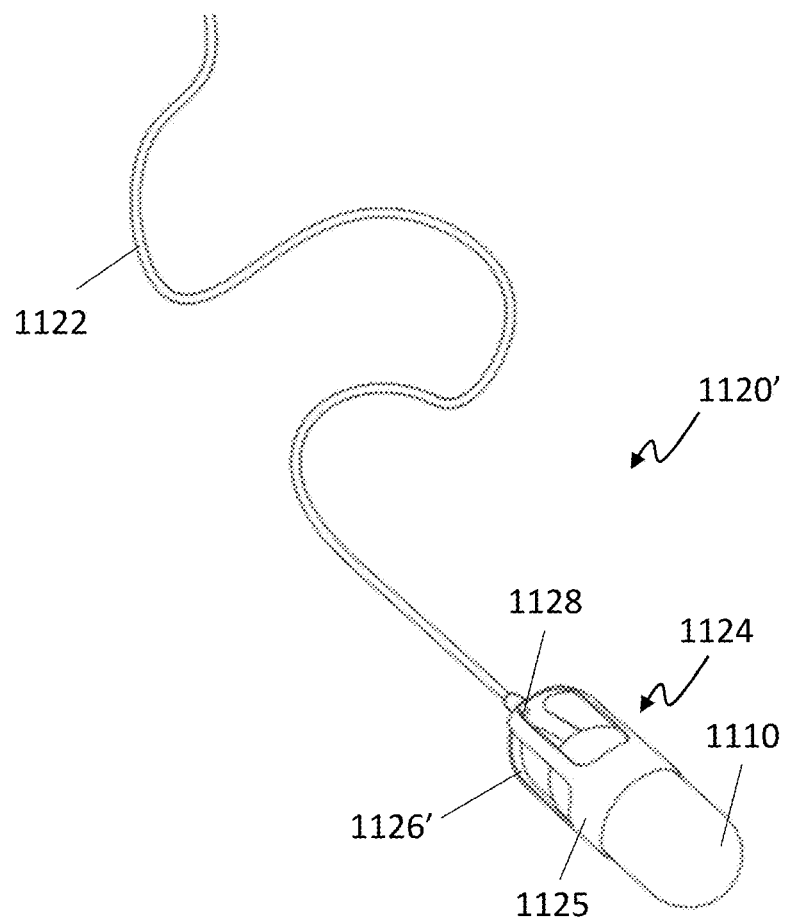
FIG. 11E is an illustrative schematic depicting an exemplary variation of a tether with a clamp having an anchor member with multiple arcuate structures.

Furthermore, in some variations, the anchor member may include multiple arcuate structures oriented in different planes (e.g., forming a dome shape with multiple window regions). For example, FIG. 11E depicts a tether 1120' including an anchor member 1126' having four arcuate segments that are oriented in orthogonal planes (i.e., arcuate segments distributed approximately 90 degrees circumferentially around the anchor member 1126' and the sheath 1125) and form multiple window regions. The arcuate segments may be equally distributed around the anchor member 1126' and the sheath 1125 (e.g., such that the anchor member 1126' is generally radially symmetrical), or alternatively may be unequally distributed. In some variations, additional arcuate segments may, for example, improve structural integrity of the anchor member (e.g., multi-directional and/or torsional rigidity). Furthermore, additional arcuate segments distributed around the anchor member 1126' and the sheath 1125 (e.g., when equally distributed) may help improve balance of forces when the tether is attached to and interacting with (e.g., pulling) the capsule endoscope. It should be understood that other variations of the tether similar to tethers 1120 and 1120' may include any suitable number of arcuate segments (e.g., 3, 5 or more, etc.). The width of the arcuate segments may decrease with increasing numbers of arcuate segments, so as to maintain a sufficiently unobscured field of view for the capsule endoscope imaging system.

The anchor member 1126 may further include a port 1128 in fluidic communication with the lumen of the flexible member. The port 1128 may be an opening that is configured to be axially offset from the proximal portion of the capsule endoscope, such as opposite the proximal imaging system, such that the proximal imaging system may view the environment around the port 1128 (e.g., to confirm the presence of sufficient patient fluid near the port 1128 for withdrawal of patient fluid through the port, to confirm location of a region of interest relative to the port 1128 for receiving a drug through the port, etc.).

Figure 12:
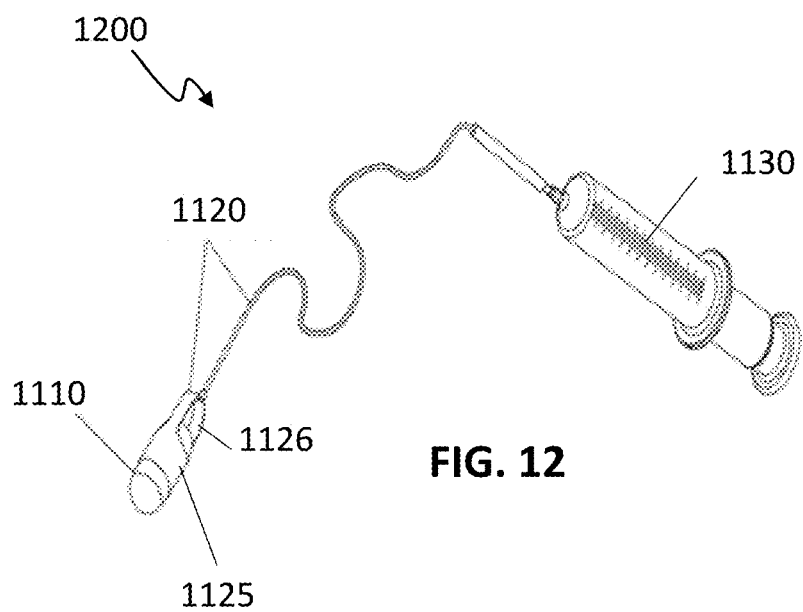
FIG. 12 is an illustrative schematic depicting an exemplary variation of a tethered system including the tether variation depicted in FIG. 11A.

For example, as shown in FIG. 12, in a system 1200, the capsule endoscope 1110 may be coupled to a tether 1120 via a clamp 1125. The capsule endoscope 1110 may, for example, be similar to the capsule endoscope 600 described above with reference to FIGS. 6A-6C having proximal and distal imaging systems, except that the capsule endoscope 1110 may omit a port. The tether 1120 may be coupled to a pressure modulator 1130 (e.g., pressure source or vacuum source, such as a syringe or pump). The tether 1120 may include a lumen, such as in a flexible member, and the clamp 1125 may include a port in fluidic communication with the lumen.

Figure 13A:
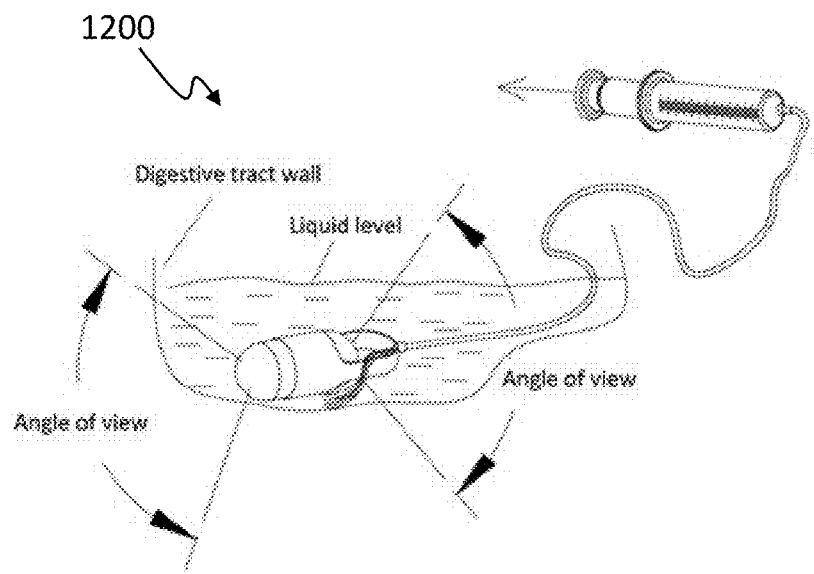
FIG. 13A is an illustrative schematic depicting a method for performing liquid biopsy using the tether variation depicted in FIG. 11A.
Figure 13B:
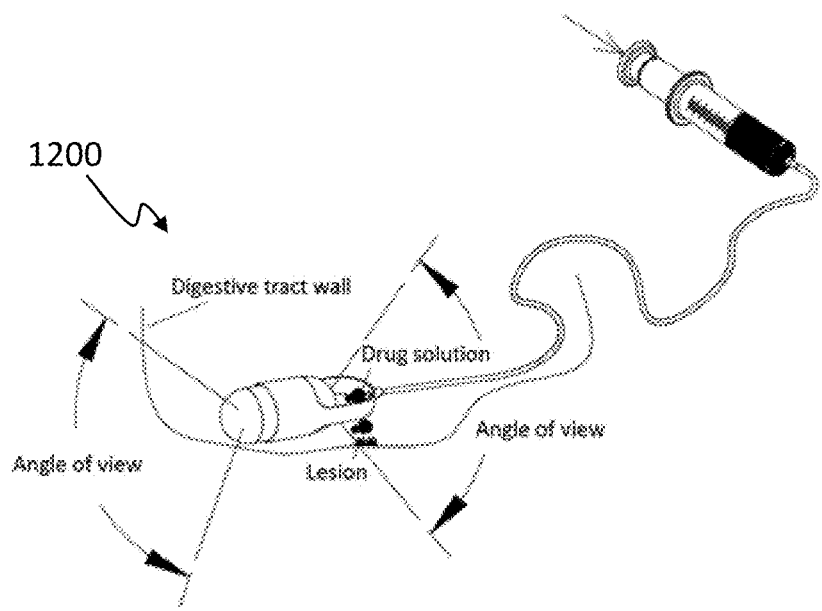
FIG. 13B is an illustrative schematic depicting a method for performing drug delivery using the tether variation depicted in FIG. 11A.

Exemplary uses of the system 1200 are shown in FIGS. 13A and 13B. As shown in FIG. 13A, the system 1200 may be advanced to an illustrative fluid environment (e.g., in pancreatic juice). The distal imaging system and/or proximal imaging system in the capsule endoscope may be used to observe patient fluid in the surroundings of the capsule endoscope, thereby confirming the presence of patient fluid adjacent the port 1128. When presence of sufficient patient fluid is determined (e.g., submersion of the port 1128 in the patient fluid is determined), a negative pressure provided by the pressure modulator 1130 may be formed in the tether 1120 and in the port 1128. This negative pressure causes the patient fluid to be drawn into the port 1128, the tether 1120, and out of the patient into a collection (e.g., syringe).

Additionally, as shown in FIG. 13B, the system 1200 may be advanced to a region of interest including a lesion. The distal imaging system and/or proximal imaging system in the capsule endoscope may be used to observe the lesion, thereby confirming that the port 1128 is sufficiently near the lesion (e.g., the capsule endoscope is in a suitable treatment location and/or orientation). When the treatment location and/or orientation of the capsule endoscope is determined, a drug (e.g., a therapeutic agent) may be delivered into the tether 1120, and a positive pressure provided by the pressure modulator 1130 may be formed in the tether 1120 and the port 1128. This positive pressure causes the drug to be urged down the tether and out of the port toward the lesion.

Figure 14A:
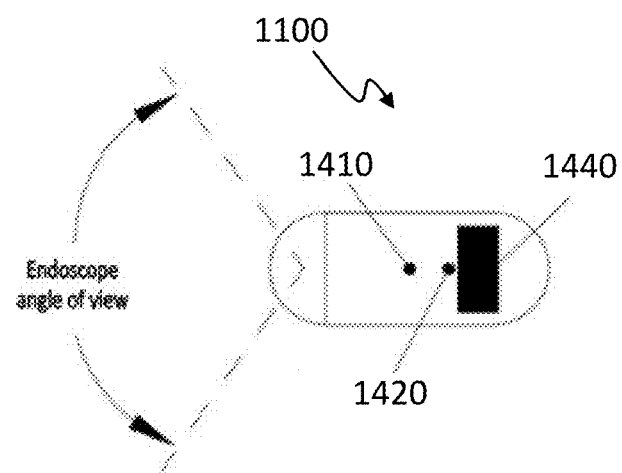
FIG. 14A is an illustrative schematic depicting an exemplary variation of a capsule endoscope having a biased center of gravity.
Figure 14B:
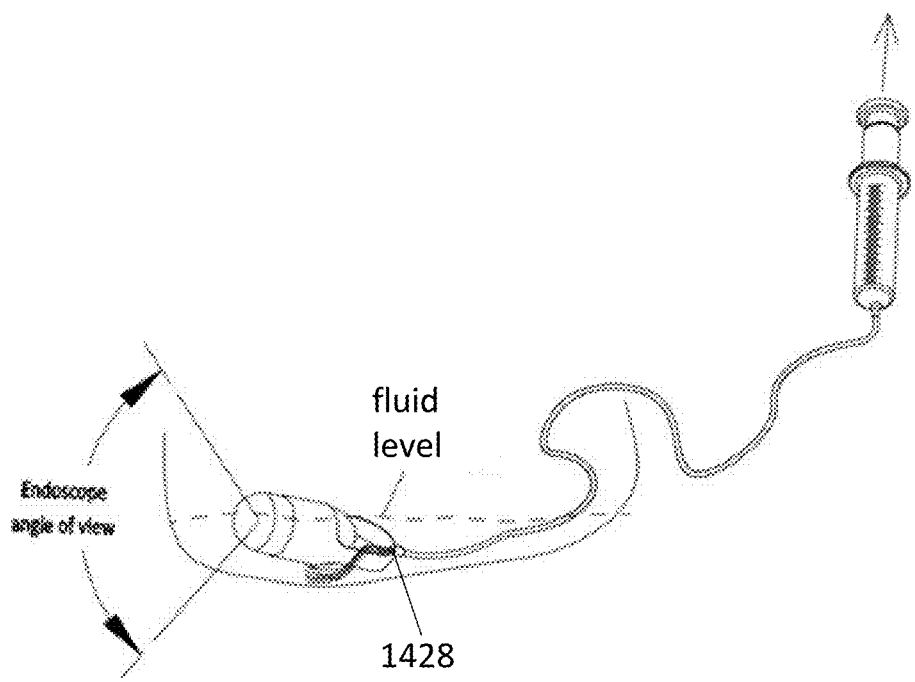
FIG. 14B is an illustrative schematic depicting the capsule endoscope variation depicted in FIG. 14A in combination with the tether variation depicted in FIG. 11A.

In some variations, as shown in FIGS. 14A and 14B, the capsule endoscope 1100 may have a center of gravity 1420 that is biased toward the proximal end of the capsule endoscope, such that the gravity may tend to help the submersion of the port 1428 (located in the tether coupled to a proximal end of the capsule endoscope 1110) in pooled fluid for obtaining liquid biopsy. As shown in FIG. 14A, the center of gravity 1420 may be axially offset from the centroid 1410 (toward the proximal end of the capsule endoscope 1100). The center of gravity may be adjusted appropriately by, for example, distributing more weight (e.g., magnet 1440, which may be relatively dense) toward the proximal end of the capsule endoscope 1100. However, the center of gravity may additionally or alternatively be adjusted in other suitable ways, such as a non-uniform distribution of housing material (e.g., thickness of the housing may be greater, or the housing may have a heavier material at a proximal end). Additionally or alternatively, a relatively buoyant element or feature (e.g., an air-containing compartment) may be located on an opposing end of the capsule endoscope relative to the port 1428.

Figure 15A:
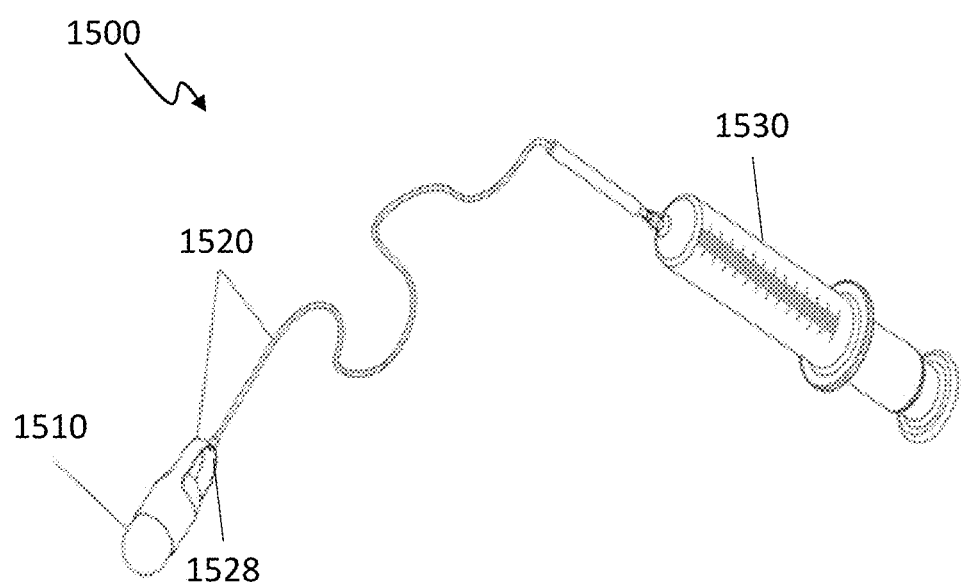
FIG. 15A is an illustrative schematic depicting another exemplary variation of a tethered system including the tether variation depicted in FIG. 11A.
Figure 15B:
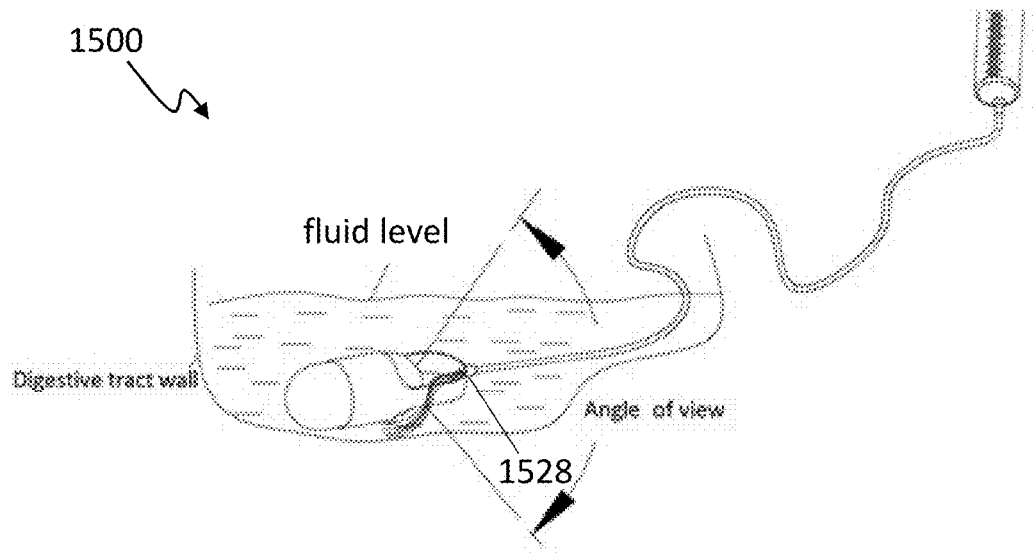
FIG. 15B is an illustrative schematic depicting a method for performing liquid biopsy using the tethered system variation depicted in FIG. 15A.
Figure 15C:
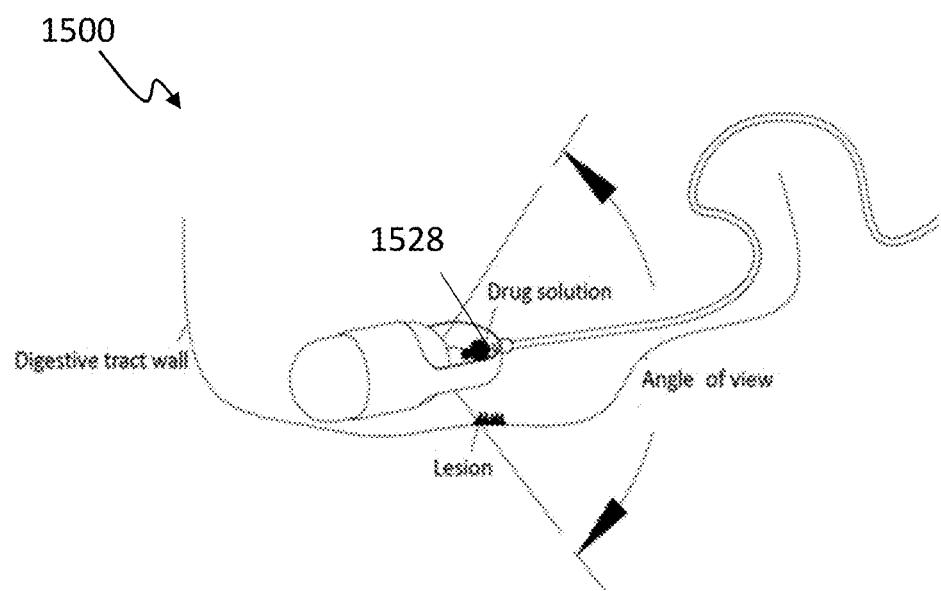
FIG. 15C is an illustrative schematic depicting a method for performing drug delivery using the tethered system variation depicted in FIG. 15A.

FIGS. 15A-15C depict a system 1500 including another exemplary variation of a tether 1520 including a flexible member and a clamp for coupling the flexible member to a capsule endoscope 1510, where the clamp includes a port 1528 in fluidic communication with a lumen of the flexible member. The system 1500 may be similar to the system 1200 described above with reference to FIGS. 12, 13A-13B, and 14A-14B, except as described below. In the system 1500, the clamp may be suitable for a "single lens" capsule endoscope having only a proximal imaging system on a proximal end of the capsule endoscope. As shown in FIG. 15B, the proximal imaging system in the capsule endoscope may have a field of view not substantially obscured by the clamp of the tether, including the surroundings of the port 1528. Accordingly, when presence of sufficient patient fluid is determined, a negative pressure provided by the pressure modulator 1530 may be formed in the tether 1520 and in the port 1528. This negative pressure causes the patient fluid to be drawn into the port 1528, the tether 1520, and out of the patient into a collection (e.g., syringe). Similarly, as shown in FIG. 15C, the proximal imaging system in the capsule endoscope may be used to determine whether the port 1528 is sufficiently near a lesion. When a treatment location and/or orientation of the capsule endoscope is determined, a drug may be delivered into the tether 1528, and a positive pressure provided by the pressure modulator 1530 may be formed in the tether 1520 and the port 1528. This positive pressure causes the drug to be urged down the tether and out of the port toward the lesion.

Figure 16A:
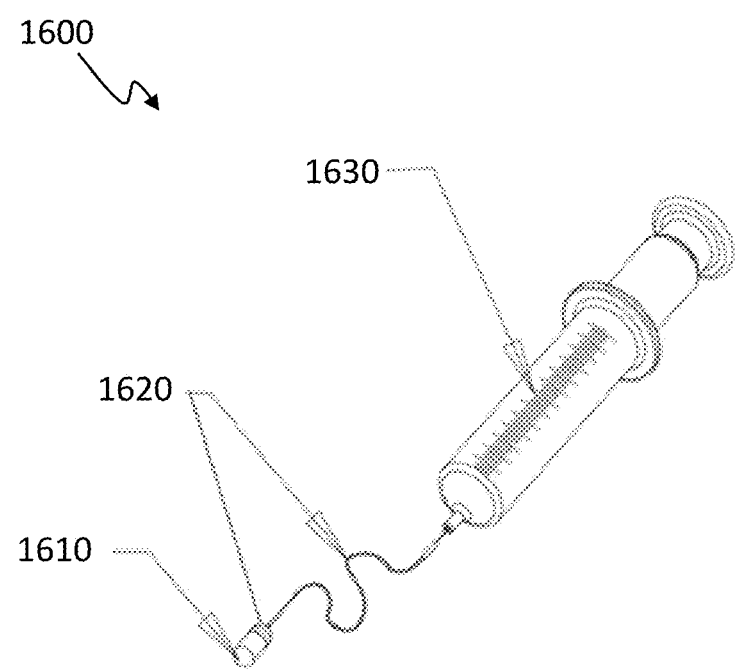
FIG. 16A is an illustrative schematic depicting another exemplary variation of a tethered system including a tether with a suction cup.
Figure 16B:
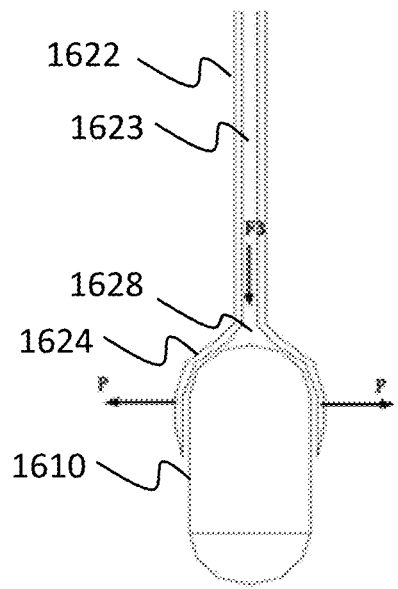
FIG. 16B is a force diagram illustrating disengagement between the capsule endoscope and the tether depicted in FIG. 16A.

As shown in FIGS. 16A and 16B, in some variations, a tether 1620 may include a port that is configured to permit passage of fluid therethrough after separation from the capsule endoscope. As shown in FIG. 16A, a tethered system 1600 may include a tether 1620 releasably coupled to a capsule endoscope 1610 and to a pressure modulator 1630 (e.g., syringe or pump). As shown in FIG. 16B, similar to the tether variations described above, the tether 1620 may include a flexible member 1622 having a lumen 1623. However, in this variation, the tether 1620 may include a port 1628 in fluidic communication with the lumen 1623 and which opens to a suction cup 1624 for receiving the capsule endoscope 1610. The suction cup 1624 may be soft and flexible, and may be formed, for example, out of the same or similar material as the flexible member 1622 (e.g., silicone). In some variations, the internal shape of the suction cup 1624 may be smooth and generally complementary (e.g., correspond) to the shape of the external housing of the capsule endoscope 1610.

Figure 16C:
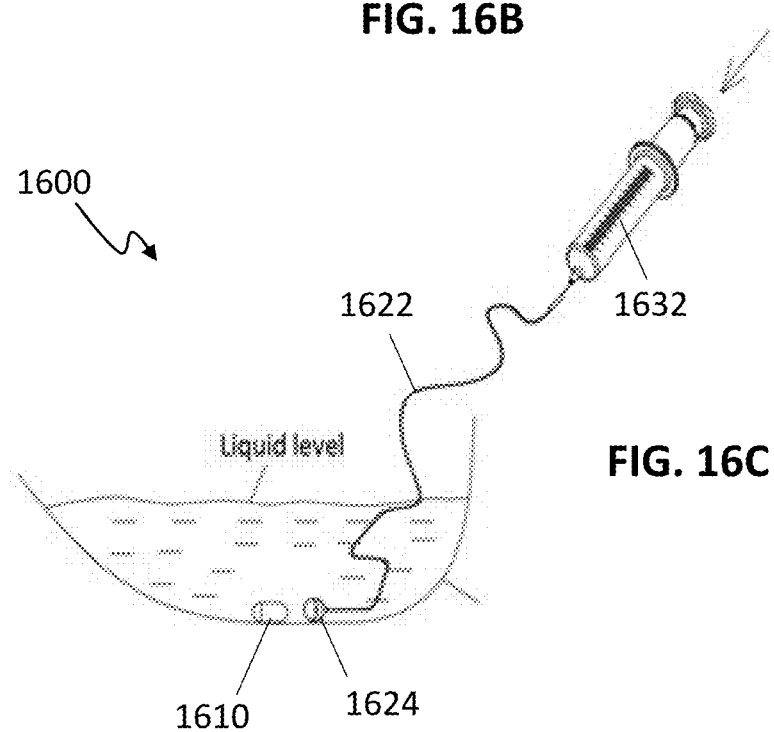
FIG. 16C is an illustrative schematic depicting disengagement of the capsule endoscope and the tether depicted in FIG. 16A.

Generally, a vacuum state within the lumen 1623 retains the capsule endoscope 1610 within the suction cup 1624. As shown in FIG. 16B, pressurization within the lumen 1623 (e.g., inflation via a coupled pressure source), the suction cup 1624 may expand radially outward as shown by the arrows P, and/or an axial pushing force F3 may provide thrust against the capsule endoscope 1610, thereby releasing the capsule endoscope 1610 from the suction cup 1624. FIG. 16C illustrates an exemplary method of decoupling the capsule endoscope 1610 from the suction cup 1624. In this variation, a conduit may extend from a pressure source (syringe 1632), through a lumen of the flexible member 1622, and through a port leading to a suction cup 1624. When the pressure source provides positive pressure in the conduit (e.g., by depressing the plunger on syringe 1632), the expansion of the suction cup 1624 and/or the pushing force through the conduit may cause the suction cup 1624 to disengage, thereby releasing the capsule endoscope 1610. After the release of the capsule endoscope 1610, the port 1628 may be free to permit the exchange of fluid between the lumen of the flexible member 1622 and the environment in which the port 1628 is placed.

Figure 17A:
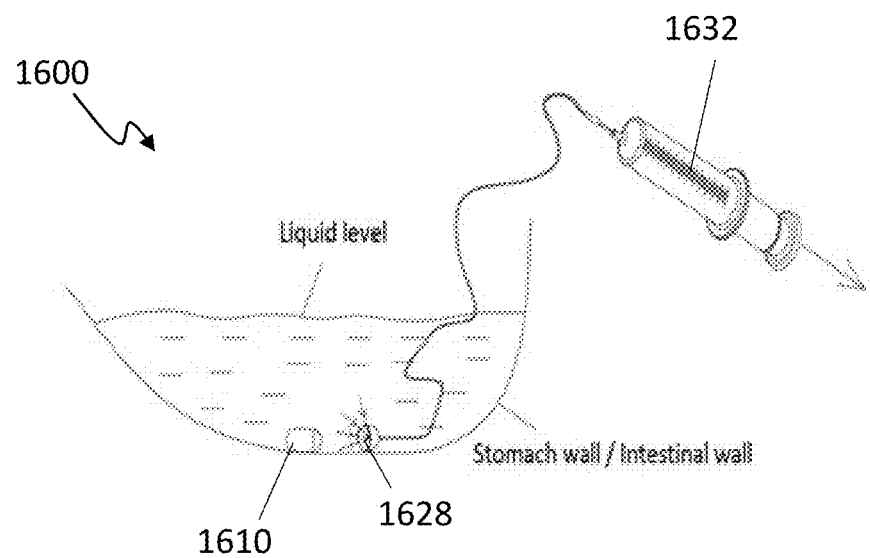
FIG. 17A is an illustrative schematic depicting a method for performing liquid biopsy using the tethered system variation depicted in FIG. 16A.

Such disengagement between the capsule endoscope and the tether may, for example, occur at a region of interest where it may be desirable to obtain a biopsy of patient fluid and/or deliver drugs through the port. As shown in FIG. 17A, the system 1600 may be advanced to an illustrative fluid environment (e.g., in pancreatic juice). One or more imaging systems in the capsule endoscope may be used to help navigate the capsule endoscope to the region of interest and/or may be used to observe patient fluid. When presence of sufficient patient fluid is determined, the capsule endoscope may be disengaged from the tether as described above. Thereafter, a negative pressure provided by the pressure modulator (e.g., syringe 1632) may be formed in the tether and the port 1628. This negative pressure causes the patient fluid to be drawn into the port 1628, into the tether, and out of the patient into a collection (e.g., syringe). Furthermore, the now-detached capsule endoscope 1610 may be controlled (e.g., via an external magnetic control system as described below) such that its imaging system(s) observe the biopsy process and enable confirmation that a sample was appropriately obtained.

Figure 17B:
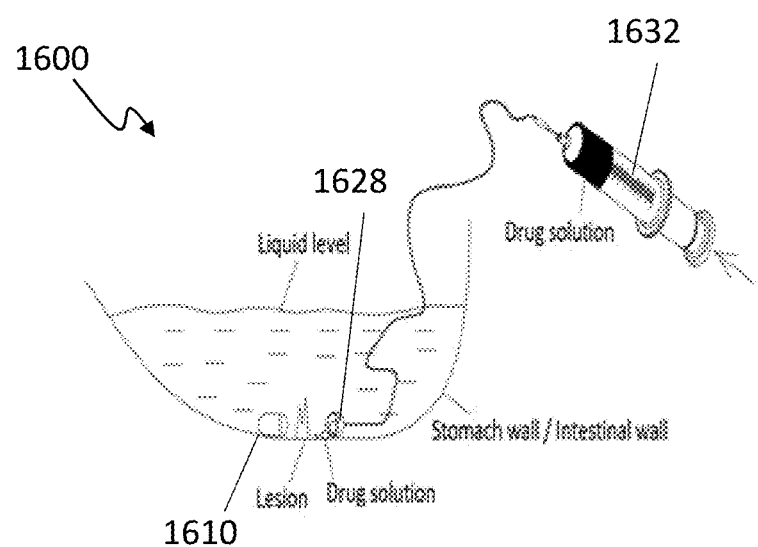
FIG. 17B is an illustrative schematic depicting a method for performing drug delivery using the tethered system variation depicted in FIG. 17A.

As another example, as shown in FIG. 17B, the system 1600 may be advanced to a region of interest including a lesion. Similarly to that described above, one or more imaging systems in the capsule endoscope may be used to help navigate the capsule endoscope. When the capsule endoscope has been navigated to the desired region of interest, the capsule endoscope may be disengaged from the tether as described above. Thereafter, a positive pressure provided by the pressure modulator (e.g., syringe 1632) may be formed in the tether and the port 1628. This positive pressure causes the drug to be urged down the tether and through the port 1628 towards the lesion. Furthermore, the now-detached capsule endoscope 1610 may be controlled (e.g., via an external magnetic control system as described below) such that its imaging system(s) observe the effect of drug delivery and enable confirmation that the drug was appropriately delivered.

Figure 18A:
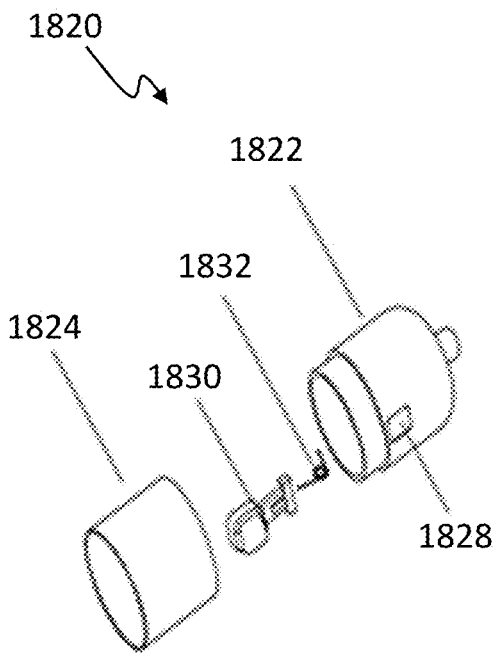
FIGS. 18A and 18B are exploded and side cross-sectional schematic views, respectively, of an exemplary variation of a tether with a housing and port.
Figure 18B:
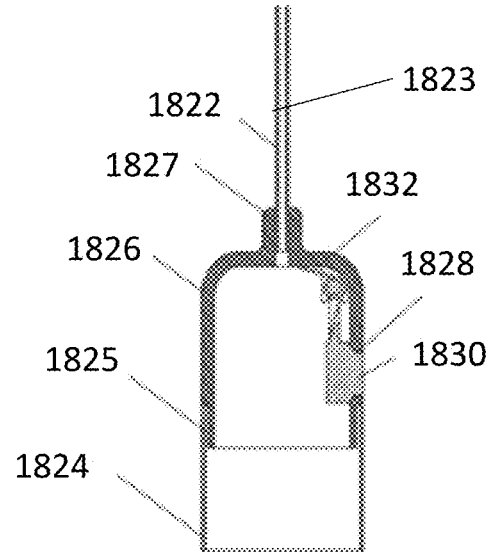
Figure 18C:
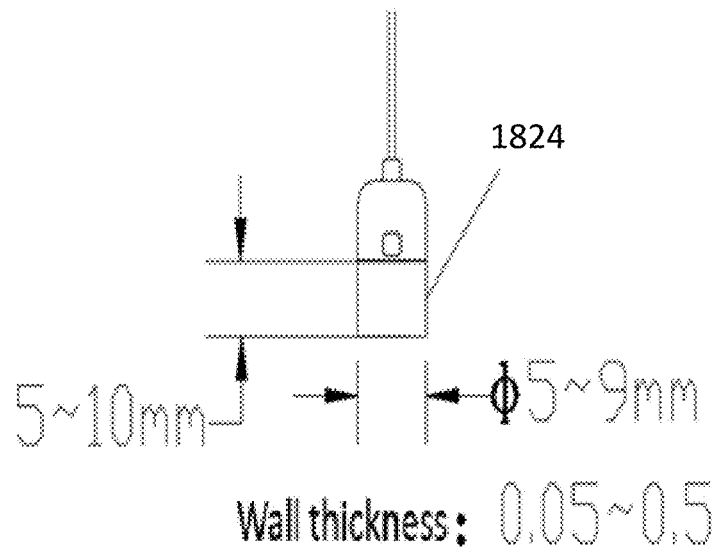
FIG. 18C is an illustrative schematic depicting exemplary dimensional ranges of aspects of the tether variation depicted in FIGS. 18A and 18B.

FIGS. 18A-18C depict another exemplary variation of a tether 1820 for coupling to a capsule endoscope, where the tether 1820 includes a housing having a port permitting passage of fluid therethrough. The tether 1820 includes a clamp including a flexible, elastic sheath 1824 for releasably engaging a capsule endoscope, and a housing 1826 including a chamber between the sheath 1824 and a flexible member 1822. For example, the sheath 1824 may be coupled to the housing 1826 through adjoining circumferential surfaces 1825 (e.g., via mechanical interfit, epoxy, etc) or any suitable feature. Furthermore, the housing 1826 may be coupled to the flexible member 1822 through adjoining circumferential surfaces 1827 (e.g., via mechanical interfit, epoxy, etc.) or any suitable feature. FIG. 18C illustrates exemplary dimensional ranges for the sheath 1824, which may have a length of between about 5 mm and 10 mm, an outer diameter between about 5 mm and about 9 mm, and a wall thickness between about 0.05 mm and about 0.5 mm.

As shown in FIGS. 18A and 18B, the housing 1826 may furthermore include a port 1828. The port 1828 may be selectively covered by a valve 1830 to modulate flow through the port 1828. In some variations, the valve 1830 may be a one-way valve that permits flow only in one direction. Additionally or alternatively, the valve 1830 may be biased towards a closed state, such as with a spring 1832 (e.g., torsion spring, flexible member functioning similar to a spring, and the like). Exemplary operation of the port 1828 and valve 1830 is described in further detail below.

Figure 19A:
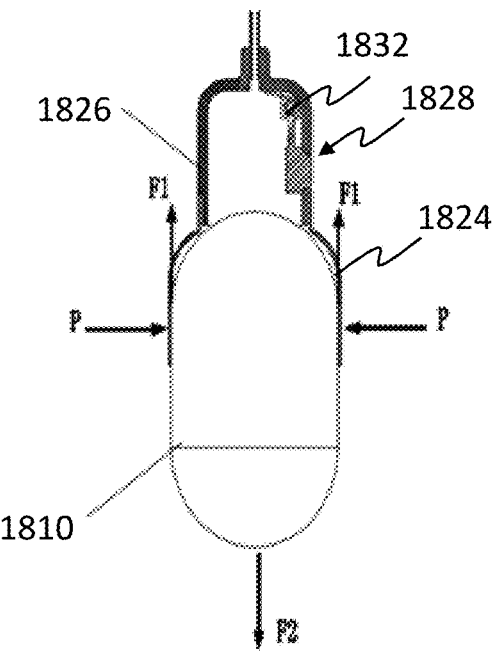
FIG. 19A is a force diagram illustrating engagement of the capsule endoscope with the tether variation depicted in FIGS. 18A and 18B.

In some variations, the sheath 1824 and the housing 1826 may cooperate to couple the capsule endoscope to the tether 1820. For example, as shown in FIG. 19A, the sheath 1824 may elastically deform to constrict around and engage the capsule endoscope 1810, thereby generating a pressure P that produces a friction force F1 on the contact surface between the sheath 1824 and the capsule endoscope 1810. The engagement between the capsule endoscope 1810 and the sheath 1824 may be substantially fluid-tight. Friction force F1 tends to retain the capsule endoscope 1810 within the sheath 1824. As shown in the diagram of FIG. 19A, a force F2 (countering the friction force F1) is produced by the sheath 1824 under environmental pressure (e.g., due to peristaltic pressure from the digestive tract muscles). As long as F1>F2, the capsule endoscope is retained in the sheath 1824.

Figure 19B:
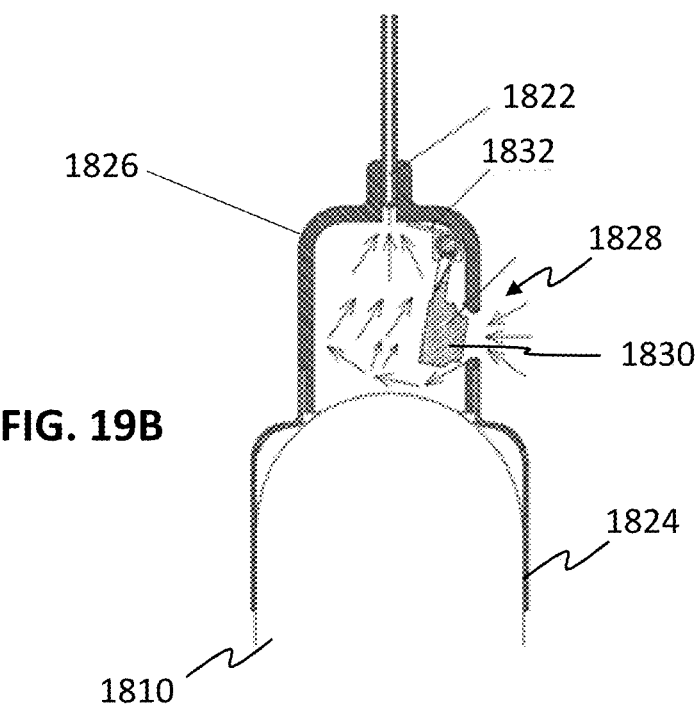
FIG. 19B is an illustrative schematic of opening of the port in the tether variation depicted in FIGS. 18A and 18B.

While the capsule endoscope 1810 is retained in the sheath 1824, controlled pressure differentials between inside of the housing 1826 and outside of the housing 1826 may open or close the valve 1830 covering the port 1828. For example, as shown in FIG. 19B, the chamber of the housing 1826 may be in fluidic communication with the lumen of the flexible member 1822, such that a vacuum source coupled to the flexible member 1822 may produce a sufficient pressure drop within the chamber in order to overcome the spring force biasing the valve 1830 closed. In other words, once the internal housing pressure is reduced to be lower than the pressure outside of the housing (by a differential sufficient to overcome the spring force), the valve 1830 may open, thereby permitting passage of fluid through the port 1828. In the open state shown in FIG. 19B, for example, fluid from outside the housing 1826 may enter the housing 1826, flow into the chamber, into the lumen of the flexible member 1822, and into a collection unit outside of the patient.

For example, in a method for obtaining a liquid biopsy, the capsule endoscope 1810 may be advanced to a region of interest, and an imaging system of the capsule endoscope may be used to observe surrounding patient fluid. When presence of sufficient patient fluid is determined, a sufficient negative pressure may be produced in the housing 1826 so as to open the valve 1830 and allow patient fluid to enter the housing 1826 through the open port 1828. The negative pressure further allows the withdrawal of patient fluid into the flexible member and into a collection unit.

Figure 20A:
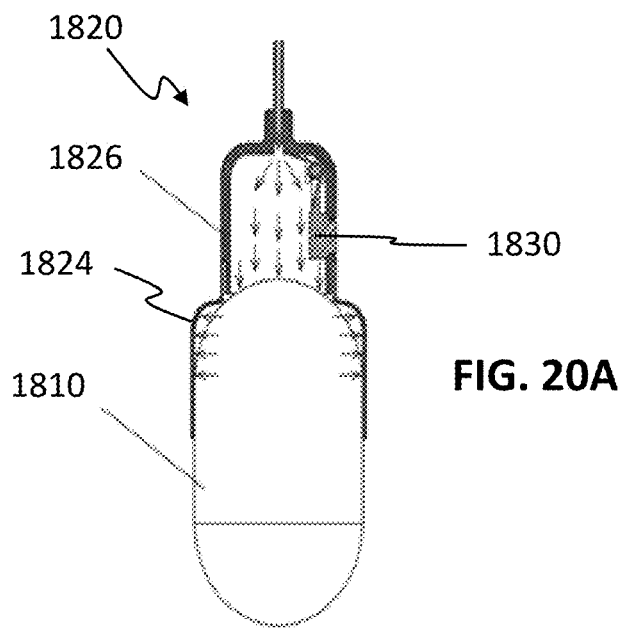
FIGS. 20A and 20B are illustrative schematics depicting disengagement between the capsule endoscope and the tether variation depicted in FIGS. 18A and 18B.
Figure 20B:
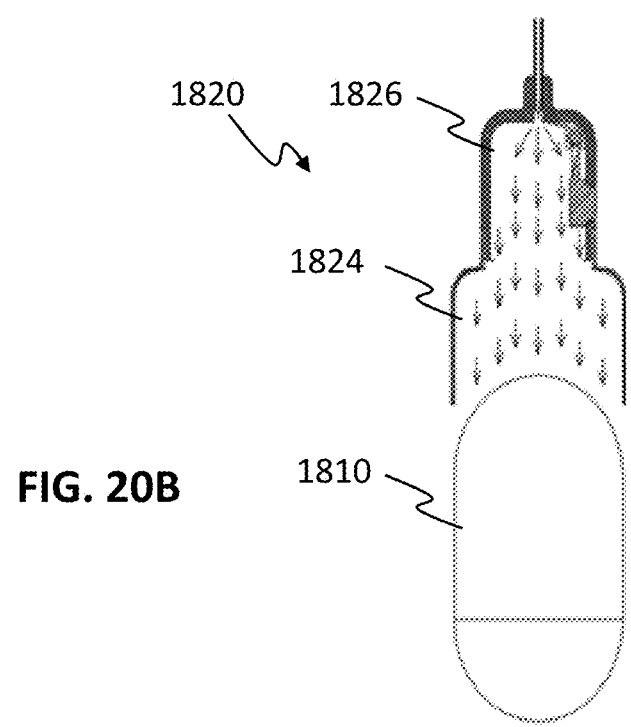

FIGS. 20A and 20B illustrate an exemplary process for disengaging the capsule endoscope 1810 from the tether 1820. As shown in FIG. 20A, a positive pressure may be introduced through the lumen of the flexible member and into the housing 1826 (e.g., with a syringe, pump, or other suitable pressure source). The pressure increase in the chamber may close the valve 1830 (if previously open). Similar to that described above with respect to FIG. 16B, further increased pressure within the housing may cause the flexible sheath 1824 to radially expand and reduce the friction force F1, and/or generate a forward/distal thrust force urging the capsule endoscope distally, Accordingly, as shown in FIG. 20B, such increased pressure within the housing 1826 may cause the capsule endoscope 1810 to disengage from and become released from the sheath 1824 of the tether. The released capsule endoscope may, for example, then by passed by the patient naturally through the digestive tract.

Figure 21A:
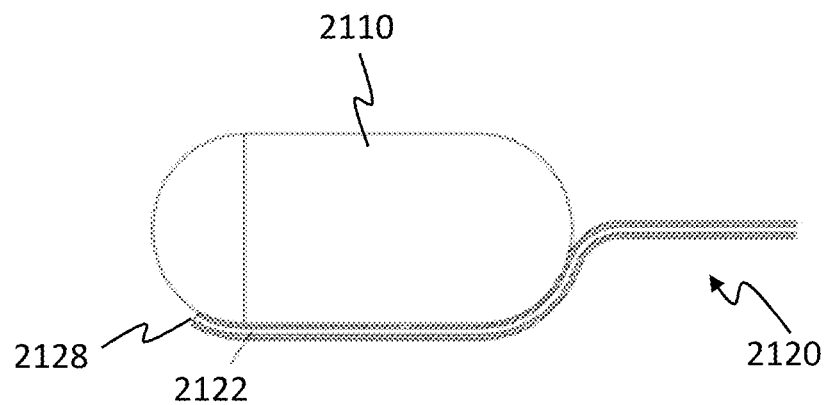
FIGS. 21A and 21B are illustrative schematics of an exemplary variation of a tether variation coupled directly to a capsule endoscope.

In some variations, an endoscopic system may include a port on the flexible member. For example, as shown in FIG. 21A, an exemplary variation of a tether 2120 may include a flexible member 2122 having a port 2128 on its distal end. The flexible member 2122 may be coupled to a capsule endoscope 2110 (e.g., an outer housing of a capsule endoscope including a distal imaging system in its distal end, and/or a proximal imaging system in its proximal end, as described above). For example, as shown in FIG. 21A, a longitudinal segment of the flexible member may be longitudinally coupled to the capsule endoscope 2110. The flexible member 2122 may be coupled to the capsule endoscope 2110 in any suitable manner. For example, the flexible member 2122 may be bonded to the capsule endoscope 2110 with a suitable epoxy. As another example, the flexible member 2122 may be fed through one or more fittings (e.g., eyes or rings) arranged along an outer surface of the capsule endoscope 2110 and secured axially with epoxy and/or with a flange or the like. Furthermore, although FIG. 21A depicts the flexible member 2122 as extending substantially in a straight line, in other variations the flexible member 2122 may traverse the capsule endoscope 2110 in any suitable manner (e.g., serpentine, helical, etc.). As yet another example, at least a portion of the flexible member 2122 may be co-extruded with a feature of the capsule endoscope 2110 so as to be integrally formed.

Figure 21B:
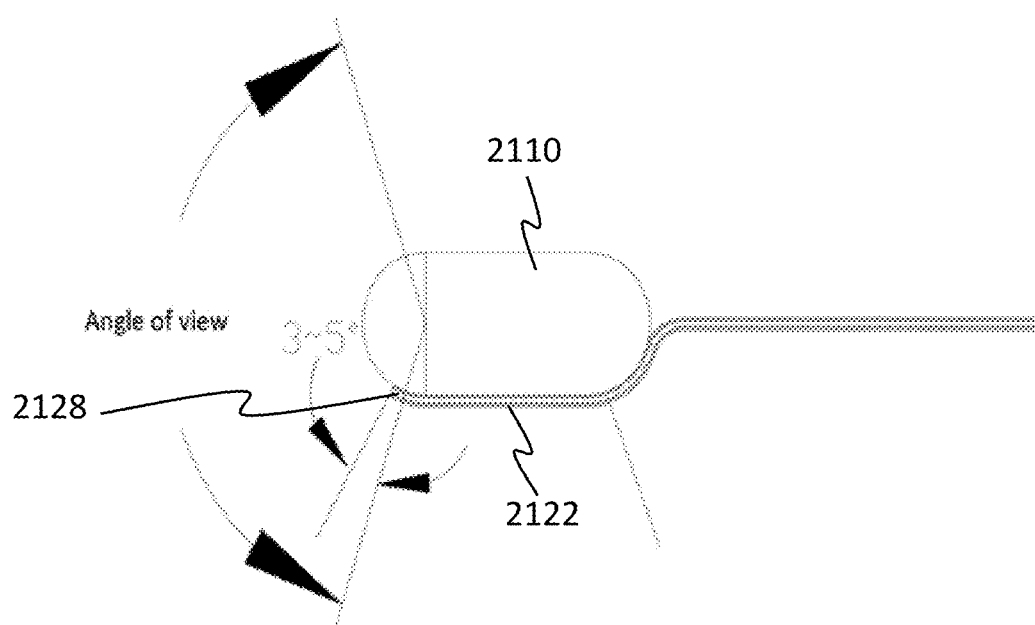
Figure 21C:
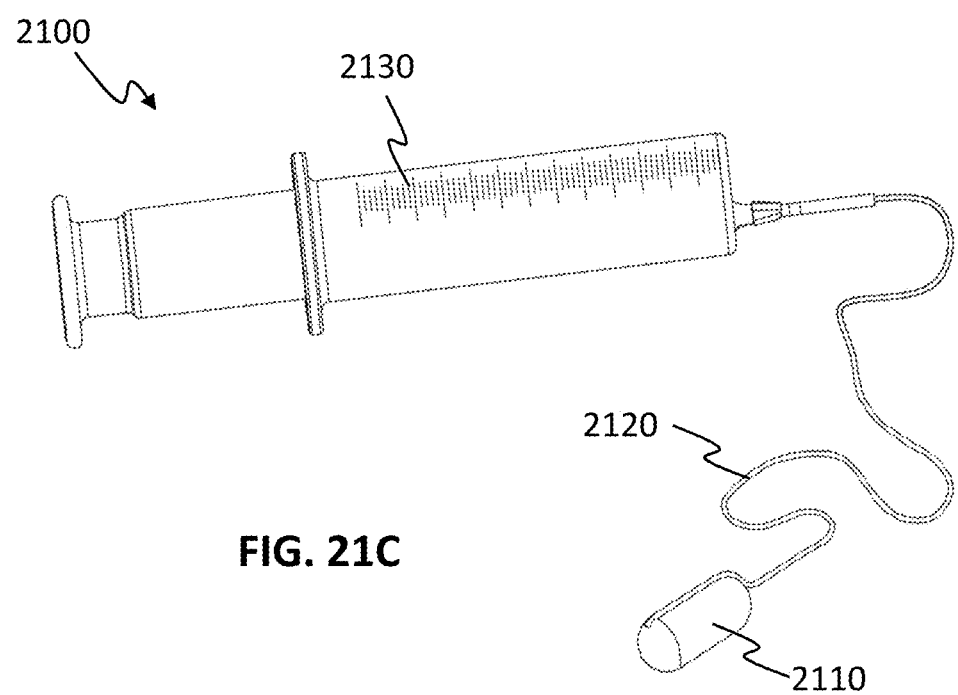
FIG. 21C is an illustrative schematic of a tethered system include the tether variation depicted in FIGS. 21A and 21B.

As shown in FIG. 21B, in some variations the distal end of the flexible member 2122 may be arranged such that port 2128 is visible within the distal imaging system's field of view, which may, for example, enable the distal imaging system to observe activity around the port 2128 (e.g., liquid entering the flexible member through the port 2128 during liquid biopsy, liquid exiting the flexible member through the port 2128 during drug delivery, etc.). In an exemplary variation as shown in FIG. 21C, the distal end of the flexible member 2122 may extend approximately between about 3 degrees and 5 degrees into the distal imaging system's angle of view such that the port 2128 is within the field of view. However, the distal end of the flexible member 2122 may extend further (e.g., between about 5 degrees and 10 degrees, or greater) or less (e.g., between about 1 degree and about 3 degrees) in other variations.

As shown in FIG. 21B, in a system 2100, a capsule endoscope 2110 may be coupled to a tether (to flexible member 2122 having a port 2128) as described above. The capsule endoscope 2110 may, for example, be similar to the capsule endoscope 600 described above with reference to FIGS. 6A-6C having proximal and distal imaging systems, except that the capsule endoscope 2110 may omit a port. The flexible member 2122 may be coupled to a pressure modulator 2130 (e.g., pressure source or vacuum source, such as a syringe or pump).

Figure 22A:
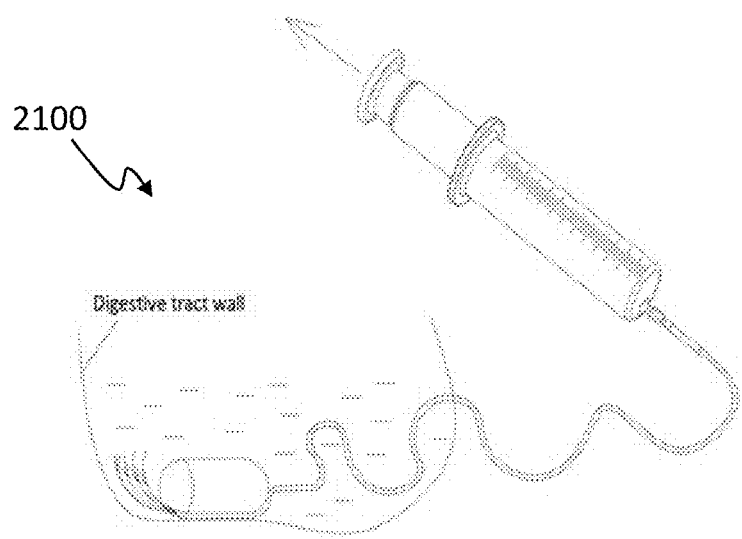
FIG. 22A is an illustrative schematic depicting a method for performing liquid biopsy using the tether variation depicted in FIGS. 21A and 21B.

FIG. 22A illustrates an exemplary use of the system 2100 in which the system 2100 is advanced to a fluid environment (e.g., in pancreatic juice). The distal imaging system of the capsule endoscope 2110 may be used to observe patient fluid in the surroundings of the capsule endoscope, thereby confirming the presence of patient fluid adjacent the port 2128. When presence of sufficient patient fluid is confirmed (e.g., submersion of the port 2128 in the patient fluid is determined), a negative pressure provided by the pressure modulator 2130 may be formed in the flexible member 2122 and in the port 2128. This negative pressure causes the patient fluid to be drawn into the port 2128, the flexible member 2122, and out of the patient into a collection (e.g., syringe).

Figure 22B:
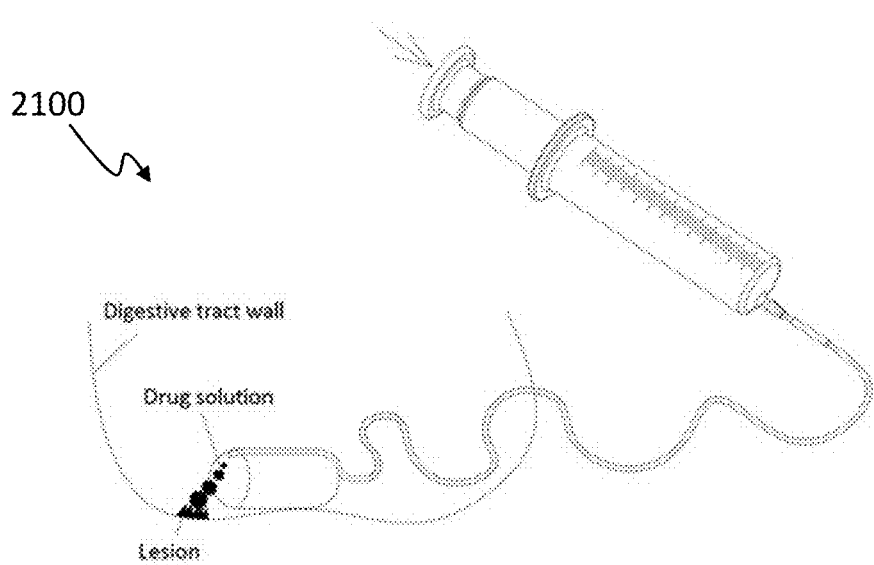
FIG. 22B is an illustrative schematic depicting a method for performing drug delivery using the tether variation depicted in FIGS. 21A and 21B.

Additionally, as shown in FIG. 22B, the system 2100 may be advanced to a region of interest including a lesion. The distal imaging system in the capsule endoscope 2110 may be used to observe the lesion and confirm that the port 2128 is in a suitable location and/or that the capsule endoscope is in a suitable orientation for treatment. When the suitable location and/or orientation is determined, a drug (e.g., a therapeutic agent) may be delivered in the flexible member 2122, and a positive pressure provided by the pressure modulatory may be formed in the flexible member 2122 and the port 2128. This positive pressure causes the drug to be urged down the flexible member and out of the port toward the lesion.

Figures 23A, 23B:
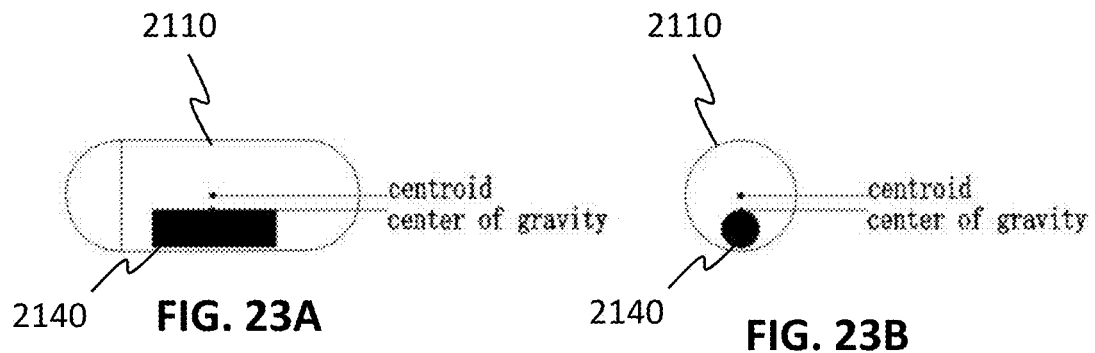
FIGS. 23A and 23B are side and cross-sectional schematic views, respectively, of an exemplary variation of a capsule endoscope having a biased center of gravity.
Figure 23C:
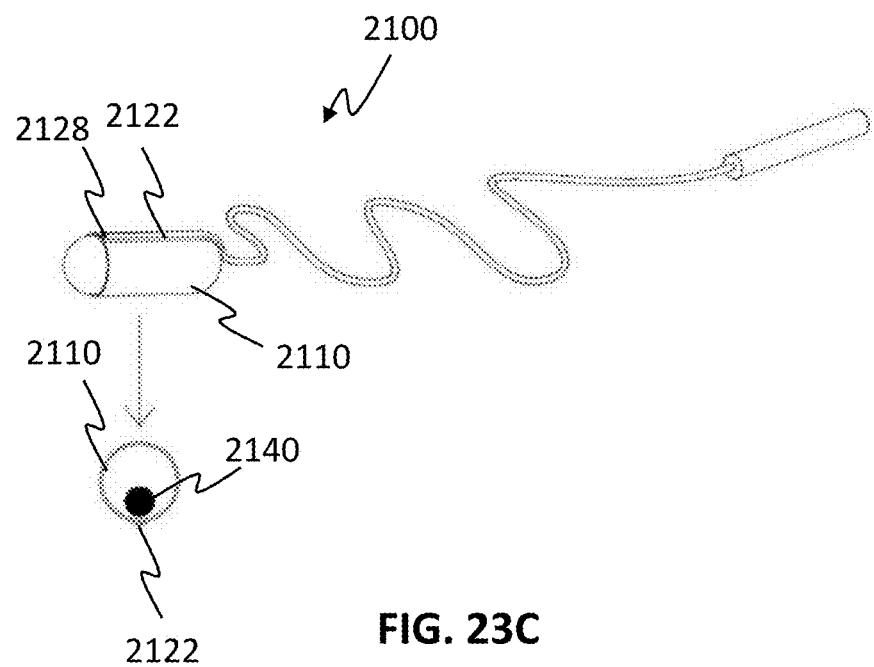
FIG. 23C is an illustrative schematic depicting the capsule endoscope variation depicted in FIGS. 23A and 23B in combination with the tether variation depicted in FIGS. 21A and 21B.

In some variations, as shown in FIGS. 23A and 23B, the capsule endoscope 2110 may have a center of gravity that is biased toward the side of the capsule endoscope including the port 2128, such that the gravity may tend to help the submersion of the port 2128 in pooled fluid for obtaining liquid biopsy. As shown in FIGS. 23A and 23B, the center of gravity may be radially offset from the centroid, such as toward the port side of the capsule endoscope 2110. The center of gravity may be adjusted appropriately by, for example, distributing more weight (e.g., magnet 2140, which may be relatively dense) toward the port side of the capsule endoscope 2110. However, the center of gravity may additionally or alternatively be adjusted in other suitable ways, such as a non-uniform distribution of housing material (e.g., thickness of the housing may be greater, or the housing may have a heavier material on a side proximate the port 2128). Additionally or alternatively, a relatively buoyant element or feature (e.g., an air-containing compartment) may be located on an opposing side of the capsule endoscope relative to the port 2128. As shown in FIG. 23C, the bias in center of gravity and/or effect of buoyancy may tend to cause the capsule endoscope 2110 to rotate so as to submerge the distal end of the flexible member 2122 (and the port 2128) when in patient fluid.

FIGS. 24A-24C illustrate another exemplary variation of a tether 2420, which may be similar to the tether 2120 described above with reference to FIGS. 21-23 except as described below. While the tether 2120 described above is coupled directly to the capsule endoscope, the tether 2420 may be coupled directly to a clamp 2424. For example, a longitudinal segment of the flexible member 2422 may couple to the clamp 2424 in any suitable manner. The clamp 2424 may include a sheath or suction cup similar to that described above, which may, for example, leave a distal imaging assembly of the capsule endoscope substantially unobstructed. The port 2328 on a distal end of the flexible member 2422 may be in the field of view of the distal imaging assembly, similar to that described above with reference to FIG. 21C. As shown in FIGS. 24B and 24C, the clamp 2424 may be configured to receive the capsule endoscope 2410. Furthermore, like the capsule endoscope 2110, the capsule endoscope 2410 may include a center of gravity that is biased toward the side of the clamp 2424 including the port 2328.

Magnetic Control System

As described above, in some variations, the capsule endoscope may be controlled at least in part through a magnetic control system. For example, a capsule endoscope (e.g., as shown in FIGS. 2B and 2C, FIGS. 5B and 5C, FIG. 6C referenced above) may include one or more internal magnets that may be controlled by an external magnetic control system. The internal magnets may, for example, be permanent magnets (e.g., rare earth magnets, such as neodymium magnets).

In some variations, a capsule endoscope may include at least one internal magnet configured to enable six degrees of freedom (translation and rotation in each of three axes). For example, a capsule endoscope may include an internal magnetic assembly including a first magnet and a second magnet coupled to the first magnet, where the first magnet has a polarity oriented along a first direction and the second magnet has a polarity oriented along a second direction different from the first direction (e.g., the second direction may be perpendicular to the first direction). The external magnetic control system may provide magnetic forces that act upon the first and second magnets in tandem, thereby enabling both translation and rotation along three axes. Thus, the internal magnet(s) may allow complex and fine maneuvering of the capsule endoscope by an external magnetic control system, including maintaining a point position of the capsule endoscope while rotating the capsule endoscope around its longitudinal axis (a roll movement), as described below.

Figure 27B:
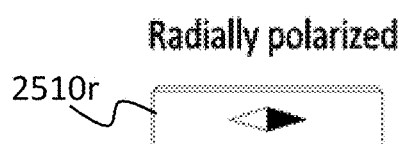
FIGS. 27A-27C are perspective, side, and top schematic views, respectively, of a radially polarized magnet.
Figure 27C:
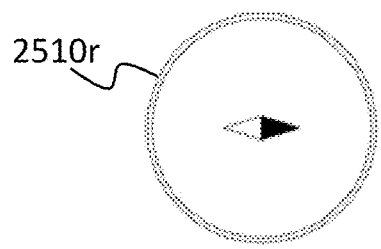
Figure 27A:
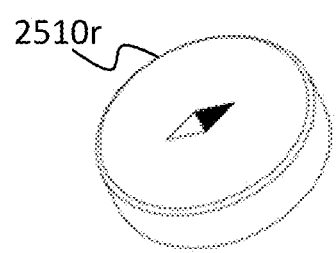
Figure 28B:
FIGS. 28A-28C are perspective, side, and top schematic views, respectively, of an axially polarized magnet.
Figure 28C:
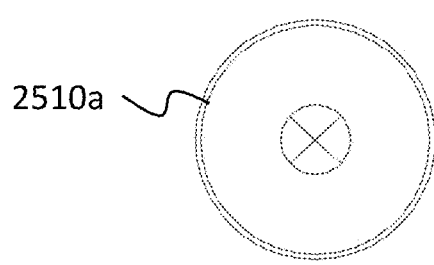
Figure 28A:
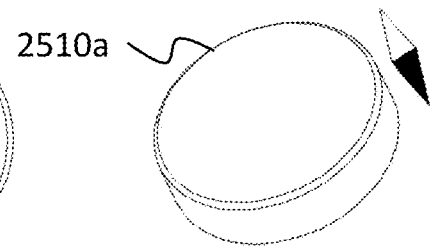

FIGS. 25A and 25B depicts one exemplary variation of an internal magnetic assembly 2500 including a first magnet 2510r and a second magnet 2510a, where the first magnet 2510r may be radially polarized (FIGS. 27A-27C), and the second magnet 2510a may be axially polarized (FIGS. 28A-28C). The first and second magnets may be generally disc-shaped, and coupled to each other along adjacent faces (e.g., with epoxy or other adhesive, fasteners, etc.) such that their polarities are orthogonal to each other. Although FIGS. 25A and 25B depict first magnet 2510r and the second magnet 2510a as disc-shaped, though may alternatively be any suitable shape. As shown in FIGS. 25A and 25B, the first and second magnets may be approximately the same size and shape, though in other variation they may differ in size (e.g., width or diameter, thickness, etc.) and/or shape. FIGS. 26A and 26B depict another exemplary variation of an internal magnetic assembly 2600 including a first magnet 2510r and a second magnet 2510a. The internal magnetic assembly 2600 is similar to the internal magnetic assembly 2500, except that in the internal magnetic assembly 2500 (FIGS. 25A-25B) the second magnet 2510a is arranged with its north pole pointing away from the first magnet 2510r, while in the internal magnetic assembly 2600 (FIGS. 26A-26B) the second magnet 2510a is arranged with its north pole pointing toward the first magnet 2510r.

Figure 29:
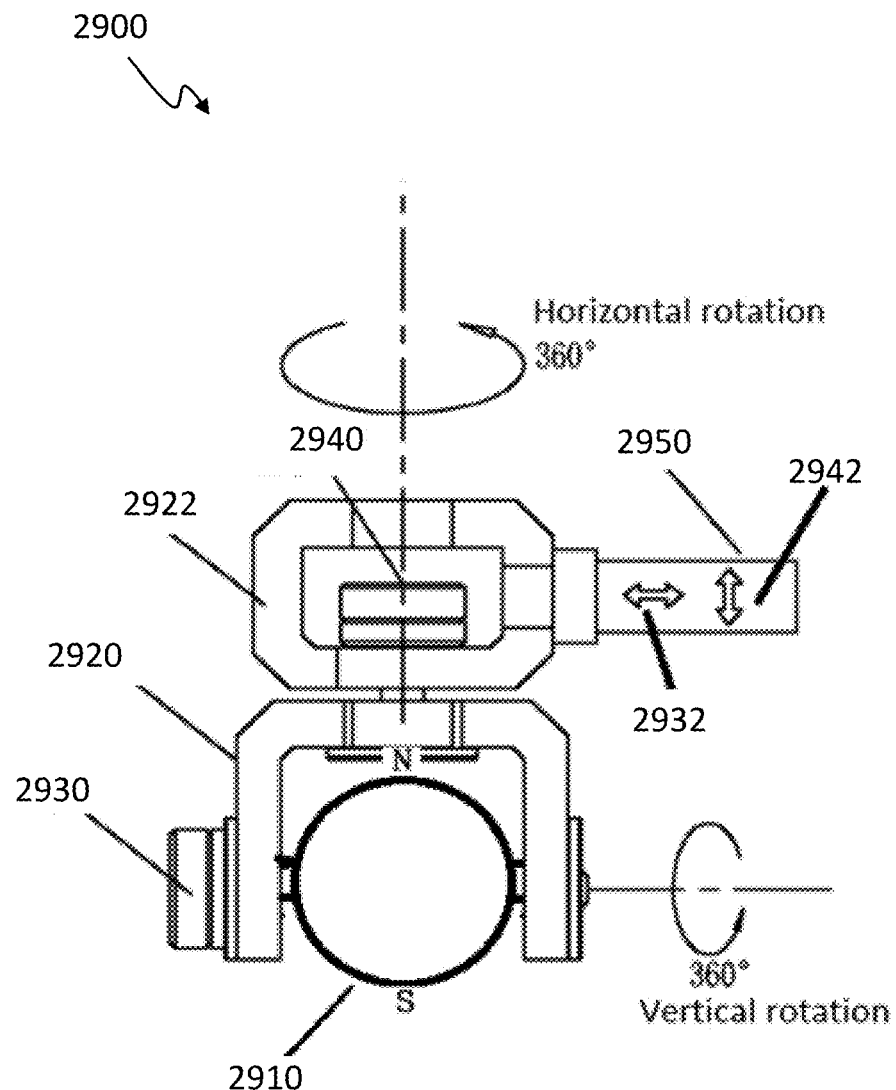
FIG. 29 is an illustrative schematic depicting an exemplary variation of an external magnetic control system.

The posture (position, orientation, etc.) of the capsule endoscope may be controlled at least in part with an external magnetic control system, such as the external magnetic control system 2900 shown in FIG. 29. In some variations, the external magnetic control system 2900 may be similar to that described in U.S. Pat. Nos. 10,076,234 and 10,070,854, each of which is hereby incorporated in its entirety by this reference.

For example, the external control system 2900 may include a spherical magnet 2910 (e.g., permanent magnet or electromagnet) controllable within a frame structure to provide a rotatable external magnetic field. Directional changes of the external magnetic field may cause the internal magnetic assembly (and the capsule endoscope) to change position and/or orientation.

The spherical magnet 2910 may be actuated to translate and/or rotate in three dimensional space. For example, the spherical magnet 2910 may be coupled to a lower frame portion 2920 of the frame structure, and the frame structure may be translated vertically and/or horizontally in frontward-backward and/or left-right directions (e.g., via an actuated arm, or along tracks, etc.). The spherical magnet 2910 may be mounted on a shaft that is rotatable through actuation of a first motor 2930, such that the first motor 2930 may provide vertical rotation of the spherical magnet 2910 around a horizontal axis. Additionally, the lower frame 2920 (to which the spherical magnet 2910 may be mounted) may be rotatable relative to an upper frame portion 2922 of the frame structure through actuation of a second motor 2940, such that the second motor 2940 may provide horizontal rotation of the spherical magnet 2910 around a vertical axis. In other variations, translating and/or rotating the spherical magnet 2910 may be performed in any suitable manner. In some variations, a user interface controls (e.g., control handle 2950) may be coupled to the frame structure to enable operation of such movements. For example, as shown in FIG. 29, the control handle 2950 may include one or more buttons (e.g., button 2932 which may control horizontal rotation, button 2942 which may control vertical rotation), knobs, or other suitable controls. Further details of an exemplary operation of the magnetic control system to manipulate the spherical magnet for control of a magnet internal to a patient are described in U.S. Pat. Nos. 10,076, 234 and 10,070,854, which were incorporated above.

Figures 30A, 30B:
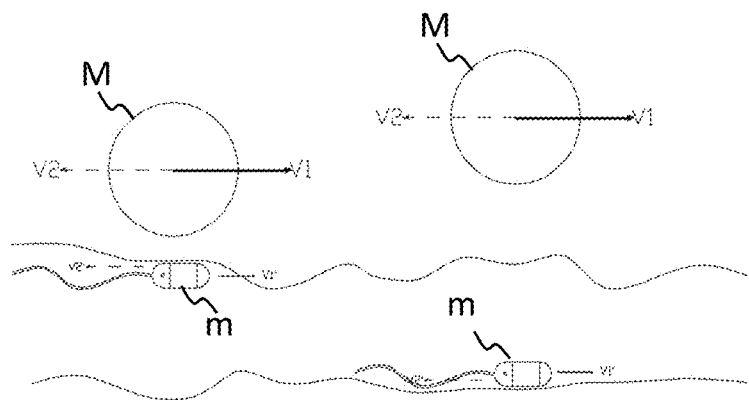
FIGS. 30A and 30B, FIGS. 31A and 31B, and FIGS. 32A and 32B are illustrative schematics depicting control of a capsule endoscope through motions of an external magnetic control system.
Figures 31A, 31B:
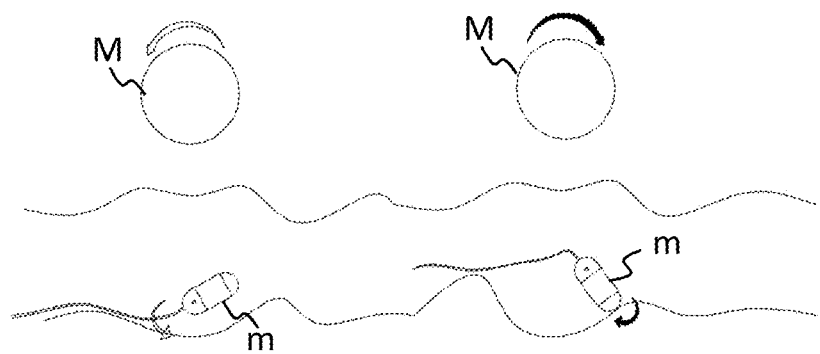
Figures 32A, 32B:
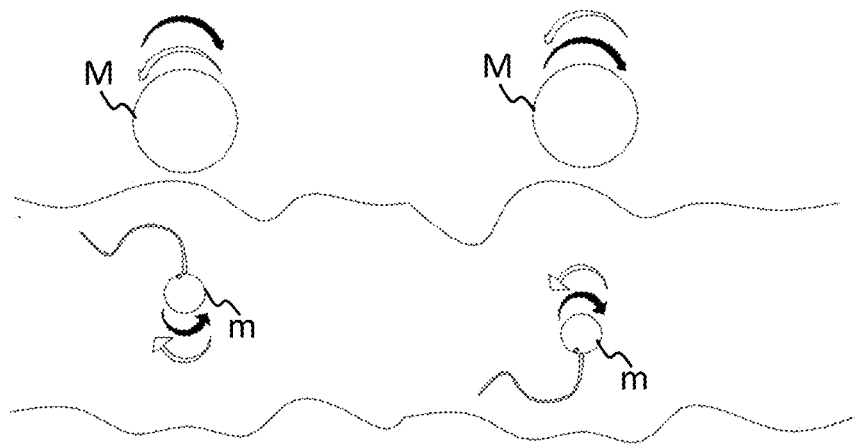

FIGS. 30A-32B illustrate exemplary controlled movements of the capsule endoscope using the external control system. For example, as shown in FIGS. 30A and 30B, translational movement of the external magnet (M) results in corresponding translational movement of the internal magnet assembly (m) in the capsule endoscope. Furthermore, the distance between the external magnet (M) and the internal magnet assembly (m) in the patient body may be controlled by moving the external magnet (M) closer to (FIG. 30A) or farther from (FIG. 30B) the patient body. Additionally, as shown in FIG. 31A, pitch movement of the external magnet (M) may result in a corresponding pitch movement of the internal magnet assembly (m). Similarly, as shown in FIG. 31B, a yaw movement of the external magnet (M) may result in a corresponding yaw movement of the internal magnet assembly (m). Furthermore, as shown in FIGS. 32A and 32B, a combined set of simultaneous pitch and yaw movements of the spherical external magnet (M) may result in a corresponding roll movement of the internal magnet assembly (m) in either direction. Accordingly, translational and rotational movement of the capsule endoscope may be controlled due to interactions between the magnetic control system and the internal magnetic assembly.

Pressure Modulator

As described above, systems for accessing a patient may include at least one pressure modulator coupled to the tether and configured to decrease pressure and/or increase pressure within the tether for withdrawing and/or urging fluid through a port (e.g., in the tether, in a capsule endoscope, etc.). The pressure modulator may be a pressure source and/or a vacuum source arranged in fluidic communication with the tether (e.g., a lumen of a flexible member in the tether).

Figure 33A:
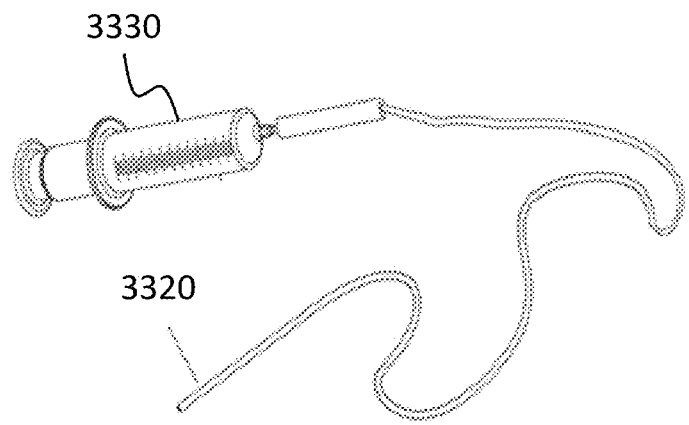
FIGS. 33A and 33B are illustrative schematics depicting exemplary variations of a pressure modulator including a syringe and a pump, respectively.

For example, as shown in FIG. 33A, the pressure modulator may include a syringe 3330 that is fluidically coupled to a flexible member of a tether 3320. The plunger of the syringe 3330 may be withdrawn in order to create negative pressure in the tether and draw fluid (e.g., for liquid biopsy) through a port (not shown) and through the tether 3320. The withdrawn fluid may be collected with the syringe 3330 and/or collected with another container fluidically connected in-line with the tether, similar to that described below with respect to FIG. 33B. Furthermore, the plunger of the syringe 3330 may be depressed in order to create positive pressure in the tether, such as to urge fluid (e.g., for drug delivery, for capsule endoscope disconnection from a clamp member as described above, etc.) through the tether 3320 and a port (not shown).

Figure 33B:
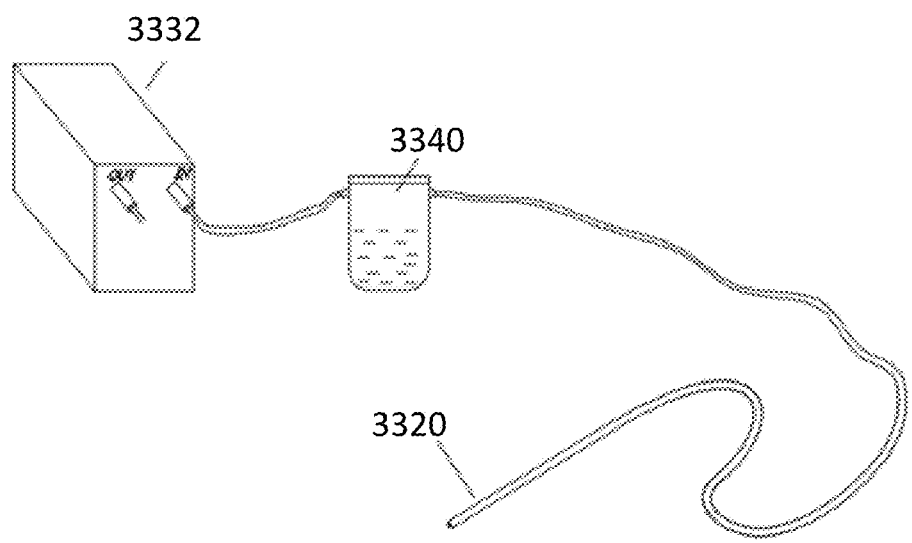

As another example, as shown in FIG. 33B, the pressure modulatory may include a vacuum pump 3332 that is fluidically coupled to a flexible member of a tether 3320. A collection unit 3340 (e.g., container) may be fluidically connected in-line with the tether, such that when the vacuum pump 3332 is turned on and creates negative pressure in the tether to withdraw fluid (e.g., liquid biopsy) into the tether 3320, the withdrawn fluid is transferred into the collection unit 3340. Furthermore, a pressure pump may be similarly fluidically coupled to the tether 3320 to create a positive pressure in the tether (e.g., for drug delivery, for capsule endoscope disconnection from a clamp member as described above, etc.). Alternatively, a pump capable of selectively being a vacuum pump or a pressure pump may be coupled to the tether, and toggled between vacuum and pressure modes.

Figure 34A:
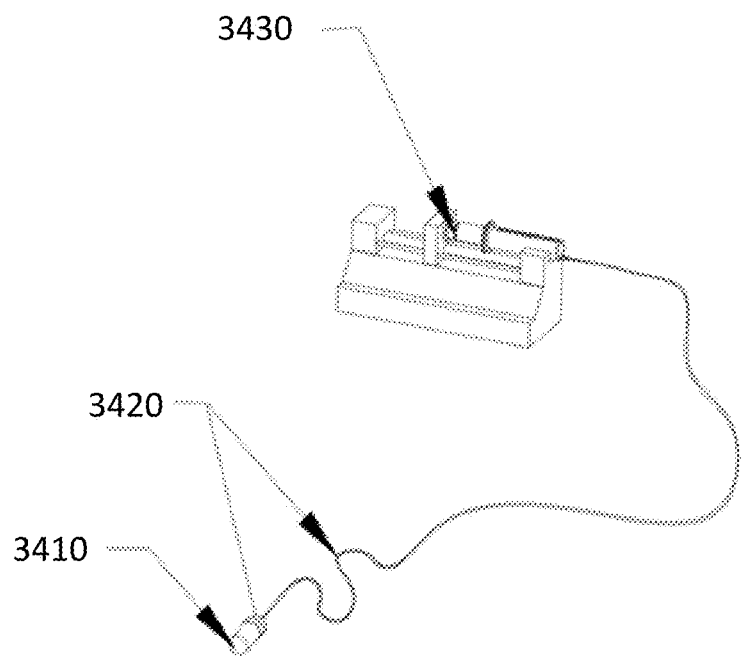
FIG. 34A is an illustrative schematic depicting another exemplary variation of a pressure modulator including a microflow syringe pump.
Figure 34B:
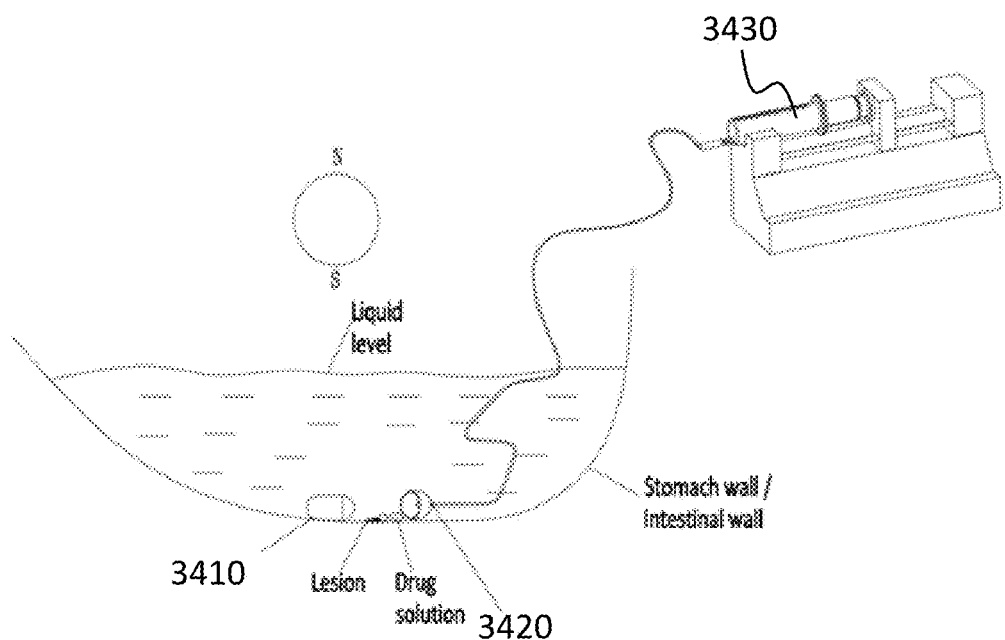
FIG. 34B is an illustrative schematic of a method of using the pressure modulator depicted in FIG. 34A.

In another exemplary variation as shown in FIGS. 34A and 34B, a system for accessing a patient may include a pressure modulator including a microflow syringe pump 3430. The microflow syringe pump may be coupled to the tether 3420 as described above, and the tether 3420 may be coupled to a capsule endoscope 3410 in any suitable manner such as those variations described above. After advancing the capsule endoscope 3410 to a region of interest (e.g., lesion) and enabling a port to be proximate the region of interest, the microflow syringe pump 3430 may be actuated to deliver a drug through the tether 3420 and the port (not labeled). The microflow syringe pump 3430 (in combination with the capsule endoscope and tether arrangements such as those described herein) may achieve a long-acting therapeutic effect by continuously releasing micro-doses of drug to the region of interest. In some variations, the capsule endoscope may be controlled (e.g., by an external magnetic control system as described above) such that its imaging system observes the delivery of the drug through the port to the region of interest. After treatment is complete, the capsule endoscope may be released from the tether and passed by the patient's gastrointestinal tract, and the tether may be withdrawn and removed from the patient.

Methods for Accessing a Patient

Various methods for accessing a patient may include using one or more capsule endoscopes, such as any of the capsule endoscope variations described above. For example, in some variations, a method for obtaining one or more substances from a patient may include advancing a capsule endoscope into a body cavity (e.g., gastrointestinal tract) of a patient, where the capsule endoscope is coupled to a tether including a flexible member with a lumen, positioning the capsule endoscope at a region of interest, and withdrawing a patient sample from the region of interest through the lumen (e.g., by forming a negative pressure in the lumen). The capsule endoscope may be advanced with an external magnetic control system and/or through peristalsis, etc. The patient sample may be withdrawn through a port that is in fluidic communication with the lumen. The port may be located in any one or more structures in or around the capsule endoscope and/or tether, as described above with respect to various tethered capsule endoscope variations.

Generally, the region of interest may be any suitable location in the gastrointestinal tract and/or other features of the digestive system, such as the mouth, esophagus, stomach, small intestine, large intestine, anus, liver, pancreas, gallbladder, and the like. However, the region of interest may be in any suitable body cavity or other region of a patient.

The method may be used to obtain patient samples that are fluid samples from the body (e.g., liquid biopsy). For example, one exemplary application of the method is obtaining a sample of pancreatic juice from a patient, where the pancreatic juice may, for example, be analyzed for mutations indicating the presence of cancer. Another exemplary application of the method is obtaining a sample of intestinal flora (e.g., bacteria) which may, for example, be analyzed to assess gut health. While any suitable amount of fluid may be withdrawn (e.g., depending on sample availability or the application of the method), in some variations the method may include withdrawing between about 0.5 mL and about 15 mL, between about 0.5 mL and about 10 mL, between about 0.5 and about 5 mL, between about 5 mL and about 10 mL, between about 1 mL and about 3 mL, more than about 10 mL, or more than about 15 mL, etc.

Additionally or alternatively, the method may include obtaining any suitable matter from the body cavity of the patient. For example, the method may be used to obtain particle patient samples and/or suitable foreign particles that may be residing in fluid or may be small and/or light enough to be suctioned through the port. Exemplary particles may include, for example, cancer cells, debris and/or exosomes shedding from cancer cells and/or immune cells, other suitable biomarkers, etc.

As another example, in some variations, a method for delivering one or more substances may include advancing a capsule endoscope into a body (e.g., gastrointestinal tract) of a patient, where the capsule endoscope is coupled to a tether including a flexible member with a lumen, positioning the capsule endoscope at a region of interest, and administering a therapeutic substance to the region of interest through the lumen (e.g., by forming a positive pressure in the lumen). The capsule endoscope may be advanced with an external magnetic control system and/or through peristalsis, etc. The drug may be delivered through a port that is in fluidic communication with the lumen. The port may be located in any one or more structures in or around the capsule endoscope and/or tether, as described above with respect to various tethered capsule endoscope variations. In some variations, the capsule endoscope may remain static in a single location and orientation during delivery of the substance, while in other variations the capsule endoscope may be moved while delivering the substance (e.g., rotating about an axis, translating, etc.) to coat or spray a wider surface area of treatment.

The method may be used to deliver one or more therapeutic substances to the body cavity of the patient. For example, one exemplary application of the method is delivering one or more drugs to an intestinal region of interest for treatment of inflammatory bowel disease (IBD) such as Crohn's disease or ulcerative colitis. Exemplary drugs that may be delivered include thrombin, norepinephrine, batroxobin, etc., as well as suitable drug combinations (e.g., about 240,000 units gentamicin combined with between about 50 ml to about 100 ml of 5% GNS, between about 5 mg to about 10 mg dexamethasone, and about 1.2 g of metronidazole). As another example, the method may be used to deliver one or more drugs to an esophageal region to treat one or more lesions, such as in target therapy using nanoparticles such as multimodality nanoparticles suitable for imaging, characterization, and therapy, etc. (e.g., for SERS optical biopsy, photothermal therapy, photodynamic therapy, etc.). Exemplary particles for these applications include gold or silver nanoparticles, carbon nanotubes, and gold nanorods, etc. As yet another example, the method may be used to spray a drug or other therapeutic substance, such as for stopping or reducing gastrointestinal bleeding (e.g., in the esophagus, stomach, small bowel, colon, etc.). Exemplary drugs for spraying include Hemospray® Endoscopic Hemostat (Cook Medical, Winston-Salem, N.C., USA), Ankaferd Blood Stopper (Ankaferd Health Products, Ltd., Istanbul, Turkey), EndoClot® Polysaccharide Hemostatic System (EndoClot Plus, Inc., Santa Clara, Calif., USA), and the like.

In yet other variations, the methods described herein may be used to deliver and/or withdraw other suitable substances using capsule endoscope systems such as those described herein. For example, the methods may be used to release fluid (e.g., gas such as air or nitrogen, liquid such as saline or water, etc.) via a capsule endoscope system with a port, which may be used to inflate at least a portion of the gastrointestinal tract (e.g., stomach, small intestine, large intestine, colon, etc.). Such inflation may be useful, for example, to aid visibility for imaging, etc. within the gastrointestinal tract using the same endoscope device or other suitable imaging device. As another example, the methods may be used for facilitating nanoscale drug delivery by releasing nanoparticle drug carriers (e.g., liposomes, carbon nanotubes, dendrimers, polymeric nanoparticles, gold-based nanoparticles, etc.). Suitable drugs to be carried may include anti-inflammatory agents, anti-infective agents, and the like.

In some variations, the same capsule endoscope during a procedure may be used for both obtaining a patient sample and delivering a drug. For example, after advancing a capsule endoscope to a region of interest, a negative pressure may be formed in the tether to withdraw a patient sample or other matter through the port, and a positive pressure may subsequently be formed in the tether to deliver a drug or other matter through the port. Alternatively, a positive pressure may be formed before forming a negative pressure.

Trypsin Sensor

Also disclosed herein is a trypsin sensor that can have advantages such as simple synthesis, short preparation period, easiness in operation, low cost, low technical threshold and the like, and is easy to realize large-scale production and use. Moreover, the trypsin sensor prepared by the method can be applied to trypsin detection in a large scale, so that the problems of great technical difficulty, long detection time, high cost and incapability of meeting the current requirements of the existing trypsin detection mode are solved. In some variations, the trypsin sensor can comprise a trypsin detection film.

In some variations, the trypsin detection film can detect a sample comprising a trypsin concentration of about 50 μg/mL to about 1,000 μg/mL. In some variations, the trypsin detection film can detect a sample comprising a trypsin concentration of at least about 50 μg/mL. In some variations, the trypsin detection film can detect a sample comprising a trypsin concentration of at most about 1,000 μg/mL. In some variations, the trypsin detection film can detect a sample comprising a trypsin concentration of about 50 μg/mL to about 100 μg/mL, about 50 μg/mL to about 200 μg/mL, about 50 μg/mL to about 300 μg/mL, about 50 μg/mL to about 400 μg/mL, about 50 μg/mL to about 500 μg/mL, about 50 μg/mL to about 1,000 μg/mL, about 100 μg/mL to about 200 μg/mL, about 100 μg/mL to about 300 μg/mL, about 100 μg/mL to about 400 ng/mL, about 100 μg/mL to about 500 μg/mL, about 100 μg/mL to about 1,000 μg/mL, about 200 μg/mL to about 300 μg/mL, about 200 μg/mL to about 400 μg/mL, about 200 μg/mL to about 500 μg/mL, about 200 μg/mL to about 1,000 μg/mL, about 300 μg/mL to about 400 ng/mL, about 300 μg/mL to about 500 μg/mL, about 300 μg/mL to about 1,000 μg/mL, about 400 μg/mL to about 500 μg/mL, about 400 μg/mL to about 1,000 μg/mL, or about 500 μg/mL to about 1,000 μg/mL. In some variations, the trypsin detection film can detect a sample comprising a trypsin concentration of about 50 μg/mL, about 100 μg/mL, about 200 μg/mL, about 300 μg/mL, about 400 μg/mL, about 500 μg/mL, or about 1,000 μg/mL. In some variations, when the trypsin concentration reaches any of the above thresholds, the trypsin detection film will trigger a color change that can be observed through images taken by the capsule endoscope.

The trypsin detection film can comprise a substrate (e.g., polymeric film substrate) and a dye attached to the substrate. In some variations, the dye can comprise bromocresol purple dye, 3',5,5'-tetramethyl benzidine dye, triarylmethane dye, xylenol orange dye, metal complex dye, or any combination thereof. In some variations, the dye further comprises a solvent, such as water and/or an alcohol solvent. For example, the solvent may be a lower alcohol, such as ethanol.

In some variations, the concentration of the dye is about 0.25 mg/mL to about 2.5 mg/mL. In some variations, the concentration of the dye is at least about 0.25 mg/mL. In some variations, the concentration of the dye is at most about 2.5 mg/mL. In some variations, the concentration of the dye is about 0.25 mg/mL to about 0.5 mg/mL, about 0.25 mg/mL to about 1 mg/mL, about 0.25 mg/mL to about 1.5 mg/mL, about 0.25 mg/mL to about 2 mg/mL, about 0.25 mg/mL to about 2.5 mg/mL, about 0.5 mg/mL to about 1 mg/mL, about 0.5 mg/mL to about 1.5 mg/mL, about 0.5 mg/mL to about 2 mg/mL, about 0.5 mg/mL to about 2.5 mg/mL, about 1 mg/mL to about 1.5 mg/mL, about 1 mg/mL to about 2 mg/mL, about 1 mg/mL to about 2.5 mg/mL, about 1.5 mg/mL to about 2 mg/mL, about 1.5 mg/mL to about 2.5 mg/mL, or about 2 mg/mL to about 2.5 mg/mL. In some variations, the concentration of the dye is about 0.25 mg/mL, about 0.5 mg/mL, about 1 mg/mL, about 1.5 mg/mL, about 2 mg/mL, or about 2.5 mg/mL. In some variations, the concentration of the dye is 0.25-2.5 mg/mL, preferably 1-2 mg/mL.

In some variations, the dye can change its color based on the concentrations of trypsin in an environment surrounding the dye. Thus, the interaction between the dye and trypsin can be used for developing color, and the color change of the trypsin detection film is observed, so that the detection result can be obtained. In addition, different color development effects can be achieved by dye mixing or changing the concentration of the dye. The dye (e.g., bromocresol purple dye) can be combined with trypsin through a chemical bond (e.g., a non-covalent bond). For example, a hydrophobic core of trypsin can be combined with a nonpolar group of the bromocresol purple dye. The volume of the combined aggregate is larger than that of the bromocresol purple dye, so the molar absorption coefficient of the dye is changed, in turn changing the light scattering signal and color of the bromocresol purple dye. Since the signal intensity is proportional to the number of particles per unit volume, i.e., the concentration of trypsin, the detection of the concentration of trypsin can be achieved by observing the color change of the bromocresol purple dye. In the detection process, the bromocresol purple dye in the trypsin detection film shows different colors for the trypsin concentrations with different concentrations, and the trypsin concentration can be quantitatively detected through color change (e.g., from blue to yellow). The concentration of trypsin can be determined by detecting the degree of change before and after the detection, for example, the concentration of trypsin in a liquid environment can be determined by the change of the shade (e.g., color tone), thereby detecting the pancreatic juice when in contact with a high concentration of trypsin. The trypsin detection film is applied to the detection of trypsin, and has the characteristics of simple operation, obvious color change, quick detection, high efficiency, low requirement on detection personnel and the like.

In some variations, the substrate can comprise a polymeric film substrate. In some variations, the polymeric film substrate can be a polyionic film, such as a polyionic liquid film. The polymeric film substrate can have excellent performances of both the ionic liquid and the polymer, can overcome the fluidity of the ionic liquid, has unique physicochemical properties, and/or can be well applied to the field of medical detection. In some variations, the dye and the polymeric film substrate can form a stable film. For example, the dye can be attached to the substrate by ionic interactions between the dye and substrate.

In some variations, the polyionic liquid can comprise an ionic liquid including at least one of imidazole ionic liquid, pyridine ionic liquid, quaternary ammonium salt ionic liquid, quaternary phosphine ionic liquid or pyrrolidine ionic liquid. It is understood that the ionic liquid used to prepare the polymer film substrate may be a functionalized ionic liquid commonly used in the art, depending on the function that the ionic liquid performs. Illustratively, the ionic liquid may be imidazole ionic liquid, pyridine ionic liquid, quaternary ammonium salt ionic liquid, pyrrolidine ionic liquid, or the like. The specific type of ionic liquid in the examples of the present application is not limited, and several of the ionic liquids listed above may be used, and other types of ionic liquids known in the art may also be used. In one example, the ionic liquid can include bromobutane and/or vinylimidazole. It is understood that bromobutane and vinylimidazole can react and form ionic liquid monomers. In another example, the base film monomer forming the polyionic liquid film includes, but is not limited to, acrylonitrile. The base film monomer can be acrylonitrile, or a mixture of acrylonitrile and styrene, or other base film monomers with similar functions or functions commonly used in the field.

The polyionic liquid film can further comprise a cross-linking agent, such as N-methylenebisacrylamide (N,N'-methanediylbisprop-2-enamide, abbreviated as MBA). MBA can be used as a cross-linking agent, plays a role in bridging among molecular monomers, and molecules are mutually bonded and cross-linked to form a net structure to promote the inter-molecular chain bonding of the polymer. In addition, the crosslinking agent may comprise one or more other crosslinking agents having similar properties or functions commonly used in the art.

In some variations, the substrate may comprise a glass plate, a stainless steel plate, a hard plastic plate that is not easily penetrated by ultraviolet light, or the like. Glass, for example, has advantages including easily available raw materials and having low cost, having good heat resistance, and being easy to cool after polymerization reaction under ultraviolet irradiation, thereby shortening the operation time.

Figure 35A:
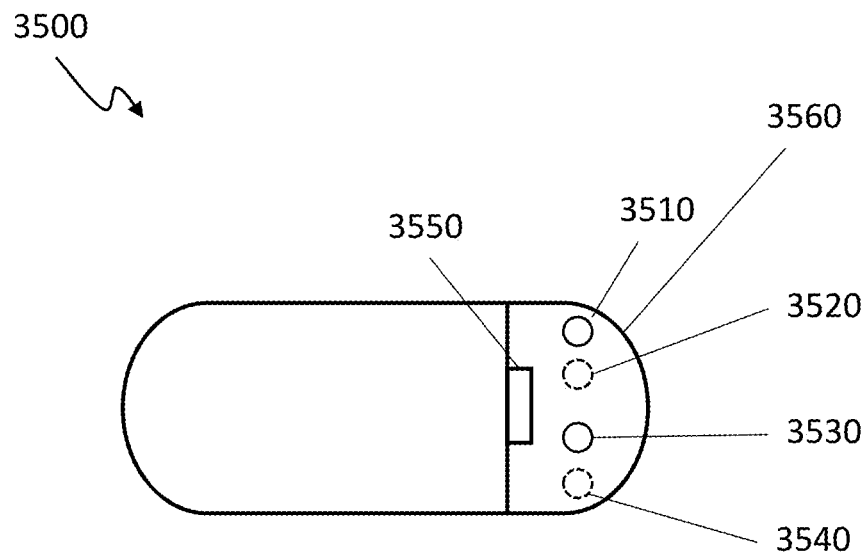
FIGS. 35A and 35B are a side view and end view, respectively, of an illustrative schematic depicting another exemplary of a capsule endoscope comprising detection components.
Figure 35B:
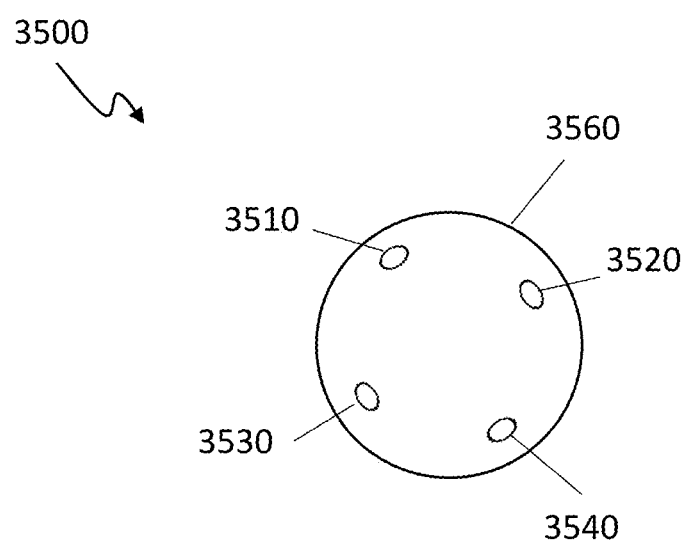

One or more trypsin sensors may be incorporated in or on a capsule endoscope. For example, FIGS. 35A and 35B depict an example variation of a capsule endoscope 3500, which may be similar to any one or more of the above-described capsule endoscopes described above, except that the capsule endoscope may further include one or more detection components. For example, in some variations, as shown in FIGS. 35A and 35B, the capsule endoscope 3500 may have one or more detection components (e.g., 3510, 3520, 3530, and 3540) attached on the exterior of a cover 3560 (e.g., located at a proximal end or distal end of the capsule endoscope). The cover 3560 may, in some variations, be domed or bulbous (e.g., in the shape of a spherical cap). In some variations, the cover 3560 may be transparent or translucent, and does not obscure the field of view of an image sensor(s) 3550 located within the capsule endoscope. Accordingly, the image sensor 3550 (or multiple image sensors) may be used to visualize the one or more detection components. In some variations, the image sensor 3550 (or multiple image sensors) may be used to visualize the color change of one or more detection components.

The detection components 3510-3540 can detect and/or measure a parameter of the sample. In some variations, the detection components 3510-3540 can detect and/or measure the same parameter. In some variations, the detection components 3510-3540 can detect and/or measure two or more different parameters. In some variations, the parameter can be pH value, occult blood concentration, pepsin concentration, and/or trypsin concentration. For example, in some variations, the detection component 3510 can detect and/or measure a pH value of the sample, the detection component 3520 can detect and/or measure an occult blood concentration, the detection component 3530 can detect and/or measure a pepsin concentration, and the detection component 3540 can detect and/or measure a trypsin concentration.

The trypsin detection film can be incorporated in the capsule endoscope disclosed herein for detecting and/or collecting pancreatic juice. In some variations, the detection components 3510-3540 can comprise the trypsin sensor disclosed herein (e.g., trypsin detection film). In some variations, the capsule endoscope can collect a fluid sample from the digestive track and/or confirm the fluid sample is derived from pancreas using the trypsin sensor. For example, if the fluid sample contains trypsin, it can trigger a color reaction, which can be observed through images taken by the lens.

Although the capsule endoscope 3500 shown in FIGS. 35A and 35B includes four detection components 3510-3540 arranged on a single end of the capsule endoscope, it should be understood that in other variations, a capsule endoscope may include any suitable number (e.g., one, two, three, four, five, six, or more detection elements) arranged in any suitable manner on the capsule endoscope 3500. For example, in some variations, one or more detection components may be arranged on a single end of the capsule endoscope, or on both ends of the capsule endoscope, or any other portion of the capsule endoscope in the field of view of an image sensor. In some variations, at least a portion of the detection components may be arranged generally around a perimeter of the cover 3560 (or near the edges of the field of view of the image sensor), in an equally or unequally distributed manner. Such arrangement around the perimeter may, for example, help avoid obscuring a central region of the field of view of the image sensor 3550, but still enable visualization of the detection components. Additionally or alternatively, at least a portion of the detection components may be grouped in an arc segment of the perimeter of the cover 3560, or grouped in any suitable segment of the cover (e.g., for a spherical cap-shaped cover, at least a portion of the detection components may be arranged along a parallel or meridian of the cover, within a spherical crescent of the cover, etc.).

In some variations, the detection components may be circular as shown in FIGS. 35A and 35B, though may have any suitable shape. For example, the detection components can be circular with a diameter of 1 mm to 5 mm. In some variations, some or all of the detection components may be removable, and may be optionally repositionable and/or replaced with new or unused detection components (e.g., in variations in which the capsule endoscope may be used multiple times, and not disposed after a single use). In other variations, some or all of the detection components may be permanently attached to the capsule endoscope. For example, some or all of the detection components can be glued to the capsule endoscope or attached to the capsule endoscope by tape (e.g., double-sided tape).

Methods for Preparing Trypsin Sensor

Generally, a trypsin sensor (e.g., trypsin detection film) can be prepared by a method comprising contacting a dye (e.g., trypsin detection dye) with a substrate (e.g., polymeric film substrate), thereby attaching the dye to the polymeric film substrate to obtain the trypsin detection film. In some variations, the dye can comprise bromocresol purple dye, 3',5,5'-tetramethyl benzidine dye, triarylmethane dye, xylenol orange dye, metal complex dye, or any combination thereof.

Figure 36:
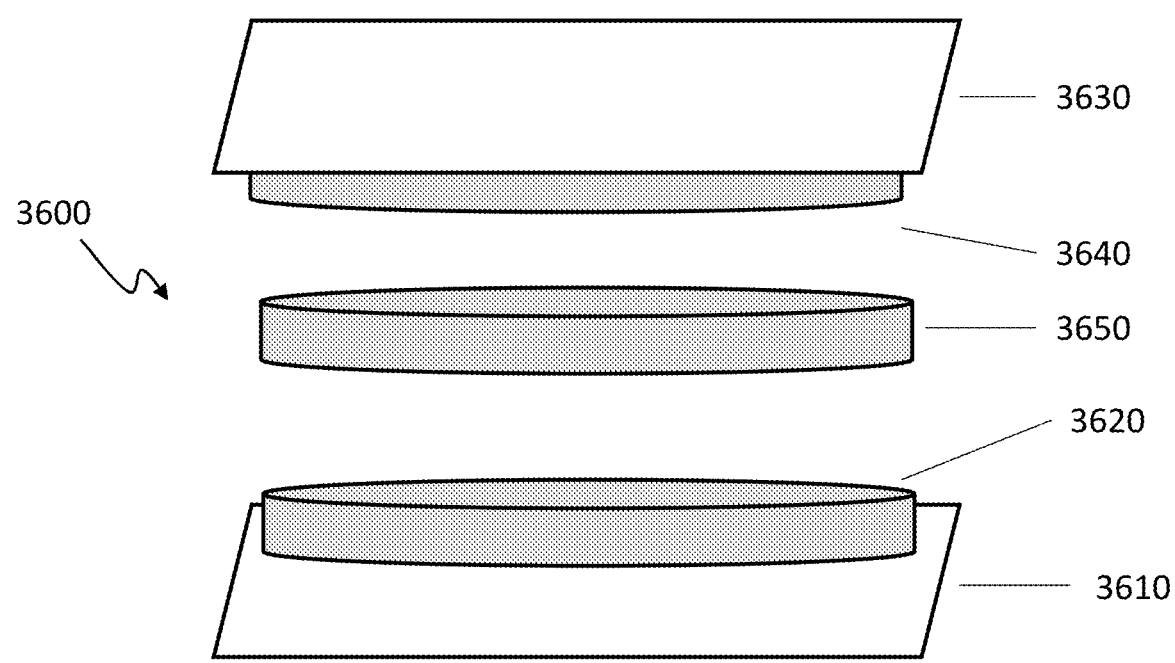
FIG. 36 is an illustrative schematic depicting an exemplary variation of a trypsin detection film.

As shown in FIG. 36A, the method can comprise: (a) placing a layer of film-forming solution 3650 on a base plate 3610 coated with a first lubricant 3620; (b) pressing the film-forming solution 3650 with a cover plate 3630 coated with a second lubricant 3640, wherein the film-forming solution 3650 is in contact with the first lubricant 3620 and the second lubricant 3640, respectively; and (c) initiating a polymerization reaction in the film-forming solution 3650 to form the polymeric film substrate 3600. In some variations, the first lubricant and the second lubricant can each independently comprise white petrolatum, silicone oil, paraffin wax, mineral oil, lubricating grease, or any combinations thereof.

The base plate 3610 in step (a) can comprise a glass plate, a stainless steel plate, or a hard plastic plate. In some variations, the method may further comprise laying tinfoil on the base plate 3610 before coating the base plate 3610 with the first lubricant 3620. The tinfoil can be layered between the base plate 3610 and the first lubricant 3620, for example, by spreading the tinfoil on the base plate 3610 flatly, wrapping the base plate 3610 flatly using the tinfoil, or wiping the tinfoil by a dust-free cloth until the tinfoil has no wrinkles. In some variations, the smooth surface of the tinfoil faces upwards. In some variations, the method may further comprise coating the first lubricant 3620 (e.g., petrolatum) on the base plate 3610 covered with the tinfoil, for example, by wiping the tinfoil using a dust-free cloth until the surface of the tinfoil is smooth. In some variations, the method may further comprise adding a wetting solution to the base plate 3610 prior to laying the tin foil, for example, to exclude air between the base plate 3610 and the tinfoil and/or to smooth the tin foil surface. The wetting solution can be water, ethanol or a mixed solution thereof.

In some variations, the film-forming solution in step (c) comprises a polymerization initiator. In some variations, the polymerization initiator can be 2,4,6-(trimethylbenzoyl) diphenylphosphine oxide (Diphenyl (2,4,6-trimethylbenzoyl) phosphinoxide (TPO), which is a ultraviolet photoinitiator that can be used for initiating UV polymerization reaction of an unsaturated prepolymerization system during photocuring. In some variations, the polymerization initiator can bephotoinitiator 907, photoinitiator 184, azobisisobutyronitrile, benzoin, or any derivative thereof.

In some variations, initiating a polymerization reaction in step (c) comprises irradiating the film-forming solution using a ultraviolet light. The film-forming solution in step (c) comprises a polymerization initiator, such as 2,4,6-(trimethylbenzoyl) diphenylphosphine oxide (Diphenyl (2,4,6-trimethylbenzoyl) phosphinoxide (TPO), bephotoinitiator 907, photoinitiator 184, azobisisobutyronitrile, benzoin, or any derivative thereof. The polymerization initiator can be used for initiating UV polymerization reaction of an unsaturated prepolymerization system during photocuring. In some variations, the wavelength of the ultraviolet light is preferably about 250-400 nm (for example, 250 nm, 300 nm, 325 nm, 350 nm, 375 nm, or 400 nm); and/or the duration of ultraviolet irradiation is preferably about 10-30 min. In some variations, after the ultraviolet light irradiation, the polymeric film substrate is placed in the curing box for 5-10 min. In some variations, the first lubricant and/or the second lubricant, can be inert to and/or non-interfering with ultraviolet light. The first lubricant and the second lubricant can be of the same type or of different types. In some variations, the polymerization reaction may be carried out with heating, for example, while being carried out under irradiation of ultraviolet light. The heating temperature may be about 20 to 60° C., for example, about 20° C., 30° C., 40° C., 50° C., or 60° C.

In some variations, prior to step (a), the film-forming solution is prepared by, optionally, mixing an ionic monomer using a first ultrasonic treatment for about 10-30 min, such as 10 min, 15 min, 20 min, 25 min, or 30 min. In some variations, the film-forming solution is prepared by mixing the ionic monomer, a base membrane monomer, a cross-linking agent, and a polymerization initiator, for example, using a second ultrasonic treatment for about 10-30 min, such as 10 min, 15 min, 20 min, 25 min, or 30 min.

In some variations, the ionic monomer can comprise an imidazole ionic liquid, pyridine ionic liquid, quaternary ammonium salt ionic liquid, quaternary phosphine ionic liquid, pyrrolidine ionic liquid, or any combination thereof. In some variations, the ionic monomer can comprise bromobutane and vinylimidazole. In some variations, the molar ratio of bromobutane to vinylimidazole can be from 2:1 to 1:1, for example, 1:1.

In some variations, the base film monomer can comprise acrylonitrile. To ensure complete reaction, the mass of acrylonitrile can be greater than or preferably equal to the sum of the masses of bromobutane and vinylimidazole.

In some variations, the cross-linking agent can comprise N, N-Methylenebisacrylamide (MBA). The mass of the crosslinking agent can be about 8 to 12 wt %, for example, 8, 9, 10, 11, or 12 wt %, of the total mass of bromobutane, vinylimidazole and acrylonitrile.

In some variations, the polymerization initiator can comprise 2,4,6-(trimethylbenzoyl) diphenylphosphine oxide (TPO). The mass of the polymerization initiator is about 1 to 4% wt, for example, 1 wt %, 1.5 wt %, 2 wt %, 3 wt %, or 4 wt %, of the total mass of bromobutane, vinyl imidazole and acrylonitrile.

In one example, the preparation of the film-forming solution may comprise: mixing bromobutane and vinyl imidazole in equal molar ratio; carrying out a first ultrasonic treatment on the obtained mixed solution for 15 min; adding an amount of acrylonitrile equal to the total mass of bromobutane and vinyl imidazole; adding an amount of MBA that is 8 wt % of the total mass of bromobutane, vinyl imidazole and acrylonitrile; adding an amount of TPO that is 1 wt % of the total mass of bromobutane, vinyl imidazole and acrylonitrile; carrying out a second ultrasonic treatment for 15 min to obtain the film-forming solution (e.g. a clear and transparent liquid). The preparation of the film-forming solution disclosed here can improve the preparation efficiency of the film-forming solution by using an ultrasonic method, greatly shortens the preparation time, is easy to operate, and/or improves controllability.

In some variations, the method further comprises: (d) separating the base plate 3610 and cover plate 3630 from the polymeric film substrate 3600, for example, by immersing the polymeric film substrate 3600 between the base plate 3610 and cover plate 3630 in a standing solution (e.g., for about 10-30 min), to obtain the polymeric film substrate 3600. In some variations, the method further comprises cleaning the polymeric film substrate 3600, for example, by ultrasonic cleaning in a solution (e.g., water or absolute ethanol).

In some variations, the method further comprises: (e) contacting a dye with the polymeric film substrate, thereby attaching the dye to the polymeric film substrate to obtain the trypsin detection film. The temperature for contacting the polymer film substrate with the dye can be 20-40° C., such as 25-35° C.; and/or contacting the polymer film substrate with the dye can be 15-30 min, such as 18-22 min.

The trypsin detection film may be in any suitable shape, for example, a circle, a square, a polygon, or other irregular shape, or may be a sheet, a strip, or the like. The specific shape of the trypsin detection film is not limited in the embodiments of the present application.

Methods for Detecting and/or Collecting Pancreatic Secretions

Also disclosed herein are methods for detecting and/or collecting pancreatic secretions. The method for detecting a pancreatic secretion can comprise: contacting a trypsin detection film with a biological sample, and detecting whether a pancreatic secretion is present in the sample by monitoring the color of a dye attached to the trypsin detection film. In some variations, the color of the dye may indicate that the pancreatic secretion is present in the sample. In some variations, the color of the dye may be different based on the trypsin concentration in the sample. In some variations, the method further comprising comparing the color of the dye to a trypsin detection standard colorimetric card or color scale. The standard color scale or standard colorimetric card for trypsin detection can be prepared by a method comprising: preparing a series of trypsin solutions with a concentration, for example, a series of trypsin solutions with a concentration of 0 µg/mL, 0.5 µg/mL, 5 µg/mL, 10 µg/mL, 25 µg/mL, 100 µg/mL; respectively placing the trypsin solutions with the concentrations in colorimetric containers, respectively adding the same trypsin detection films, standing for a certain time, taking out the trypsin detection films after the color is stable, recording the color development result of the detected trypsin detection films by using image acquisition equipment such as a camera and the like, and after collecting pictures, forming a trypsin standard color gradation by using the pictures with color gradients or printing the pictures (processed by a computer) to prepare the trypsin detection standard colorimetric card.

Further, if the film is not sensitive to color, the color of the trypsin detection film can be analyzed by using color analysis software, for example, HSI RGB value in MATLAB software (the value can fluctuate to a certain extent due to factors such as environment) can be used, and the color of the trypsin detection film can be quantified by using color space knowledge. It is understood that the RGB model is a commonly used color information expression method, which uses the brightness of three primary colors, red, green and blue, to quantitatively express the color. The model is also called additive color mixing model, i.e. a method for realizing color mixing by superposing RGB three-color lights on each other, and any color can be represented by a point in a three-dimensional space in an RGB color space. Therefore, the color variation can be quantified and judged by RGB values. After the pictures of the trypsin detection film are collected, the RGB color analyzer can be used or the pictures can be imported into color analysis software, such as MATLAB, to quantify the color values for comparison, at which time a standard color chart may not be needed. Or, a standard color comparison card can be prepared in advance for comparison, and only the standard color comparison card needs to be compared without importing analysis. For example, the comparative relationship between the RGB color values of the trypsin detection film is shown in Table 1 (below).

TABLE 1

The comparative relationship between the RGB color values of trypsin detection film

| Color | color value before trypsin detection | color value after trypsin detection |
|---|---|---|
| Red (R) | 17 | 172 |
| Green (G) | 95 | 152 |
| Blue (B) | 120 | 17 |

The capsule endoscope comprising a trypsin sensor (e.g., trypsin detection film) can be used for collecting pancreatic juice from a subject. After advancing the capsule endoscope to the region of interest (e.g., duodenum), images of the trypsin detection film captured by capsule endoscope can be monitored. In some variations, the location for pancreatic juice collection is identified by images captured by the capsule endoscope, local pH, trypsin detection film, or any combinations thereof. In some variations, a color change of the trypsin detection film indicates that the concentration of trypsin in the sample is above the detection threshold, which in turn indicates that the location of the capsule endoscope is at the duodenal papilla. The capsule endoscope can be maintained in that position by magnetic force and/or tether tension.

A stimulator can be provided to the subject to induce the secretion of pancreatic juice, for example, at the duodenal papillae. In some variations, the stimulator can be visual (e.g., pictures/videos containing food) or a food smell. In some variations, the stimulator can comprise a hormone such as secretin or cholecystokinin. After the secretion of pancreatic juice is confirmed by the trypsin detection film, a negative pressure may be formed in the tether to withdraw and/or collect the pancreatic juice. In some variations, the tether can be long enough to reach the descending duodenum for people of different body types, such as at least 1.0 or 1.2 m.

Computer programs can be developed for the methods disclosed herein. For example, such a program can identify various locations along the digestive tract, including esophagus, stomach and duodenum. In some variations, artificial intelligence and/or machine learning algorithms can be used for program optimization. In some variations, the program can manipulate and/or guide the capsule into the duodenum. In some variations, if the capsule enters duodenum passively, an alarm can be prompted up in the program. In some variations, if trypsin is detected using the trypsin detection film, an alarm can be prompted in the program. In some variations, the program can display photos or videos of food (e.g., spicy food) to stimulate pancreatic exocrine.

Methods for Analyzing Cancer-Specific Biomarkers

Also disclosed herein are methods for screening cancer specific biomarkers. The term "biomarker" can refer to a naturally-occurring biological molecule, or component or fragment thereof, the measurement of which can provide information useful, for example, in the prognosis of pancreatic cancer. For example, the biomarker may be a naturally-occurring protein or carbohydrate moiety, or an antigenic component or fragment thereof. In some variations, the method can be used for screening and/or identifying pancreatic cancer specific biomarkers from a pancreatic juice, for example, collected using the capsule endoscope disclosed herein. For example, the pancreatic-related biomarkers in Table 2 can be used.

TABLE 2

Pancreatic-related biomarkers

| Biomarker/gene of interest | Related PMID |
|---|---|
| KRAS and GNAS, VHL, TP53 | PubMed: 26253305 |
| Telomerase activity | PubMed: 27230749 |
| KRAS | PubMed: 25481712 |
| SMAD4 and TP53 | PubMed: 27432539 |
| CD1D, KCNK12, CLEC11A, NDRG4, IKZF1, PKRCB, methylation markers and KRAS mutation | PubMed: 26023084 |
| CA 19-9 | PubMed: 2930108, PubMed: 26431551, PubMed: 24747429, PubMed: 24938522 |
| AACT, THBS1 and HPT. | PubMed: 24571389 |
| ERRB2, TNC and TCM and CA 19-9 | PubMed: 25589628 |
| IGFBP2 and IGFBP3 | PubMed: 27579675 |
| TSP-1 and CA 19-9 | PubMed: 26573598 |

TABLE 2-continued

Pancreatic-related biomarkers

| Biomarker/gene of interest | Related PMID |
|---|---|
| Radiographic features + miRNA signature from miR-200a-3p, 1185-5p, 33a-5p, 574-4p, 664b, | PubMed: 27589689 |
| Branched-chain amino acids ((BCAAs) | PubMed: 25261994 |
| glypican-1 (GPC1) | PubMed: 26106858 |
| cysteine dioxygenase 1 (CDO1) (promoter) | PMID: 32144623 |
| C13orf18, FER1L4, and BMP3 | PMID: 31323382 |
| KRAS/GNAS mutations and alterations in TP53/PIK3CA/PTEN | PMID: 28970292 |
| FOXE1, SLIT2, EYA4, SFRP1 | PMID: 28148542 |
| TBX15, BMP3 | PMID: 31306149 |
| CA 19-9; cytologic and immunohistochemical analysis of MUC1 and MUC2 | |
| A1BG | PMID: 18706098 |
| Caldecrin | PMID: 17198186 |
| DJ-1 | PMID: 18706098 |
| FGB | PMID: 17198186 |
| Lithostathine I α | PMID: 17443640 |
| MMP-9 | PMID: 18706098 |
| L1CAM | PMID: 17198186 |
| Plasminogen | PMID: 17198186 |
| S100A8 | PMID: 17198186 |
| S100A9 | PMID: 17198186 |

In some variations, the methods can be used to detect genetic variations for a condition such as pancreatic cancer and/or pancreatitis. Detecting specific genetic variations, for example polymorphic markers and/or haplotypes, copy number, absence or presence of an allele, or genotype associated with a condition (e.g., disease or disorder) as described herein including pancreatic cancer, can be accomplished by methods known in the art for analyzing nucleic acids and/or detecting sequences at polymorphic or genetically variable sites, for example, amplification techniques, hybridization techniques, sequencing, microarrays/arrays, or any combination thereof. Thus, by use of these methods disclosed herein or other methods available to the person skilled in the art, one or more alleles at polymorphic markers, including microsatellites, single nucleotide polymorphisms (SNPs), single nucleotide variations (SNVs), insertions/deletions (indels), copy number variations (CNVs), or other types of genetic variations, can be identified in a sample (e.g., pancreatic juice) obtained from a subject. In some variations, the genes including KRAS, GNAS, TP53, PIK3CA, PTEN and SMAD4, independently or in combination can be studied for pancreatic cancer, including advanced neoplasia, pancreatic cystic neoplasm, pancreatic intraepithelial neoplasia, intraductal papillary mucinous neoplasms (IPMNs), pancreatic adenocarcinoma or pancreatic ductal adenocarcinoma (PDAC). For example, mutant TP53/SMAD4 concentrations can distinguish PDAC from IPMN cases with 32.4% sensitivity, 100% specificity (area under the curve, AUC 0.73, p=0.0002) and controls (AUC 0.82, p<0.0001) (Singhi et al. 2018. "Preoperative Next-Generation Sequencing of Pancreatic Cyst Fluid Is Highly Accurate in Cyst Classification and Detection of Advanced Neoplasia." *Gut* 67 (12): 2131-41; Springer et al. 2015. "A Combination of Molecular Markers and Clinical Features Improve the Classification of Pancreatic Cysts." *Gastroenterology* 149 (6): 1501-10; Eshleman, James R., Alexis L. Norris, Yoshihiko Sadakari, Marija Debeljak, Michael Borges, Colleen Harrington, Elaine Lin, et al. 2015. "KRAS and Guanine Nucleotide-Binding Protein Mutations in Pancreatic Juice Collected from the Duodenum of Patients at High Risk for Neoplasia Undergoing Endoscopic Ultrasound." *Clinical Gastroenterology and Hepatology: The Official Clinical Practice Journal of the American Gastroenterological Association* 13 (5): 963-969.e4; Yu et al. 2017. "Digital Next-Generation Sequencing Identifies Low-Abundance Mutations in Pancreatic Juice Samples Collected from the Duodenum of Patients with Pancreatic Cancer and Intraductal Papillary Mucinous Neoplasms." *Gut* 66 (9): 1677-87).

In some variations, the methods can be used to detect DNA methylation biomarkers for a condition such as pancreatic cancer and/or pancreatitis. Various methods can be used to identify and/or quantify DNA methylation, including sodium bisulfite conversion and sequencing, differential enzymatic cleavage of DNA, and affinity capture of methylated DNA (e.g., methylated DNA immunoprecipitation (Me-DIP) that uses methyl DNA specific antibody, or methyl capture using methyl-CpG binding domain (MBD) proteins). Restriction enzyme based differential cleavage of methylated DNA can be locus-specific. However, affinity-capture and bisulphite conversion followed by sequencing methods can be used for both gene specific or genome-wide analysis. The most commonly reported DNA affinity capture method is methylated DNA immunoprecipitation (Me-DIP) that uses methyl DNA specific antibody, or methyl capture using methyl-CpG binding domain (MBD) proteins. Other reagents can be used to study DNA methylation. For example, CpG DNA methyltransferase can be used for CpG-methylated gene expression studies in a cell culture system. Similarly, methylated DNA controls can be used for methylation specific PCR after bisulphite conversion of DNA. In some variations, the biomarkers can include CDO1, C13orf18, FER1L4, and BMP3, FOXE1, SLIT2, EYA4, SFRP1, TBX15, BMP3, PKRCB, ppENK, CD1D, KCNK12, CLEC11A, NDRG4, IKZF1, PKRCB, and KRAS. AUC values for CD1D, KCNK12, CLEC11A, NDRG4, IKZF1, PKRCB, and KRAS were 0.92*, 0.88, 0.85, 0.85, 0.84, 0.83, and 0.75, respectively, for pancreatic cancer compared with normal pancreas and 0.92*, 0.73, 0.76, 0.85*, 0.73, 0.77, and 0.62 for pancreatic cancer compared with chronic pancreatitis (Fujiyama et al. 2020. "Promoter DNA Hypermethylation of the Cysteine Dioxygenase 1 (CDO1) Gene in Intraductal Papillary Mucinous Neoplasm (IPMN)." *Annals of Surgical Oncology* 27 (10): 4007-16; Majumder et al. 2020. "Methylated DNA in Pancreatic Juice Distinguishes Patients With Pancreatic Cancer From Controls." *Clinical Gastroenterology and Hepatology: The Official Clinical Practice Journal of the American Gastroenterological Association* 18 (3): 676-683.e3; Majumder et al. 2019. "Novel Methylated DNA Markers Discriminate Advanced Neoplasia in Pancreatic Cysts: Marker Discovery, Tissue Validation, and Cyst Fluid Testing." *The American Journal of Gastroenterology* 114 (9): 1539-49).

In some variations, the methods can be used to detect miRNA biomarkers for a condition such as pancreatic cancer and/or pancreatitis. Various methods can be used to identify and/or quantify miRNA biomarkers, including Northern blotting, quantitative reverse transcription polymerase chain reaction (qRT-PCR), next-generation sequencing, and microarray-based hybridization. In some variations, the biomarkers can include miR-221, miR-21, miR-205 and miR-210c, and pancreatic juice exosome associated miRNA markers such as ex-miR-21 and ex-miR-155, which discriminated PDAC patients from CP patients with area under the curve values of 0.90 and 0.89 (Farrell et al, 2005. "Early Detection Markers in Pancreas Cancer." *Cancer Biomarkers: Section A of Disease Markers* 1 (2-3): 157-75; Wang et al, 2014. "Circulating MicroRNAs in Pancreatic Juice as Candidate Biomarkers of Pancreatic Cancer." *Journal of Cancer* 5 (8): 696-705; Nakamura et al. 2019. "Pancreatic Juice Exosomal MicroRNAs as Biomarkers for Detection of Pancreatic Ductal Adenocarcinoma." *Annals of Surgical Oncology* 26 (7): 2104-11).

In some variations, the methods can be used to detect protein biomarkers for a condition such as pancreatic cancer and/or pancreatitis. Various methods can be used to identify and/or quantify protein biomarkers, such as Warburg-Christian, Lowry, and Bradford assays. In some variations, non-specific methods that detect total protein, including absorbance assay, Bradford assay, biuret test derived assay, BCA assay, Lowry protein assay, fluorescamine assay, amido black assay, colloidal gold assay, Kjeldahl assay and Dumas assay, can be used. In one example, a combination of a monoclonal antibody—Adnab-9, and, K-ras and Her-2/neu in pancreatic secretions can be detected in 75% of PDA (Tanaka et al. 2019. "Cytologic Analysis of Pancreatic Juice Increases Specificity of Detection of Malignant IPMN-A Systematic Review." *Clinical Gastroenterology and Hepatology: The Official Clinical Practice Journal of the American Gastroenterological Association* 17 (11): 2199-2211.e21; Tian et al. 2017. "Pathomechanisms of Oxidative Stress in Inflammatory Bowel Disease and Potential Antioxidant Therapies." Research article. Oxidative Medicine and Cellular Longevity; Chen et al. 2006. "Quantitative Proteomic Profiling of Pancreatic Cancer Juice." *Proteomics* 6 (13): 3871-79; Nakashima et al. 2009. "Usefulness of Human Telomerase Reverse Transcriptase in Pancreatic Juice as a Biomarker of Pancreatic Malignancy." *Pancreas* 38 (5): 527-33; Hayakawa et al. 2019. "Carcinoembryonic Antigen Level in the Pancreatic Juice Is Effective in Malignancy Diagnosis and Prediction of Future Malignant Transformation of Intraductal Papillary Mucinous Neoplasm of the Pancreas." *Journal of Gastroenterology* 54 (11): 1029-37; Tobi et al. 2013. "Prospective Markers for Early Diagnosis and Prognosis of Sporadic Pancreatic Ductal Adenocarcinoma." *Digestive Diseases and Sciences* 58 (3): 744-50; Mori et al. 2013. "A Minimally Invasive and Simple Screening Test for Detection of Pancreatic Ductal Adenocarcinoma Using Biomarkers in Duodenal Juice." *Pancreas* 42 (2): 187-92). In some variations, specific methods that quantify the amount of a single protein, including high-performance liquid chromatography (HPLC), high-performance liquid chromatography (HPLC), enzyme-linked immunosorbent assay (ELISA), protein immunoprecipitation, immunoelectrophoresis, Western blot, and protein immunostaining, can be used.

In some variations, the methods can further comprise a CA19-9 (cancer antigen 19-9), serum miRNA-25, CA-125 (cancer antigen 125), or CEA (carcinoembryonic antigen) assay. CA19-9 is a pancreatic cancer biomarker, and can be used to monitor response to pancreatic cancer treatment and/or cancer progression, to watch for pancreatic cancer recurrence, and/or to aid in the diagnosis of pancreatic cancer. miRNA-25 level can be higher in pancreatic ductal adenocarcinoma (PDAC) than in non-tumor tissues. CA-125 is also known as mucin 16 or MUC16, which is a protein that in humans is encoded by the MUC16 gene. CA-125 can be used as a tumor biomarker that may be elevated in the blood of some patients with specific types of cancers, including pancreatic cancer. CEA can be used as a tumor biomarker for various types of cancers, including pancreatic cancer.

The foregoing description, for purposes of explanation, used specific nomenclature to provide a thorough under-standing of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to explain the principles of the invention and its practical applications, they thereby enable others skilled in the art to utilize the invention and various embodiments with various modifications as are suited to the particular use contemplated. It is intended that the following claims and their equivalents define the scope of the invention.

EXAMPLES

Example 1

The film-forming solution can be prepared using the following method: placing bromobutane and vinyl imidazole in equal molar ratio in a glass bottle, and carrying out ultrasonic oscillation treatment for 15 min until the bromobutane and the vinyl imidazole are fully mixed. Then, after removing impurities, an acrylonitrile solution with the mass equal to that of bromobutane and vinyl imidazole is added, followed by the addition of MBA where MBA accounts for 10% of the total mass of the bromobutane, and the vinyl imidazole and the acrylonitrile and TPO accounts for 2% of the total mass of the bromobutane, the vinyl imidazole and the acrylonitrile. The mixture is then be subject to an ultrasonic oscillation treatment for 30 min to form a clear and transparent film forming solution.

A glass plate is prepared, wetted with water, and then covered with tinfoil on the surface of the glass plate. The smooth surface of the tinfoil faces upwards, and is wiped with a dust-free cloth until no wrinkles exist. The glass plate covered with tinfoil is coated with petrolatum as a first lubricant. The film-forming solution is placed on the tinfoil coated with petrolatum (e.g., using a pipette). The thickness of the final film (e.g., 20-50 μm) can be controlled by the volume of the added film-forming solution. The film-forming solution is slowly pressed by a glass cover plate, which is coated with petrolatum as a second lubricant.

The film-forming solution is then irradiated in a polymerization reaction chamber with ultraviolet light at 250 nm for 15 min to carry out the polymerization reaction to form the transparent film. Keep the film in a curing box for 5 min before it is taken out and kept at room temperature for 15 min. Then, the glass cover plate with the transparent film is submerged in water for 20 min to allow the transparent film to be separated from the glass cover plate. The transparent film is floated on the water surface. The obtained transparent film is cleaned using ultrasonic cleaning in water, absolute ethyl alcohol, and water, sequentially, to obtain the polymeric film substrate. The polymeric film substrate is immersed in 1 mg/mL bromocresol purple dye in absolute ethyl alcohol at 30° C. for 20 min, and cleaned by ultrasonic cleaning using water-absolute ethyl alcohol-water to obtain the trypsin detection film. The trypsin detection film is stored at room temperature.

Example 2

Another trypsin detection film is prepared using a similar method as example 1, except for the choice of the dye. The method in this example includes immersing the polymeric film substrate in 2 mg/mL 3,3',5,5'-tetramethyl benzidine dye in 80% ethyl alcohol at 35° C. for 15 min. The trypsin detection film is cleaned by ultrasonic cleaning using water-absolute ethyl alcohol-water and stored at room temperature.

Example 3

Another trypsin detection film is prepared using a similar method as example 1, except for the choice of the dye. The method in this example includes immersing the polymeric film substrate in 2.5 mg/mL of mixed dye of bromocresol purple dye and xylenol orange dye (the proportion of the two dyes can be 1:1, 1:2, 1:3 or 1:4) in 80% ethyl alcohol at 28° C. for 22 min. The trypsin detection film is cleaned by ultrasonic cleaning using water-absolute ethyl alcohol-water and dried in an oven at 40° C. for 15 min before storage.

Example 4

Another trypsin detection film is prepared using the following steps: mixing bromobutane and vinyl imidazole in a molar ratio of 2:1 into a glass bottle, and carrying out ultrasonic oscillation treatment for 20 min until the bromobutane and the vinyl imidazole are fully mixed. Then, after removing impurities, an acrylonitrile solution with the mass equal to that of bromobutane and vinyl imidazole is added, followed by the addition of MBA where MBA accounts for 8% of the total mass of the bromobutane, and the vinyl imidazole and the acrylonitrile and TPO accounts for 1% of the total mass of the bromobutane, the vinyl imidazole and the acrylonitrile. The mixture is then be subject to an ultrasonic oscillation treatment for 30 min to form a clear and transparent film forming solution.

A glass plate is prepared, wetted with water, and then covered with tinfoil on the surface of the glass plate. The smooth surface of the tinfoil faces upwards, and is wiped with a dust-free cloth until no wrinkles exist. The glass plate covered with tinfoil is coated with petrolatum as a first lubricant. The film-forming solution is placed on the tinfoil coated with petrolatum (e.g., using a pipette). The thickness of the final film (e.g., 20-50 μm) can be controlled by the volume of the added film-forming solution. The film-forming solution is slowly pressed by a glass cover plate, which is coated with petrolatum as a second lubricant.

The film-forming solution is then irradiated in a polymerization reaction chamber with ultraviolet light at 300 nm for 15 min to carry out the polymerization reaction to form the transparent film. Keep the film in a curing box for 10 min before it is taken out and kept at room temperature for 15 min. Then, the glass cover plate with the transparent film is submerged in water for 25 min to allow the transparent film to be separated from the glass cover plate. The transparent film is floated on the water surface. The obtained transparent film is cleaned using ultrasonic cleaning in water, absolute ethyl alcohol, and water, sequentially, to obtain the polymeric film substrate. The polymeric film substrate is immersed in 1 mg/mL bromocresol purple dye in absolute ethyl alcohol at 30° C. for 20 min, and cleaned by ultrasonic cleaning using water-absolute ethyl alcohol-water to obtain the trypsin detection film. The trypsin detection film is stored at room temperature.

Example 5

Another trypsin detection film is prepared using the following steps: mixing bromobutane and vinyl imidazole in a molar ratio of 1.2:1 into a glass bottle, and carrying out ultrasonic oscillation treatment for 25 min until the bromobutane and the vinyl imidazole are fully mixed. Then, after removing impurities, an acrylonitrile solution with the mass equal to that of bromobutane and vinyl imidazole is added, followed by the addition of MBA where MBA accounts for 12% of the total mass of the bromobutane, and the vinyl imidazole and the acrylonitrile and TPO accounts for 4% of the total mass of the bromobutane, the vinyl imidazole and the acrylonitrile. The mixture is then be subject to an ultrasonic oscillation treatment for 20 min to form a clear and transparent film forming solution.

A glass plate is prepared, wetted with water, and then covered with tinfoil on the surface of the glass plate. The smooth surface of the tinfoil faces upwards, and is wiped with a dust-free cloth until no wrinkles exist. The glass plate covered with tinfoil is coated with silicone oil as a first lubricant. The film-forming solution is placed on the tinfoil coated with silicone oil (e.g., using a pipette). The thickness of the final film (e.g., 20-50 μm) can be controlled by the volume of the added film-forming solution. The film-forming solution is slowly pressed by a glass cover plate, which is coated with petrolatum as a second lubricant.

The film-forming solution is then irradiated in a polymerization reaction chamber with ultraviolet light at 265 nm for 18 min to carry out the polymerization reaction to form the transparent film. Keep the film in a curing box for 7 min before it is taken out and kept at room temperature for 15 min. Then, the glass cover plate with the transparent film is submerged in water for 20 min to allow the transparent film to be separated from the glass cover plate. The transparent film is floated on the water surface. The obtained transparent film is cleaned using ultrasonic cleaning in water, absolute ethyl alcohol, and water, sequentially, to obtain the polymeric film substrate. The polymeric film substrate is immersed in 2 mg/mL 3,3',5,5'-tetramethyl benzidine dye in 80% ethyl alcohol at 30° C. for 20 min, and cleaned by ultrasonic cleaning using water-absolute ethyl alcohol-water to obtain the trypsin detection film. The trypsin detection film is stored at room temperature.

Example 6

Another trypsin detection film is prepared using the following steps: mixing bromobutane and vinyl imidazole in a molar ratio of 1:1 into a glass bottle, and carrying out ultrasonic oscillation treatment for 15 min until the bromobutane and the vinyl imidazole are fully mixed. Then, after removing impurities, an acrylonitrile solution with the mass equal to 1.2 times of the total mass of bromobutane and vinyl imidazole is added, followed by the addition of MBA where MBA accounts for 10% of the total mass of the bromobutane, and the vinyl imidazole and the acrylonitrile and TPO accounts for 3% of the total mass of the bromobutane, the vinyl imidazole and the acrylonitrile. The mixture is then be subject to an ultrasonic oscillation treatment for 30 min to form a clear and transparent film forming solution.

A glass plate is prepared, wetted with water, and then covered with tinfoil on the surface of the glass plate. The smooth surface of the tinfoil faces upwards, and is wiped with a dust-free cloth until no wrinkles exist. The glass plate covered with tinfoil is coated with petrolatum as a first lubricant. The film-forming solution is placed on the tinfoil coated with petrolatum (e.g., using a pipette). The thickness of the final film (e.g., 20-50 μm) can be controlled by the volume of the added film-forming solution. The film-forming solution is slowly pressed by a glass cover plate, which is coated with lubricant grease as a second lubricant.

The film-forming solution is then irradiated in a polymerization reaction chamber with ultraviolet light at 400 nm for 15 min to carry out the polymerization reaction to form the transparent film. Keep the film in a curing box for 5 min before it is taken out and kept at room temperature for 15 min. Then, the glass cover plate with the transparent film is submerged in water for 30 min to allow the transparent film to be separated from the glass cover plate. The transparent film is floated on the water surface. The obtained transparent film is cleaned using ultrasonic cleaning in water, absolute ethyl alcohol, and water, sequentially, to obtain the polymeric film substrate. The polymeric film substrate is immersed in 0.5 mg/mL bromocresol purple dye in absolute ethyl alcohol at 30° C. for 20 min, and cleaned by ultrasonic cleaning using water-absolute ethyl alcohol-water to obtain the trypsin detection film. The trypsin detection film is stored at room temperature.

Example 7

Another trypsin detection film is prepared using the following steps: mixing bromobutane and vinyl imidazole in a molar ratio of 1:1 into a glass bottle, and carrying out ultrasonic oscillation treatment for 15 min until the bromobutane and the vinyl imidazole are fully mixed. Then, after removing impurities, an acrylonitrile solution with the mass equal to that of bromobutane and vinyl imidazole is added, followed by the addition of MBA where MBA accounts for 10% of the total mass of the bromobutane, and the vinyl imidazole and the acrylonitrile and TPO accounts for 2% of the total mass of the bromobutane, the vinyl imidazole and the acrylonitrile. The mixture is then be subject to an ultrasonic oscillation treatment for 30 min to form a clear and transparent film forming solution.

A glass plate is prepared (without tinfoil) and coated with petrolatum as a first lubricant. The coated surface is wiped with a dust-free cloth until the surface is smooth. The glass plate covered with tinfoil is coated with petrolatum as a first lubricant. The film-forming solution is placed on the tinfoil coated with petrolatum (e.g., using a pipette). The thickness of the final film (e.g., 20-50 μm) can be controlled by the volume of the added film-forming solution. The film-forming solution is slowly pressed by a glass cover plate, which is coated with petrolatum as a second lubricant.

Example 8

An exemplary clinical study for collecting and screening pancreatic juice is planned as following: 20 individuals will participate, including 10 patients who are suspected of having pancreatic cancer indicated for needle biopsy; 5 patients who have a history of pancreatitis; and 5 healthy volunteers.

Each individual will consume simethicone with water to reduce bubbles/mucus and swallow the capsule. The investigator will look at stomach to observe any abnormalities before moving to the pylorus to stimulate passage. Once the capsule passes the pylorus, video, pH localization and trypsin detection film will be monitored by the capsule. After confirming the location of the pancreatic duct, the capsule will be maintained in that position by magnetic force and/or tether tension.

The individual will be stimulated to secrete from pancreas by thinking about a favorite food (e.g., use pictures and smell). If that fails an injection of secretin may be administered. The investigator will extract juice utilizing syringe or pump. After completion, the investigator will withdraw the capsule from the GI tract by pulling back on the tube. Collected pancreatic juice is stored for subsequent screening/diagnostic work.

A small amount (approximately a thimble full) of pancreatic juice from each individual will be stored in a specialized capsule at the completion of the extraction procedure. The capsules will be labeled to enable tracking to the individual (with confidential HIPAA information removed). The capsule will then be taken to an analyzer for processing. Additional tests (e.g., sequencing) for various pancreatic cancer related biomarkers will be performed on these pancreatic juice samples. In the training phase, a total of 16 capsules with known identity (based on standard procedure: pancreatic cancer, pancreatitis, or healthy). In the test phase, the identity of the remaining 4 capsules will not be available to the analyzer, which will use the result from the training phase to predict the identity of the remaining individual (e.g., positive or negative for pancreatic cancer).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A system, comprising:
a capsule endoscope comprising:
an imaging system; and
a trypsin sensor comprising:
a substrate comprising a polymeric film, and
a dye selected from the group consisting of bromocresol purple dye, 3',5,5'-tetramethyl benzidine dye, triarylmethane dye, xylenol orange dye, and metal complex dye,
wherein the trypsin sensor is configured to detect trypsin in a fluid that is in contact with the trypsin sensor, and wherein the polymeric film comprises bromobutane and vinylimidazole at a molar ratio of between 2:1 to 1:1 bromobutane to vinylimidazole; and
a tether comprising a flexible member comprising a lumen, wherein the flexible member is in fluidic communication with the capsule endoscope.

2. The system of claim 1, wherein the substrate and the dye form a trypsin detection film.

3. The system of claim 1, wherein the trypsin sensor is configured to detect fluid comprising a pancreatic secretion, thereby identifying the location of duodenal papilla.

4. The system of claim 3, wherein the system is configured to withdraw a sample comprising the pancreatic secretion.

5. The system of claim 1, wherein the substrate and the dye form a stable film.

6. The system of claim 1, wherein the dye changes color when in contact with fluid having trypsin present above a predetermined concentration.

7. The system of claim 6, wherein the predetermined concentration of the trypsin in the fluid is at least about 300 µg/mL.

8. The system of claim 1, wherein the polymeric film further comprises acrylonitrile.

9. The system of claim 8, wherein the mass of acrylonitrile is greater than or equal to the sum of the masses of bromobutane and vinylimidazole.

10. The system of claim 1, further comprising a vacuum source arranged in fluidic communication with the lumen.

11. The system of claim 10, wherein the vacuum source comprises a syringe or pump.

12. The system of claim 1, wherein the tether comprises a clamp configured to engage the capsule endoscope.

13. The system of claim 12, wherein the clamp is configured to releasably engage the capsule endoscope.

14. The system of claim 12, wherein the clamp comprises a port configured to be in fluidic communication with the lumen and with an environment outside the clamp while the clamp is engaged with the capsule endoscope.

15. The system of claim 1, wherein the capsule endoscope is magnetically controllable.

16. A method, comprising:
advancing a capsule endoscope into a gastrointestinal tract of a patient, wherein the capsule endoscope comprises an imaging system and a trypsin sensor comprising a substrate and a dye selected from the group consisting of bromocresol purple dye, 3',5,5'-tetramethyl benzidine dye, triarylmethane dye, xylenol orange dye, and metal complex dye, wherein the capsule endoscope is in fluidic communication with a tether comprising a flexible member with a lumen, and wherein the substrate comprises a polymeric film comprising bromobutane and vinylimidazole at a molar ratio between 2:1 and 1:1 bromobutane to vinylimidazole;
positioning the capsule endoscope at a region of interest;
detecting trypsin in a fluid that is in contact with the trypsin sensor; and
withdrawing a sample from the region of interest through the lumen.

17. A system, comprising:
a capsule endoscope comprising:
an imaging system; and
a trypsin sensor comprising:
a substrate comprising a polymeric film, and
a dye selected from the group consisting of bromocresol purple dye, 3',5,5'-tetramethyl benzidine dye, triarylmethane dye, xylenol orange dye, and metal complex dye,
wherein the trypsin sensor is configured to detect trypsin in a fluid that is in contact with the trypsin sensor, wherein the polymeric film comprises bromobutane, vinylimidazole, and acrylonitrile, and wherein the mass of acrylonitrile is greater than or equal to the sum of the masses of bromobutane and vinylimidazole; and
a tether comprising a flexible member comprising a lumen, wherein the flexible member is in fluidic communication with the capsule endoscope.

18. The system of claim 17, wherein the trypsin sensor is configured to detect fluid comprising a pancreatic secretion, thereby identifying the location of duodenal papilla.

19. The system of claim 17, wherein the substrate and the dye form a stable film.

20. The system of claim 17, wherein the dye changes color when in contact with fluid having trypsin present above a predetermined concentration.

* * * * *